US008722384B2

(12) United States Patent
Knutzon et al.

(10) Patent No.: US 8,722,384 B2
(45) Date of Patent: May 13, 2014

(54) METHODS AND COMPOSITIONS FOR SYNTHESIS OF LONG CHAIN POLYUNSATURATED FATTY ACIDS

(75) Inventors: Deborah Knutzon, Granite Bay, CA (US); Pradip Mukerji, Gahanna, OH (US); Yung-Sheng Huang, Upper Arlington, OH (US); Jennifer Thurmond, Columbus, OH (US); Sunita Chaudhary, Pearland, TX (US); Amanda Eun-Yeong Leonard, Gahanna, OH (US)

(73) Assignees: Calgene LLC, Davis, CA (US); Abbott Laboratories, Abbott Park, IL (US)

( * ) Notice: Subject to any disclaimer, the term of this patent is extended or adjusted under 35 U.S.C. 154(b) by 248 days.

(21) Appl. No.: 12/414,274

(22) Filed: Mar. 30, 2009

(65) Prior Publication Data

US 2010/0310710 A1 Dec. 9, 2010
US 2011/0256260 A2 Oct. 20, 2011

Related U.S. Application Data

(60) Division of application No. 09/367,013, filed on Aug. 5, 1999, now Pat. No. 7,531,347, which is a continuation-in-part of application No. 08/834,655, filed on Apr. 11, 1997, now Pat. No. 5,968,809.

(51) Int. Cl.
*C12N 1/20* (2006.01)
*C07H 21/04* (2006.01)

(52) U.S. Cl.
USPC .................................... 435/252.3; 536/23.4

(58) Field of Classification Search
None
See application file for complete search history.

(56) References Cited

U.S. PATENT DOCUMENTS 3,649,295 A 3/1972 Bernhart
4,058,594 A 11/1977 Williams
4,526,793 A 7/1985 Ingenbleek et al.
4,526,902 A 7/1985 Rubin
4,614,663 A 9/1986 Rule
4,666,701 A 5/1987 Horrobin et al.
4,670,285 A 6/1987 Clandinin et al.
4,710,387 A * 12/1987 Uiterwaal et al. .............. 426/72
4,758,592 A 7/1988 Horrobin et al.
4,778,630 A 10/1988 Moreton et al.
4,826,877 A 5/1989 Stewart et al.
4,843,095 A 6/1989 Rubin
4,873,191 A 10/1989 Wagner et al.
4,874,603 A 10/1989 Fratzer
4,876,107 A 10/1989 King et al.
4,910,141 A 3/1990 Wong et al.
4,920,098 A 4/1990 Cotter et al.
4,921,877 A * 5/1990 Cashmere et al. ............ 424/439
4,938,984 A 7/1990 Traitler et al.
5,011,770 A 4/1991 Kung et al.
5,057,419 A 10/1991 Martin et al.
5,116,871 A 5/1992 Horrobin et al.
5,162,215 A 11/1992 Bosselman et al.
5,196,198 A 3/1993 Shaw et al.
5,252,333 A * 10/1993 Horrobin ...................... 424/422
5,366,894 A 11/1994 Clark et al.
5,374,657 A 12/1994 Kyle
5,376,541 A 12/1994 Kawashima et al.
5,407,957 A 4/1995 Kyle et al.
5,426,040 A 6/1995 Cheney et al.
5,443,974 A 8/1995 Hitz et al.
5,492,938 A 2/1996 Kyle et al.
5,512,482 A 4/1996 Voelker et al.
5,530,177 A 6/1996 Bleck et al.
5,545,553 A 8/1996 Gotschlich
5,550,156 A 8/1996 Kyle
5,552,306 A 9/1996 Thomas et al.
5,565,362 A 10/1996 Rosen
5,614,393 A * 3/1997 Thomas et al. ............... 435/134
5,614,400 A 3/1997 Cahoon et al.
5,663,068 A 9/1997 Thomas et al.
5,670,540 A 9/1997 Horrobin et al.
5,689,050 A 11/1997 Thomas et al.
5,789,220 A 8/1998 Thomas et al.
5,968,809 A 10/1999 Knutzon et al.

(Continued)

FOREIGN PATENT DOCUMENTS

EP 0550162 A1 7/1993
EP 0561569 A2 9/1993
EP 0644263 A2 3/1995
EP 0736598 A1 10/1996
JP 7503605 A 4/1995

(Continued)

OTHER PUBLICATIONS

Gurr, "Alpha or Gamma: What's a Double Bond Position Between Friends?" 1. Gamma-linolenic Acid, Lipid Technology (Mar. 1995).

(Continued)

*Primary Examiner* — Anand Desai
(74) *Attorney, Agent, or Firm* — Calfee, Halter & Griswold LLP

(57) ABSTRACT

The present invention relates to fatty acid desaturases able to catalyze the conversion of oleic acid to linoleic acid, linoleic acid to γ-linolenic acid, or of alpha-linolenic acid to stearidonic acid. Nucleic acid sequences encoding desaturases, nucleic acid sequences which hybridize thereto, DNA constructs comprising a desaturase gene, and recombinant host microorganism or animal expressing increased levels of a desaturase are described. Methods for desaturating a fatty acid and for producing a desaturated fatty acid by expressing increased levels of a desaturase are disclosed. Fatty acids, and oils containing them, which have been desaturated by a desaturase produced by recombinant host microorganisms or animals are provided. Pharmaceutical compositions, infant formulas or dietary supplements containing fatty acids which have been desaturated by a desaturase produced by a recombinant host microorganism or animal also are described.

33 Claims, 17 Drawing Sheets

(56) References Cited

U.S. PATENT DOCUMENTS

| | | | | |
|---|---|---|---|---|
| 5,972,664 | A | 10/1999 | Knutzon et al. | |
| 6,048,557 | A * | 4/2000 | Van Den Burg et al. | 426/99 |
| 6,051,754 | A | 4/2000 | Knutzon | |
| 6,075,183 | A | 6/2000 | Knutzon et al. | |
| 6,136,574 | A | 10/2000 | Knutzon et al. | |
| 6,355,861 | B1 | 3/2002 | Thomas | |
| 6,441,208 | B2 * | 8/2002 | Bijl et al. | 554/8 |
| 6,459,018 | B1 | 10/2002 | Knutzon | |
| 6,683,232 | B1 | 1/2004 | Thomas | |
| 7,189,894 | B2 | 3/2007 | Thomas | |
| RE41,139 | E | 2/2010 | Knutzon | |

FOREIGN PATENT DOCUMENTS

| | | | |
|---|---|---|---|
| JP | 8503364 | A | 4/1996 |
| WO | 9113972 | A1 | 9/1991 |
| WO | WO9306712 | | 4/1993 |
| WO | 9311245 | A1 | 6/1993 |
| WO | WO9311245 | | 6/1993 |
| WO | 9405782 | A1 | 3/1994 |
| WO | 9411516 | A1 | 5/1994 |
| WO | WO9411516 | | 5/1994 |
| WO | 9418337 | A1 | 8/1994 |
| WO | WO9418337 | | 8/1994 |
| WO | 9523868 | A1 | 9/1995 |
| WO | 9524488 | A1 | 9/1995 |
| WO | 9524494 | A1 | 9/1995 |
| WO | 9606160 | A1 | 2/1996 |
| WO | WO9610086 | | 4/1996 |
| WO | 9612793 | A1 | 5/1996 |
| WO | 9613591 | A2 | 5/1996 |
| WO | WO9613591 | | 5/1996 |
| WO | 9621037 | A1 | 7/1996 |
| WO | WO9621022 | | 7/1996 |
| WO | WO9621037 | | 7/1996 |
| WO | 9633155 | A1 | 10/1996 |
| WO | WO9730582 | | 8/1997 |
| WO | 9846764 | A1 | 10/1998 |
| WO | 9846765 | A1 | 10/1998 |

OTHER PUBLICATIONS

Hodgson, "Advances in Vector Systems for Gene Therapy," Ex. Opin. Ther. Patents 5 (5):459-468 (1995).

Horrobin, "Medical Roles of Metabolites of Precursor EFA," Inform 6(4):428-434 (Apr. 1995).

Ratledge, "Single cell oils—have they a biotechnological future?" MB Tech. 11 (Jul. 1995).

Reddy and Thomas, "Expression of a cyanobacterial delta-6-desaturase gene results in gamma-linolenic Acid Production in Transgenic Plants," Nature Biotechnology 14:639-642 (May 1996).

Ward, "Microbial Production of long-chain PUFAs," Inform 6(6):683-688 (Jun. 1995).

"Closer to Mother's Milk," the Gist 61:8-9 (Spring 1995).

"Exciting Prospects for Stearidonic Acid Seed Oils," Lipid Technology (Nov. 1996).

Covello, P. et al., "Functional Expression of the Extraplastidial *Arabidopsis thaliana* Oleate Desaturase Gene (FAD2) in *Saccharomyces cerevisiae*," Plant Physiology, vol. 111, No. 1, pp. 223-226, (1996).

L. V. Michaelson, et al., "Isolationo of a Delta-5-Fatty Acid Desaturase Gene from *Mortierella alpina*," Journal of Biological Chemistry, American Society of Biological Chemists, vol. 273, No. 30, Jul. 24, 1998, pp. 19055-19059 (XP-002076636).

Deborah S. Knutson, et al., "Identification of Delta-5-Desaturase from *Mortierella alpina* by Heterologous Expression in Bakers' Yeast and Canola," Journal of Biological Chemistry, American Society of Biological Chemists, vol. 273, No. 45, Nov. 6, 1998, pp. 29360-29366 (XP-002106760).

Hill-Eubanks, et al,; "Structure of a G-Protein-Coupling domain of a Muscarinic Receptor Predicted by Random Saturation Mutagenesis"; The Journal of Biological Chemistry; vol. 271, No. 6, Feb. 9, 1996, pp. 3058-3065; The American Society for Biochemistry and Molecular Biology, Inc.

Shibuya, et al.; "Purification, Characterization, and cDNA Cloning of a Novel a-Galactosidase from *Mortierella vinacea*"; Biosci. Biotech. Biochem., vol. 61, No. 4, 1997; pp. 592-598.

Sambrook, et al.; "Molecular Cloning—A Laboratory Manual, Second Edition"; Cold Spring Harbor Laboratory Press, 1989; pp. 8.46-8.49, 9.47-9.57 and 2.114-2.117.

Bajpai and Bajpai, "Arachidonic Acid Production by Microorganisms," Biotechnology and Applied Biochemistry, 15:1-10, (1992).

Gurr, "Alpha or Gamma: What's a Double Bond Position Between Friends?" I. Gamma-linolenic Acid, Lipid Technology, (Mar. 1995), pp. 62-65.

Hodgson, "Advances in Vector Systems for Gene Therapy," Ex. Opin. Ther. Patents 5(5): 459-468, (1995).

Horrobin, "Medical Roles of Metabolites of Precursor EFA," Inform 6(4): 428-434, (Apr. 1995).

Ratledge, "Single cell oils—have they a biotechnological future?" MB Tech. 11, (Jul. 1995).

Reddy and Thomas, "Expression of a cyanobacterial Δ6-desaturase gene results in gamma-linolenic Acid Production in Transgenic Plants," Nature Biotechnology 14: 639-642, (May 1996).

Ward, "Microbial Production of long-chain PUFAs," Inform 6(6): 683-688, (Jun. 1995).

"Exciting Prospects for Stearidonic Acid Seed Oils," Lipid Technology, (Nov. 1996).

Covello, P. et al., "Functional Expression of the Extraplastidial *Arabidopsis thaliana* Oleate Desaturase Gene (FAD2) in *Saccharomyces cerevisiae*," Plant Physiology, vol. 111, No. 1, pp. 223-226, (May 1996).

L.V. Michaelson, et al., "Isolation of a Δ5-Fatty Acid Desaturase Gene from *Mortierella alpina*", Journal of Biological Chemistry, American Society of Biological Chemists, vol. 273, No. 30, Jul. 24, 1998, pp. 19055-19059, (XP-002076636).

Deborah S. Knutzon, et al., "Identification of Δ5-Desaturase from *Mortierella alpina* by Heterologous Expression in Bakers' Yeast and Canola", Journal of Biological Chemistry, American Society of Biological Chemists, vol. 273, No. 45, Nov. 6, 1998, pp. 29360-29366, (XP-002106760).

Kyte and Doolittle, J. Mol. Biol. 157: 105-132, (1982).

Lue et al., Mol. Cell. Biol., vol. 7, p. 3446, (1987).

Johnston, Microbiol, Rev, vol. 51, p. 458, (1987).

Alber, T. and Kawasaki, G., J. Mol. & Appl. Genetics, 1: 419, (1982).

Ono et al., Comparative Biochemistry and Physiology A, 113(3):287-292, (1996).

Willmut et al., Nature 385:810, (1997).

Brenner et al., Adv. Exp. Med. Biol., vol. 83, pp. 85-101, (1976).

Hoge et al., Experimental Mycology, 6:225-232, (1982).

Okuley et al., The Plant Cell, 6:147-158, (1994).

Ackman, "Problems in Fish Oils and Concentrates," Canadian Institute of Fisheries Technology, Technical University of Nova Scotia, 189-204 (1989).

Horrobin, "Fatty acid metabolism in health and disease: the role of delta-6-desaturase," Am. J. Clin. Nutr., vol. 57 (Suppl.), 732S-737S (1993).

Arondel et al., "Map-Based Cloning of a Gene Controlling Omega-3 Fatty Acid Desaturation in *Arabidopsis*," Science, 258:1353-1355 (1992).

Prosecution history of US RE41139E (Feb. 16, 2010).

International Search Report of WO/98046763 (PCT/US98/07126) of Mar. 9, 1998.

Murata et al., "Biosynthesis of gamma-Linolenic Acid in the *Cyanobacterium spirulina* platensis," In: gamma-Linolenic Acid Metabolism and Its Roles in Nutrition and Medicine (Huang and Mills, eds.), pp. 22-32, Access Press, Champaign, IL (1996).

Napier, et al., "The role of cytochrome b5 fusion desaturases in the synthesis of polyunsaturated fatty acids," Prostaglandins, Leukotrienes and Essential Fatty Acids, vol. 68(2), pp. 135-143 (2003).

(56) References Cited

OTHER PUBLICATIONS

Napier, "Plumbing the depths of PUFA biosynthesis: a novel polyketide synthase-like pathway from marine organisms," Trends in Plant Science, vol. 7(2), pp. 51-54 (2002).
Okayasu, T., et al., "Purification and Partial Characterization of Linoleoyl-CoA Desaturase from Rat Liver Microsomes," Archives of Biochemistry and Biophysics, vol. 206(1), pp. 21-28 (1981).
Paine, et al., "Functional high level expression of cytochrome P450 CYP2D6 using baculoviral expression systems," Archives of Biochemistry and Biophysics, vol. 328(1), pp. 143-150 (1996).
Prasad, M.R., et al., "Purification and Properties of Hen Liver Microsomal Terminal Enzyme Involved in Stearoyl Coenzyme A Desaturation and its Quantitation in Neonatal Chicks," Journal of Biological Chemistry, vol. 254(14), pp. 6362-6369 (1979).
Qui, "Biosynthesis of docosahexaenoic acid (DHA, 22:6-4, 7,10,13,16,19): two distinct pathways," Prostaglandins, Leukotrienes, and Essential Fatty Acids., vol. 68(2), pp. 181-186 (2003).
Shanklin, et al., "Eight histidine residues are catalytically essential in a membrane-associated iron enzyme, stearoyl-CoA desaturase, and are conserved in alkane hydroxylase and xylene monooxygenase," Biochemistry, vol. 33(43), pp. 12787-12794 (1994).
Strittmatter, P., et al., "Purification and Properties of Rat Liver Microsomal Stearyl Coenzyme A Desaturase," Proceedings of the National Academy of Sciences of the United States of America, vol. 71(11), pp. 4565-4569 (1974).
Yoshino, R., et al., "Development cDNA in *Dictyostelium discoideum*," AC C25549, EMBL Database (Jul. 1997).

* cited by examiner

```
                                                                           60
                                                                           *
CGACACTCCT TCCTTCTTCT CACCCGTCCT AGTCCCCTTC AACCCCCCTC TTTGACAAAG
ACAACAAACC ATG GCT GCT GCT CCC AGT GTG AGG ACG TTT ACT CGG GCC GAG
           Met Ala Ala Ala Pro Ser Val Arg Thr Phe Thr Arg Ala Glu

       120
        *
GTT TTG AAT GCC GAG GCT CTG AAT GAG GGC AAG AAG GAT GCC GAG GCA
Val Leu Asn Ala Glu Ala Leu Asn Glu Gly Lys Lys Asp Ala Glu Ala

                           180
                            *
CCC TTC TTG ATG ATC ATC GAC AAC AAG GTG TAC GAT GTC CGC GAG TTC
Pro Phe Leu Met Ile Ile Asp Asn Lys Val Tyr Asp Val Arg Glu Phe

                                           240
                                            *
GTC CCT GAT CAT CCC GGT GGA AGT GTG ATT CTC ACG CAC GTT GGC AAG
Val Pro Asp His Pro Gly Gly Ser Val Ile Leu Thr His Val Gly Lys

                                                           300
                                                            *
GAC GGC ACT GAC GTC TTT GAC ACT TTT CAC CCC GAG GCT GCT TGG GAG
Asp Gly Thr Asp Val Phe Asp Thr Phe His Pro Glu Ala Ala Trp Glu

ACT CTT GCC AAC TTT TAC GTT GGT GAT ATT GAC GAG AGC GAC CGC GAT
Thr Leu Ala Asn Phe Tyr Val Gly Asp Ile Asp Glu Ser Asp Arg Asp

       360
        *
ATC AAG AAT GAT GAC TTT GCG GCC GAG GTC CGC AAG CTG CGT ACC TTG
Ile Lys Asn Asp Asp Phe Ala Ala Glu Val Arg Lys Leu Arg Thr Leu
```

FIG.3A

```
                                420
                                 *
TTC CAG TCT CTT GGT TAC TAC GAT TCT TCC AAG GCA TAC TAC GCC TTC
Phe Gln Ser Leu Gly Tyr Tyr Asp Ser Ser Lys Ala Tyr Tyr Ala Phe
                                            480
                                             *
AAG GTC TCG TTC AAC CTC TGC ATC TGG GGT TTG TCG ACG GTC ATT GTG
Lys Val Ser Phe Asn Leu Cys Ile Trp Gly Leu Ser Thr Val Ile Val
                                                        540
                                                         *
GCC AAG TGG GGC CAG ACC TCG ACC CTC GCC AAC GTG CTC TCG GCT GCG
Ala Lys Trp Gly Gln Thr Ser Thr Leu Ala Asn Val Leu Ser Ala Ala

CTT TTG GGT CTG TTC TGG CAG CAG TGC GGA TGG TTG GCT CAC GAC TTT
Leu Leu Gly Leu Phe Trp Gln Gln Cys Gly Trp Leu Ala His Asp Phe
        600
         *
TTG CAT CAC CAG GTC TTC CAG GAC CGT TTC TGG GGT GAT CTT TTC GGC
Leu His His Gln Val Phe Gin Asp Arg Phe Trp Gly Asp Leu Phe Gly
                    660
                     *
GCC TTC TTG GGA GGT GTC TGC CAG GGC TTC TCG TCC TCG TGG TGG AAG
Ala Phe Leu Gly Gly Val Cys Gln Gly Phe Ser Ser Ser Trp Trp Lys
                                            720
                                             *
GAC AAG CAC AAC ACT CAC CAC GCC GCC CCC AAC GTC CAC GGC GAG GAT
Asp Lys His Asn Thr His His Ala Ala Pro Asn Val His Gly Glu Asp
```

FIG.3B

```
                                                            780
                                                             *
CCC GAC ATT GAC ACC CAC CCT CTG TTG ACC TGG AGT GAG CAT GCG TTG
Pro Asp Ile Asp Thr His Pro Leu Leu Thr Trp Ser Glu His Ala Leu

GAG ATG TTC TCG GAT GTC CCA GAT GAG GAG CTG ACC CGC ATG TGG TCG
Glu Met Phe Ser Asp Val Pro Asp Glu Glu Leu Thr Arg Met Trp Ser
        840
         *
CGT TTC ATG GTC CTG AAC CAG ACC TGG TTT TAC TTC CCC ATT CTC TCG
Arg Phe Met Val Leu Asn Gln Thr Trp Phe Tyr Phe Pro Ile Leu Ser
                        900
                         *
TTT GCC CGT CTC TCC TGG TGC CTC CAG TCC ATT CTC TTT GTG CTG CCT
Phe Ala Arg Leu Ser Trp Cys Leu Gln Ser Ile Leu Phe Val Leu Pro
                                        960
                                         *
AAC GGT CAG GCC CAC AAG CCC TCG GGC GCG CGT GTG CCC ATC TCG TTG
Asn Gly Gln Ala His Lys Pro Ser Gly Ala Arg Val Pro Ile Ser Leu
                                                           1020
                                                             *
GTC GAG CAG CTG TCG CTT GCG ATG CAC TGG ACC TGG TAC CTC GCC ACC
Val Glu Gln Leu Ser Leu Ala Met His Trp Thr Trp Tyr Leu Ala Thr

ATG TTC CTG TTC ATC AAG GAT CCC GTC AAC ATG CTG GTG TAC TTT TTG
Met Phe Leu Phe Ile Lys Asp Pro Val Asn Met Leu Val Tyr Phe Leu
       1080
         *
GTG TCG CAG GCG GTG TGC GGA AAC TTG TTG GCG ATC GTG TTC TCG CTC
Val Ser Gln Ala Val Cys Gly Asn Leu Leu Ala Ile Val Phe Ser Leu
```

FIG.3C

```
                              1140
                                 *
AAC CAC AAC GGT ATG CCT GTG ATC TCG AAG GAG GAG GCG GTC GAT ATG
Asn His Asn Gly Met Pro Val Ile Ser Lys Glu Glu Ala Val Asp Met
                                          1200
                                             *
GAT TTC TTC ACG AAG CAG ATC ATC ACG GGT CGT GAT GTC CAC CCG GGT
Asp Phe Phe Thr Lys Gln Ile Ile Thr Gly Arg Asp Val His Pro Gly
                                                      1200
                                                         *
CTA TTT GCC AAC TGG TTC ACG GGT GGA TTG AAC TAT CAG ATC GAG CAC
Leu Phe Ala Asn Trp Phe Thr Gly Gly Leu Asn Tyr Gln Ile Glu His

CAC TTG TTC CCT TCG ATG CCT CGC CAC AAC TTT TCA AAG ATC CAG CCT
His Leu Phe Pro Ser Met Pro Arg His Asn Phe Ser Lys Ile Gln Pro
     1320
        *
GCT GTC GAG ACC CTG TGC AAA AAG TAC AAT GTC CGA TAC CAC ACC ACC
Ala Val Glu Thr Leu Cys Lys Lys Tyr Asn Val Arg Tyr His Thr Thr
                              1380
                                 *
GGT ATG ATC GAG GGA ACT GCA GAG GTC TTT AGC CGT CTG AAC GAG GTC
Gly Met Ile Glu Gly Thr Ala Glu Val Phe Ser Arg Leu Asn Glu Val
                                          1440
                                             *
TCC AAG GCT GCC TCC AAG ATG GGT AAG GCG CAG TAAAAAAAA AAACAAGGAC
Ser Lys Ala Ala Ser Lys Met Gly Lys Ala Gln
```

```
                                                 1500
                                                    *
GTTTTTTTTC GCCAGTGCCT GTGCCTGTGC CTGCTTCCCT TGTCAAGTCG AGCGTTTCTG

                                                 1560
                                                    *
GAAAGGATCG TTCAGTGCAG TATCATCATT CTCCTTTTAC CCCCCGCTCA TATCTCATTC

ATTTCTCTTA TTAAACAACT TGTTCCCCCC TTCACCG
```

```
                                                                  60
                                                                   *
GTCCCCTGTC GCTGTCGGCA CACCCCATCC TCCCTCGCTC CCTCTGCGTT TGTCCTTGGC

                                                                 120
                                                                   *
CCACCGTCTC TCCTCCACCC TCCGAGACGA CTGCAACTGT AATCAGGAAC CGACAAATAC

                                                                 180
                                                                   *
ACGATTTCTT TTTACTCAGC ACCAACTCAA AATCCTCAAC CGCAACCCTT TTTCAGG ATG
                                                                 Met

GCA CCT CCC AAC ACT ATC GAT GCC GGT TTG ACC CAG CGT CAT ATC AGC
Ala Pro Pro Asn Thr Ile Asp Ala Gly Leu Thr Gln Arg His Ile Ser

            240
             *
ACC TCG GCC CCA AAC TCG GCC AAG CCT GCC TTC GAG CGC AAC TAC CAG
Thr Ser Ala Pro Asn Ser Ala Lys Pro Ala Phe Glu Arg Asn Tyr Gln

                                300
                                 *
CTC CCC GAG TTC ACC ATC AAG GAG ATC CGA GAG TGC ATC CCT GCC CAC
Leu Pro Glu Phe Thr Ile Lys Glu Ile Arg Glu Cys Ile Pro Ala His

                                                360
                                                 *
TGC TTT GAG CGC TCC GGT CTC CGT GGT CTC TGC CAC GTT GCC ATC GAT
Cys Phe Glu Arg Ser Gly Leu Arg Gly Leu Cys His Val Ala Ile Asp

                                                              420
                                                                *
CTG ACT TGG GCG TCG CTC TTG TTC CTG GCT GCG ACC CAG ATC GAC AAG
Leu Thr Trp Ala Ser Leu Leu Phe Leu Ala Ala Thr Gln Ile Asp Lys

TTT GAG AAT CCC TTG ATC CGC TAT TTG GCC TGG CCT GTT TAC TGG ATC
Phe Glu Asn Pro Leu Ile Arg Tyr Leu Ala Trp Pro Val Tyr Trp Ile
```

FIG. 5B

```
            480
             *
ATG CAG GGT ATT GTC TGC ACC GGT GTC TGG GTG CTG GCT CAC GAG TGT
Met Gln Gly Ile Val Cys Thr Gly Val Trp Val Leu Ala His Glu Cys

                                540
                                 *
GGT CAT CAG TCC TTC TCG ACC TCC AAG ACC CTC AAC AAC ACA GTT GGT
Gly His Gln Ser Phe Ser Thr Ser Lys Thr Leu Asn Asn Thr Val Gly

                                                600
                                                 *
TGG ATC TTG CAC TCG ATG CTC TTG GTC CCC TAC CAC TCC TGG AGA ATC
Trp Ile Leu His Ser Met Leu Leu Val Pro Tyr His Ser Trp Arg Ile

                                                            660
                                                             *
TCG CAC TCG AAG CAC CAC AAG GCC ACT GGC CAT ATG ACC AAG GAC CAG
Ser His Ser Lys His His Lys Ala Thr Gly His Met Thr Lys Asp Gln

GTC TTT GTG CCC AAG ACC CGC TCC CAG GTT GGC TTG CCT CCC AAG GAG
Val Phe Val Pro Lys Thr Arg Ser Gln Val Gly Leu Pro Pro Lys Glu

            720
             *
AAC GCT GCT GCT GCC GTT CAG GAG GAG GAC ATG TCC GTG CAC CTG GAT
Asn Ala Ala Ala Ala Val Gln Glu Glu Asp Met Ser Val His Leu Asp

                                780
                                 *
GAG GAG GCT CCC ATT GTG ACT TTG TTC TGG ATG GTG ATC CAG TTC TTG
Glu Glu Ala Pro Ile Val Thr Leu Phe Trp Met Val Ile Gln Phe Leu

                                                840
                                                 *
TTC GGA TGG CCC GCG TAC CTG ATT ATG AAC GCC TCT GGC CAA GAC TAC
Phe Gly Trp Pro Ala Tyr Leu Ile Met Asn Ala Ser Gly Gln Asp Tyr
```

FIG. 5C

```
                                                                    900
                                                                      *
GGC CGC TGG ACC TCG CAC TTC CAC ACG TAC TCG CCC ATC TTT GAG CCC
Gly Arg Trp Thr Ser His Phe His Thr Tyr Ser Pro Ile Phe Glu Pro

CGC AAC TTT TTC GAC ATT ATT ATC TCG GAC CTC GGT GTG TTG GCT GCC
Arg Asn Phe Phe Asp Ile Ile Ile Ser Asp Leu Gly Val Leu Ala Ala

            960
              *
CTC GGT GCC CTG ATC TAT GCC TCC ATG CAG TTG TCG CTC TTG ACC GTC
Leu Gly Ala Leu Ile Tyr Ala Ser Met Gln Leu Ser Leu Leu Thr Val

                               1020
                                  *
ACC AAG TAC TAT ATT GTC CCC TAC CTC TTT GTC AAC TTT TGG TTG GTC
Thr Lys Tyr Tyr Ile Val Pro Tyr Leu Phe Val Asn Phe Trp Leu Val

                                               1080
                                                  *
CTG ATC ACC TTC TTG CAG CAC ACC GAT CCC AAG CTG CCC CAT TAC CGC
Leu Ile Thr Phe Leu Gln His Thr Asp Pro Lys Leu Pro His Tyr Arg

                                                                   1140
                                                                      *
GAG GGT GCC TGG AAT TTC CAG CGT GGA GCT CTT TGC ACC GTT GAC CGC
Glu Gly Ala Trp Asn Phe Gln Arg Gly Ala Leu Cys Thr Val Asp Arg

TCG TTT GGC AAG TTC TTG GAC CAT ATG TTC CAC GGC ATT GTC CAC ACC
Ser Phe Gly Lys Phe Leu Asp His Met Phe His Gly Ile Val His Thr

           1200
              *
CAT GTG GCC CAT CAC TTG TTC TCG CAA ATG CCG TTC TAC CAT GCT GAG
His Val Ala His His Leu Phe Ser Gln Met Pro Phe Tyr His Ala Glu
```

FIG. 5D

```
                                   1260
                                      *
GAA GCT ACC TAT CAT CTC AAG AAA CTG CTG GGA GAG TAC TAT GTG TAC
Glu Ala Thr Tyr His Leu Lys Lys Leu Leu Gly Glu Tyr Tyr Val Tyr

                                               1320
                                                  *
GAC CCA TCC CCG ATC GTC GTT GCG GTC TGG AGG TCG TTC CGT GAG TGC
Asp Pro Ser Pro Ile Val Val Ala Val Trp Arg Ser Phe Arg Glu Cys

                                                          1380
                                                             *
CGA TTC GTG GAG GAT CAG GGA GAC GTG GTC TTT TTC AAG AAG TAAAAA
Arg Phe Val Glu Asp Gln Gly Asp Val Val Phe Phe Lys Lys

                                                              1440
                                                                 *
AAAAGACAAT GGACCACACA CAACCTTGTC TCTACAGACC TACGTATCAT GTAGCCATAC

CACTTCATAA AAGAACATGA GCTCTAGAGG CGTGTCATTC GCGCCTCC
```

Effect of Host Strain on GLA Production

FastA Match of ma29 and contig 253538a

```
SCORES       Init1:   117 Initn:   225 Opt:   256
Smith-Waterman score: 408;    27.0% identity in 441 aa overlap

                       10        20        30        40        50
ma29gcg.pep  MGTDQGKT---FTWEELAAHNTKDDLLLAIRGRVYDVTKFLSRHPGGVDTLLLGAGRDVT
                 || |   |||:|:| ::  ::  |:|  :||:::::| |||||  ::   ||:|:|
253538a          QGPTPRYFTWDEVAQRSGCEERWLVIDRKVYNISEFTRRHPGGSRVISHYAGQDAT
                        10        20        30        40        50

              60        70        80        90       100       110
ma29gcg.pep  PVFEMYHAF-GAADAIMKKYYVGTLVSNELPIFPEPTVFHKTIKTRVEGYFTDRNIDPKN
              |  :|   | :    |::  :| | | | | | |||  ::       |   | : :   :
253538a      DPFVAFHINKGLVKKYMNSLLIGEL-SPEQPSF-EPTKNKELTDEFRELRATVERMGLMK
              60        70        80          90       100       110

              120       130       140       150         160       170
ma29gcg.pep  RPEIWGRYALIFGSLIASYYAQLFVPFVVERTWLQVVF-AIIMGFACAQVGLNPLHDASH
              :::  : | :  ::      |  :: :|    ::|  :: |:::: : ||:|     || :|
253538a      ANHVF--FLLYLLHILLLDGAAWLTLWVFGTSFLPFLLCAVLLSAVQAQAGWLQ-HDYGH
                  120       130       140       150       160       170

               180       190           200       210       220
ma29gcg.pep  FSVTHNPTVWKILGATHDF----FNGASYLVWMYQHMLGHHPYTNIAGADPDVSTSE---
             :|| ::|  |: |  :| |        ::|||  | ::| : ||   ||   ||||:  :
253538a      LSVYRKPK-WNHL--VHKFVIGHLKGASANWWNHRH-FQHHAKPNIFHKDPDVNMLHVFV
                    180       190       200        210       220

                230       240       250           260       270       280
ma29gcg.pep  ----PDVRRIKPNQKWF-VNHINQHMFV--PFLYGLLAFKVRIQDINILYFVKTNDAIRV
                 ::   | : |::  || ::::|:   | |      : |: :|       |: ::  :: : :
253538a      LGEWQPIEYGKKKLKYLPYNHQHEYFFLIGPPLLIPMYFQYQI----IMTMIVHKNWVDL
             230       240       250       260       270           280

                  290       300       310       320       330       340
ma29gcg.pep  NPISTWHTVMFWGGKAFFVWYRLIVPLQYLPLGKVLLLFTVADMVSSYWLALTFQANHVV
                 :| : ::        ||: |     :|: |  || :||:::    :: |:|:: :  | ||:|
253538a      ----AWAVSYYI---RFFITY---IPF-YGILG-ALLFLNFIRFLESHWFVWVTQMNHIV
                   290                 300           310       320       330

                  350       360            370       380       390
ma29gcg.pep  EEVQWPLPDENGIIQKDWAAMQVETT----QDYAHDSHLWTSITGSLNYQAVHHLFPNVS
              |:      |:::    :||  : |: :|     |:: :|   | |   | ||:|  ||||||::
253538a      MEI-----DQEAY--RDWFSSQLTATCNVEQSFFND---WFS--GHLNFQIEHHLFPTMP
                          340       350       360                370

             400       410       420       430       440
ma29gcg.pep  QHHYPDILAIIKNTCSEYKVPYLVKDTFWQAFASHLEHLRVLGLRPKEEX
              :|:    |   ::|:  |::: :  |    |
253538a      RHNLHKIAPLVKSLCAKHGIEYQEKPLLRALLDIIRSLKKSGKLWLDAYLHKX
           380       390       400       410       420       430
```

Figure 9

FastA Match of ma524 and contig 253538a

```
SCORES        Init1:   231 Initn:   499 Opt:   401
Smith-Waterman score: 620;    27.3% identity in 455 aa overlap

                       10        20        30        40        50        59
ma524gcg.pep MAAAPSVRTFTRAEVLNAEALNEGKKDAEAPFLMIIDNKVYDVREFVPDHPGGSVILTH-
                |: | || ||          :::::   ::|| |||:: ||:  ||||| :::|
253538a         QGPTPRYFTWDEV--------AQRSGCEERWLVIDRKVYNISEFTRRHPGGSRVISHY
                  10                  20        30        40        50

             60        70        80        90        100       110
ma524gcg.pep VGKDGTDVFDTFHPEAAW--ETLANFYVGDIDE---SDRDIKNDDFAAEVRKLRTLFQSL
             :|:|:|| | :|| : :    : : :: :|:::    | :  || ::: | |:||:  : :
253538a      AGQDATDPFVAFHINKGLVKKYMNSLLIGELSPEQPSFEPTKNKELTDEFRELRATVERM
                       60        70        80        90        100       110

               120       130       140       150       160       170
ma524gcg.pep GYYDSSKAYYAFKVSFNLCIWGLSTVIVAKWGQTSTLANVLSAALLGLFWQQCGWLAHDF
             | : :::::: : :    | : | : : :  :| || |   :| |:||:    | ||| ||:
253538a      GLMKANHVFFLLYLLHILLLDGAAWLTLWVFG-TSFLPFLLCAVLLSAVQAQAGWLQHDY
                    120       130       140       150       160

               180       190       200       210       220       230
ma524gcg.pep LHHQVFQDRFWGDLFGAFLGGVCQGFSSSWWKDKHNTHHAAPNVHGEDPDIDTHPLLTWS
              | :|::   |: |   |: |   :| |::||: :|   ||| ||:   :|||::    :|
253538a      GHLSVYRKPKWNHLVHKFVIGHLKGASANWWNHRHFQHHAKPNIFHKDPDVN---ML---
          170       180       190       200       210       220

               240       250       260       270        280       290
ma524gcg.pep EHALEMFSDVPDEELTRMWSRFMVLNQTWFYFPILS---FARLSWCLQSILFVLPNGQAH
              |:: ::::     |  :   :::  |:   || :::    :  : :  | |: ::    :|
253538a      -HVF-VLGEWQPIEYGKKKLKYLPYNHQHEYFFLIGPPLLIPMYFQYQIIMTMI----VH
                 230       240       250       260       270

                300       310       320        330       340       349
ma524gcg.pep KPSGARVPISLVEQLSLAMHWTWYLATMFLFIK--DPVNMLVYFLVSQAVCGNLLAIVFS
             |                : ::||   ::|:  :: :|     :: |::    : : :: :: | :
253538a      K-----------NWVDLAWAVSYYIRFFITYIPFYGILGALLFLNFIRFLESHWFVWVTQ
                     280       290       300       310       320

          350       360       370       380       390       400       409
ma524gcg.pep LNHNGMPVISKEEAVDMDFFTKQIITGRDVHPGLFANWFTGGLNYQIEHHLFPSMPRHNF
             :||  | :    :||   |:|::|: :   :|: ::| :||:| ||:||||||||:|||||:
253538a      MNHIVMEI--DQEAYR-DWFSSQLTATCNVEQSFFNDWFSGHLNFQIEHHLFPTMPRHNL
               330       340       350       360       370       380

          410       420       430       440       450
ma524gcg.pep SKIQPAVETLCKKYNVRYHTTGMIEGTAEVFSRLNEVSKAASKMGKAQX
              || |  |::|| |::::|:   ::::  :::   |:: :|
253538a      HKIAPLVKSLCAKHGIEYQEKPLLRALLDIIRSLKKSGKLWLDAYLHKX
                390       400       410       420       430
```

Figure 10

SEQUENCE LISTING

```
<160> NUMBER OF SEQ ID NOS: 40

<210> SEQ ID NO 1
<211> LENGTH: 1617
<212> TYPE: DNA
<213> ORGANISM: Mortierella alpina
<220> FEATURE:
<221> NAME/KEY: misc_feature
<222> LOCATION: ()..()
<223> OTHER INFORMATION: Description of Combined DNA/RNA Molecule:
      Delta-6 Desaturase Nucleic Acid Sequence
```

```
<400> SEQUENCE: 1

cgacactcct tccttcttct cacccgtcct agtccccttc aacccccctc tttgacaaag     60

acaacaaacc atggctgctg ctcccagtgt gaggacgttt actcgggccg aggttttgaa    120

tgccgaggct ctgaatgagg gcaagaagga tgccgaggca cccttcttga tgatcatcga    180

caacaaggtg tacgatgtcc gcgagttcgt ccctgatcat cccggtggaa gtgtgattct    240

cacgcacgtt ggcaaggacg gcactgacgt ctttgacact tttcaccccg aggctgcttg    300

ggagactctt gccaactttt acgttggtga tattgacgag agcgaccgcg atatcaagaa    360

tgatgacttt gcggccgagg tccgcaagct gcgtaccttg ttccagtctc ttggttacta    420

cgattcttcc aaggcatact acgccttcaa ggtctcgttc aacctctgca tctggggttt    480

gtcgacggtc attgtggcca agtggggcca gacctcgacc ctcgccaacg tgctctcggc    540

tgcgcttttg ggtctgttct ggcagcagtg cggatggttg gctcacgact tttgcatca    600

ccaggtcttc caggaccgtt tctggggtga tcttttcggc gccttcttgg gaggtgtctg    660

ccagggcttc tcgtcctcgt ggtggaagga caagcacaac actcaccacg ccgcccccaa    720

cgtccacggc gaggatcccg acattgacac ccaccctctg ttgacctgga gtgagcatgc    780

gttggagatg ttctcggatg tcccagatga ggagctgacc cgcatgtggt cgcgtttcat    840

ggtcctgaac cagacctggt tttacttccc cattctctcg tttgcccgtc tctcctggtg    900

cctccagtcc attctctttg tgctgcctaa cggtcaggcc cacaagccct cgggcgcgcg    960

tgtgcccatc tcgttggtcg agcagctgtc gcttgcgatg cactggacct ggtacctcgc   1020

caccatgttc ctgttcatca aggatcccgt caacatgctg gtgtactttt tggtgtcgca   1080

ggcggtgtgc ggaaacttgt tggcgatcgt gttctcgctc aaccacaacg gtatgcctgt   1140

gatctcgaag gaggaggcgg tcgatatgga tttcttcacg aagcagatca tcacgggtcg   1200

tgatgtccac ccgggtctat ttgccaactg gttcacgggt ggattgaact atcagatcga   1260

gcaccacttg ttcccttcga tgcctcgcca caacttttca aagatccagc ctgctgtcga   1320

gaccctgtgc aaaaagtaca atgtccgata ccacaccacc ggtatgatcg agggaactgc   1380

agaggtcttt agccgtctga acgaggtctc caaggctgcc tccaagatgg gtaaggcgca   1440

gtaaaaaaaa aaacaaggac gttttttttc gccagtgcct gtgcctgtgc ctgcttccct   1500

tgtcaagtcg agcgtttctg gaaaggatcg ttcagtgcag tatcatcatt ctccttttac   1560

cccccgctca tatctcattc atttctctta ttaaacaact tgttcccccc ttcaccg      1617


<210> SEQ ID NO 2
<211> LENGTH: 457
<212> TYPE: PRT
<213> ORGANISM: Mortierella alpina

<400> SEQUENCE: 2

Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80
```

```
Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Ala Ser Lys Met Gly Lys Ala Gln
    450                 455

<210> SEQ ID NO 3
<211> LENGTH: 1488
<212> TYPE: DNA
<213> ORGANISM: Mortierella alpina

<400> SEQUENCE: 3
```

```
gtcccctgtc gctgtcggca caccccatcc tccctcgctc cctctgcgtt tgtccttggc      60

ccaccgtctc tcctccaccc tccgagacga ctgcaactgt aatcaggaac cgacaaatac     120

acgatttctt tttactcagc accaactcaa aatcctcaac cgcaaccctt tttcaggatg     180

gcacctccca acactatcga tgccggtttg acccagcgtc atatcagcac ctcggcccca     240

aactcggcca agcctgcctt cgagcgcaac taccagctcc ccgagttcac catcaaggag     300

atccgagagt gcatccctgc ccactgcttt gagcgctccg gtctccgtgg tctctgccac     360

gttgccatcg atctgacttg ggcgtcgctc ttgttcctgg ctgcgaccca gatcgacaag     420

tttgagaatc ccttgatccg ctatttggcc tggcctgttt actggatcat gcagggtatt     480

gtctgcaccg gtgtctgggt gctggctcac gagtgtggtc atcagtcctt ctcgacctcc     540

aagaccctca acaacacagt tggttggatc ttgcactcga tgctcttggt cccctaccac     600

tcctggagaa tctcgcactc gaagcaccac aaggccactg gccatatgac caaggaccag     660

gtctttgtgc ccaagacccg ctcccaggtt ggcttgcctc ccaaggagaa cgctgctgct     720

gccgttcagg aggaggacat gtccgtgcac ctggatgagg aggctcccat tgtgactttg     780

ttctggatgg tgatccagtt cttgttcgga tggcccgcgt acctgattat gaacgcctct     840

ggccaagact acggccgctg gacctcgcac ttccacacgt actcgcccat ctttgagccc     900

cgcaactttt tcgacattat tatctcggac ctcggtgtgt tggctgccct cggtgccctg     960

atctatgcct ccatgcagtt gtcgctcttg accgtcacca agtactatat tgtcccctac    1020

ctctttgtca acttttggtt ggtcctgatc accttcttgc agcacaccga tcccaagctg    1080

ccccattacc gcgagggtgc ctggaatttc cagcgtggag ctctttgcac cgttgaccgc    1140

tcgtttggca agttcttgga ccatatgttc cacggcattg tccacaccca tgtggcccat    1200

cacttgttct cgcaaatgcc gttctaccat gctgaggaag ctacctatca tctcaagaaa    1260

ctgctgggag agtactatgt gtacgaccca tccccgatcg tcgttgcggt ctggaggtcg    1320

ttccgtgagt gccgattcgt ggaggatcag ggagacgtgg tctttttcaa gaagtaaaaa    1380

aaaagacaat ggaccacaca caaccttgtc tctacagacc tacgtatcat gtagccatac    1440

cacttcataa aagaacatga gctctagagg cgtgtcattc gcgcctcc                 1488
```

```
<210> SEQ ID NO 4
<211> LENGTH: 399
<212> TYPE: PRT
<213> ORGANISM: Mortierella alpina

<400> SEQUENCE: 4

Met Ala Pro Pro Asn Thr Ile Asp Ala Gly Leu Thr Gln Arg His Ile
1               5                   10                  15

Ser Thr Ser Ala Pro Asn Ser Ala Lys Pro Ala Phe Glu Arg Asn Tyr
            20                  25                  30

Gln Leu Pro Glu Phe Thr Ile Lys Glu Ile Arg Glu Cys Ile Pro Ala
        35                  40                  45

His Cys Phe Glu Arg Ser Gly Leu Arg Gly Leu Cys His Val Ala Ile
    50                  55                  60

Asp Leu Thr Trp Ala Ser Leu Leu Phe Leu Ala Ala Thr Gln Ile Asp
65                  70                  75                  80

Lys Phe Glu Asn Pro Leu Ile Arg Tyr Leu Ala Trp Pro Val Tyr Trp
                85                  90                  95

Ile Met Gln Gly Ile Val Cys Thr Gly Val Trp Val Leu Ala His Glu
            100                 105                 110

Cys Gly His Gln Ser Phe Ser Thr Ser Lys Thr Leu Asn Asn Thr Val
```

```
        115                 120                 125

Gly Trp Ile Leu His Ser Met Leu Leu Val Pro Tyr His Ser Trp Arg
    130                 135                 140

Ile Ser His Ser Lys His His Lys Ala Thr Gly His Met Thr Lys Asp
145                 150                 155                 160

Gln Val Phe Val Pro Lys Thr Arg Ser Gln Val Gly Leu Pro Pro Lys
                165                 170                 175

Glu Asn Ala Ala Ala Ala Val Gln Glu Glu Asp Met Ser Val His Leu
            180                 185                 190

Asp Glu Glu Ala Pro Ile Val Thr Leu Phe Trp Met Val Ile Gln Phe
        195                 200                 205

Leu Phe Gly Trp Pro Ala Tyr Leu Ile Met Asn Ala Ser Gly Gln Asp
    210                 215                 220

Tyr Gly Arg Trp Thr Ser His Phe His Thr Tyr Ser Pro Ile Phe Glu
225                 230                 235                 240

Pro Arg Asn Phe Phe Asp Ile Ile Ile Ser Asp Leu Gly Val Leu Ala
                245                 250                 255

Ala Leu Gly Ala Leu Ile Tyr Ala Ser Met Gln Leu Ser Leu Leu Thr
            260                 265                 270

Val Thr Lys Tyr Tyr Ile Val Pro Tyr Leu Phe Val Asn Phe Trp Leu
        275                 280                 285

Val Leu Ile Thr Phe Leu Gln His Thr Asp Pro Lys Leu Pro His Tyr
    290                 295                 300

Arg Glu Gly Ala Trp Asn Phe Gln Arg Gly Ala Leu Cys Thr Val Asp
305                 310                 315                 320

Arg Ser Phe Gly Lys Phe Leu Asp His Met Phe His Gly Ile Val His
                325                 330                 335

Thr His Val Ala His His Leu Phe Ser Gln Met Pro Phe Tyr His Ala
            340                 345                 350

Glu Glu Ala Thr Tyr His Leu Lys Lys Leu Leu Gly Glu Tyr Tyr Val
        355                 360                 365

Tyr Asp Pro Ser Pro Ile Val Val Ala Val Trp Arg Ser Phe Arg Glu
    370                 375                 380

Cys Arg Phe Val Glu Asp Gln Gly Asp Val Val Phe Phe Lys Lys
385                 390                 395


<210> SEQ ID NO 5
<211> LENGTH: 355
<212> TYPE: PRT
<213> ORGANISM: Mortierella alpina

<400> SEQUENCE: 5

Glu Val Arg Lys Leu Arg Thr Leu Phe Gln Ser Leu Gly Tyr Tyr Asp
1               5                   10                  15

Ser Ser Lys Ala Tyr Tyr Ala Phe Lys Val Ser Phe Asn Leu Cys Ile
            20                  25                  30

Trp Gly Leu Ser Thr Val Ile Val Ala Lys Trp Gly Gln Thr Ser Thr
        35                  40                  45

Leu Ala Asn Val Leu Ser Ala Ala Leu Leu Gly Leu Phe Trp Gln Gln
    50                  55                  60

Cys Gly Trp Leu Ala His Asp Phe Leu His His Gln Val Phe Gln Asp
65                  70                  75                  80

Arg Phe Trp Gly Asp Leu Phe Gly Ala Phe Leu Gly Gly Val Cys Gln
                85                  90                  95

Gly Phe Ser Ser Ser Trp Trp Lys Asp Lys His Asn Thr His His Ala
```

```
            100                 105                 110

Ala Pro Asn Val His Gly Glu Asp Pro Asp Ile Asp Thr His Pro Leu
        115                 120                 125

Leu Thr Trp Ser Glu His Ala Leu Glu Met Phe Ser Asp Val Pro Asp
    130                 135                 140

Glu Glu Leu Thr Arg Met Trp Ser Arg Phe Met Val Leu Asn Gln Thr
145                 150                 155                 160

Trp Phe Tyr Phe Pro Ile Leu Ser Phe Ala Arg Leu Ser Trp Cys Leu
                165                 170                 175

Gln Ser Ile Leu Phe Val Leu Pro Asn Gly Gln Ala His Lys Pro Ser
            180                 185                 190

Gly Ala Arg Val Pro Ile Ser Leu Val Glu Gln Leu Ser Leu Ala Met
        195                 200                 205

His Trp Thr Trp Tyr Leu Ala Thr Met Phe Leu Phe Ile Lys Asp Pro
    210                 215                 220

Val Asn Met Leu Val Tyr Phe Leu Val Ser Gln Ala Val Cys Gly Asn
225                 230                 235                 240

Leu Leu Ala Ile Val Phe Ser Leu Asn His Asn Gly Met Pro Val Ile
                245                 250                 255

Ser Lys Glu Glu Ala Val Asp Met Asp Phe Phe Thr Lys Gln Ile Ile
            260                 265                 270

Thr Gly Arg Asp Val His Pro Gly Leu Phe Ala Asn Trp Phe Thr Gly
        275                 280                 285

Gly Leu Asn Tyr Gln Ile Glu His His Leu Phe Pro Ser Met Pro Arg
    290                 295                 300

His Asn Phe Ser Lys Ile Gln Pro Ala Val Glu Thr Leu Cys Lys Lys
305                 310                 315                 320

Tyr Asn Val Arg Tyr His Thr Thr Gly Met Ile Glu Gly Thr Ala Glu
                325                 330                 335

Val Phe Ser Arg Leu Asn Glu Val Ser Lys Ala Ala Ser Lys Met Gly
            340                 345                 350

Lys Ala Gln
        355


<210> SEQ ID NO 6
<211> LENGTH: 104
<212> TYPE: PRT
<213> ORGANISM: Arabidopsis thaliana
<220> FEATURE:
<221> NAME/KEY: UNSURE
<222> LOCATION: (1)..(104)
<223> OTHER INFORMATION: Amino acids 27, 48, and 63 uncertain of
      sequence

<400> SEQUENCE: 6

Val Thr Leu Tyr Thr Leu Ala Phe Val Ala Ala Asn Ser Leu Gly Val
1               5                   10                  15

Leu Tyr Gly Val Leu Ala Cys Pro Ser Val Xaa Pro His Gln Ile Ala
            20                  25                  30

Ala Gly Leu Leu Gly Leu Leu Trp Ile Gln Ser Ala Tyr Ile Gly Xaa
        35                  40                  45

Asp Ser Gly His Tyr Val Ile Met Ser Asn Lys Ser Asn Asn Xaa Phe
    50                  55                  60

Ala Gln Leu Leu Ser Gly Asn Cys Leu Thr Gly Ile Ile Ala Trp Trp
65                  70                  75                  80

Lys Trp Thr His Asn Ala His His Leu Ala Cys Asn Ser Leu Asp Tyr
                85                  90                  95
```

```
Gly Pro Asn Leu Gln His Ile Pro
            100


<210> SEQ ID NO 7
<211> LENGTH: 252
<212> TYPE: PRT
<213> ORGANISM: Arabidopsis thaliana

<400> SEQUENCE: 7

Gly Val Leu Tyr Gly Val Leu Ala Cys Thr Ser Val Phe Ala His Gln
1               5                   10                  15

Ile Ala Ala Ala Leu Leu Gly Leu Leu Trp Ile Gln Ser Ala Tyr Ile
            20                  25                  30

Gly His Asp Ser Gly His Tyr Val Ile Met Ser Asn Lys Ser Tyr Asn
        35                  40                  45

Arg Phe Ala Gln Leu Leu Ser Gly Asn Cys Leu Thr Gly Ile Ser Ile
    50                  55                  60

Ala Trp Trp Lys Trp Thr His Asn Ala His His Leu Ala Cys Asn Ser
65                  70                  75                  80

Leu Asp Tyr Asp Pro Asp Leu Gln His Ile Pro Val Phe Ala Val Ser
                85                  90                  95

Thr Lys Phe Phe Ser Ser Leu Thr Ser Arg Phe Tyr Asp Arg Lys Leu
            100                 105                 110

Thr Phe Gly Pro Val Ala Arg Phe Leu Val Ser Tyr Gln His Phe Thr
        115                 120                 125

Tyr Tyr Pro Val Asn Cys Phe Gly Arg Ile Asn Leu Phe Ile Gln Thr
    130                 135                 140

Phe Leu Leu Leu Phe Ser Lys Arg Glu Val Pro Asp Arg Ala Leu Asn
145                 150                 155                 160

Phe Ala Gly Ile Leu Val Phe Trp Thr Trp Phe Pro Leu Leu Val Ser
                165                 170                 175

Cys Leu Pro Asn Trp Pro Glu Arg Phe Phe Phe Val Phe Thr Ser Phe
            180                 185                 190

Thr Val Thr Ala Leu Gln His Ile Gln Phe Thr Leu Asn His Phe Ala
        195                 200                 205

Ala Asp Val Tyr Val Gly Pro Pro Thr Gly Ser Asp Trp Phe Glu Lys
    210                 215                 220

Gln Ala Ala Gly Thr Ile Asp Ile Ser Cys Arg Ser Tyr Met Asp Trp
225                 230                 235                 240

Phe Phe Gly Gly Leu Gln Phe Gln Leu Glu His His
                245                 250


<210> SEQ ID NO 8
<211> LENGTH: 125
<212> TYPE: PRT
<213> ORGANISM: Arabidopsis thaliana
<220> FEATURE:
<221> NAME/KEY: UNSURE
<222> LOCATION: (1)..(125)
<223> OTHER INFORMATION: Amino acids 2, 3, 30, 121, and 125 uncertain of
      sequence

<400> SEQUENCE: 8

Gly Xaa Xaa Asn Phe Ala Gly Ile Leu Val Phe Trp Thr Trp Phe Pro
1               5                   10                  15

Leu Leu Val Ser Cys Leu Pro Asn Trp Pro Glu Arg Phe Xaa Phe Val
            20                  25                  30

Phe Thr Gly Phe Thr Val Thr Ala Leu Gln His Ile Gln Phe Thr Leu
```

```
        35                  40                  45

Asn His Phe Ala Ala Asp Val Tyr Val Gly Pro Pro Thr Gly Ser Asp
    50                  55                  60

Trp Phe Glu Lys Gln Ala Ala Gly Thr Ile Asp Ile Ser Cys Arg Ser
65                  70                  75                  80

Tyr Met Asp Trp Phe Phe Cys Gly Leu Gln Phe Gln Leu Glu His His
                85                  90                  95

Leu Phe Pro Arg Leu Pro Arg Cys His Leu Arg Lys Val Ser Pro Val
            100                 105                 110

Gly Gln Arg Gly Phe Gln Arg Lys Xaa Asn Leu Ser Xaa
        115                 120                 125


<210> SEQ ID NO 9
<211> LENGTH: 131
<212> TYPE: PRT
<213> ORGANISM: Homo sapiens
<220> FEATURE:
<221> NAME/KEY: UNSURE
<222> LOCATION: (1)..(131)
<223> OTHER INFORMATION: Amino acid at 110 uncertain of sequence

<400> SEQUENCE: 9

Pro Ala Thr Glu Val Gly Gly Leu Ala Trp Met Ile Thr Phe Tyr Val
1               5                   10                  15

Arg Phe Phe Leu Thr Tyr Val Pro Leu Leu Gly Leu Lys Ala Phe Leu
            20                  25                  30

Gly Leu Phe Phe Ile Val Arg Phe Leu Glu Ser Asn Trp Phe Val Trp
        35                  40                  45

Val Thr Gln Met Asn His Ile Pro Met His Ile Asp His Asp Arg Asn
    50                  55                  60

Met Asp Trp Val Ser Thr Gln Leu Gln Ala Thr Cys Asn Val His Lys
65                  70                  75                  80

Ser Ala Phe Asn Asp Trp Phe Ser Gly His Leu Asn Phe Gln Ile Glu
                85                  90                  95

His His Leu Phe Pro Thr Met Pro Arg His Asn Tyr His Xaa Val Ala
            100                 105                 110

Pro Leu Val Gln Ser Leu Cys Ala Lys His Gly Ile Glu Tyr Gln Ser
        115                 120                 125

Lys Pro Leu
    130


<210> SEQ ID NO 10
<211> LENGTH: 87
<212> TYPE: PRT
<213> ORGANISM: Caenorhabditis elegans

<400> SEQUENCE: 10

Cys Ser Pro Lys Ser Ser Pro Thr Arg Asn Met Thr Pro Ser Pro Phe
1               5                   10                  15

Ile Asp Trp Leu Trp Gly Gly Leu Asn Tyr Gln Ile Glu His His Leu
            20                  25                  30

Phe Pro Thr Met Pro Arg Cys Asn Leu Asn Arg Cys Met Lys Tyr Val
        35                  40                  45

Lys Glu Trp Cys Ala Glu Asn Asn Leu Pro Tyr Leu Val Asp Asp Tyr
    50                  55                  60

Phe Val Gly Tyr Asn Leu Asn Leu Gln Gln Leu Lys Asn Met Ala Glu
65                  70                  75                  80

Leu Val Gln Ala Lys Ala Ala
```

85

<210> SEQ ID NO 11
<211> LENGTH: 143
<212> TYPE: PRT
<213> ORGANISM: Homo sapiens
<220> FEATURE:
<221> NAME/KEY: UNSURE
<222> LOCATION: (1)..(143)
<223> OTHER INFORMATION: Amino acid 125 uncertain of sequence

<400> SEQUENCE: 11

```
Arg His Glu Ala Ala Arg Gly Gly Thr Arg Leu Ala Tyr Met Leu Val
1               5                   10                  15

Cys Met Gln Trp Thr Asp Leu Leu Trp Ala Ala Ser Phe Tyr Ser Arg
            20                  25                  30

Phe Phe Leu Ser Tyr Ser Pro Phe Tyr Gly Ala Thr Gly Thr Leu Leu
        35                  40                  45

Leu Phe Val Ala Val Arg Val Leu Glu Ser His Trp Phe Val Trp Ile
    50                  55                  60

Thr Gln Met Asn His Ile Pro Lys Glu Ile Gly His Glu Lys His Arg
65                  70                  75                  80

Asp Trp Ala Ser Ser Gln Leu Ala Ala Thr Cys Asn Val Glu Pro Ser
                85                  90                  95

Leu Phe Ile Asp Trp Phe Ser Gly His Leu Asn Phe Gln Ile Glu His
            100                 105                 110

His Leu Phe Pro Thr Met Thr Arg His Asn Tyr Arg Xaa Val Ala Pro
        115                 120                 125

Leu Val Lys Ala Phe Cys Ala Lys His Gly Leu His Tyr Glu Val
    130                 135                 140
```

<210> SEQ ID NO 12
<211> LENGTH: 35
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence: PCR Primer

<400> SEQUENCE: 12

```
ccaagcttct gcaggagctc tttttttttt ttttt                                 35
```

<210> SEQ ID NO 13
<211> LENGTH: 33
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined RNA/DNA Molecule:PCR
      Primer

<400> SEQUENCE: 13

```
cuacuacuac uaggagtcct ctacggtgtt ttg                                   33
```

<210> SEQ ID NO 14
<211> LENGTH: 33
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined RNA/DNA Molecule:PCR
      Primer

<400> SEQUENCE: 14
caucaucauc auatgatgct caagctgaaa ctg 33

<210> SEQ ID NO 15
<211> LENGTH: 39
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence: PCR Primer

<400> SEQUENCE: 15
taccaactcg agaaaatggc tgctgctccc agtgtgagg 39

<210> SEQ ID NO 16
<211> LENGTH: 39
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence:PCR Primer

<400> SEQUENCE: 16
aactgatcta gattactgcg ccttacccat cttggaggc 39

<210> SEQ ID NO 17
<211> LENGTH: 39
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence:PCR Primer

<400> SEQUENCE: 17
taccaactcg agaaaatggc acctcccaac actatcgat 39

<210> SEQ ID NO 18
<211> LENGTH: 39
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence:PCR Primer

<400> SEQUENCE: 18
aactgatcta gattacttct tgaaaaagac cacgtctcc 39

<210> SEQ ID NO 19
<211> LENGTH: 746
<212> TYPE: DNA
<213> ORGANISM: Dictyostelium discoideum

<400> SEQUENCE: 19
cgtatgtcac tccattccaa actcgttcat ggtatcataa atatcaacac atttacgctc 60
cactcctcta tggtatttac acactcaaat atcgtactca agattgggaa gcttttgtaa 120
aggatggtaa aaatggtgca attcgtgtta gtgtcgccac aaatttcgat aaggccgctt 180
acgtcattgg taaattgtct tttgttttct tccgtttcat ccttccactc cgttatcata 240
gctttacaga tttaatttgt tatttcctca ttgctgaatt cgtctttggt tggtatctca 300
caattaattt ccaagttagt catgtcgctg aagatctcaa attctttgct acccctgaaa 360

```
gaccagatga accatctcaa atcaatgaag attgggcaat ccttcaactt aaaactactc    420

aagattatgg tcatggttca ctcctttgta cctttttttag tggttcttta aatcatcaag    480

ttgttcatca tttattccca tcaattgctc aagatttcta cccacaactt gtaccaattg    540

taaaagaagt ttgtaaagaa cataacatta cttaccacat taaaccaaac ttcactgaag    600

ctattatgtc acacattaat taccttttaca aaatgggtaa tgatccagat tatgttaaaa    660

aaccattagc ctcaaaagat gattaaatga aataacttaa aaaccaatta tttacttttg    720

acaaacagta atattaataa atacaa                                          746
```

```
<210> SEQ ID NO 20
<211> LENGTH: 228
<212> TYPE: PRT
<213> ORGANISM: Dictyostelium discoideum
<220> FEATURE:
<221> NAME/KEY: UNSURE
<222> LOCATION: (1)..(228)
<223> OTHER INFORMATION: Amino acid 228 uncertain of sequence

<400> SEQUENCE: 20

Tyr Val Thr Pro Phe Gln Thr Arg Ser Trp Tyr His Lys Tyr Gln His
1               5                   10                  15

Ile Tyr Ala Pro Leu Leu Tyr Gly Ile Tyr Thr Leu Lys Tyr Arg Thr
            20                  25                  30

Gln Asp Trp Glu Ala Phe Val Lys Asp Gly Lys Asn Gly Ala Ile Arg
        35                  40                  45

Val Ser Val Ala Thr Asn Phe Asp Lys Ala Ala Tyr Val Ile Gly Lys
    50                  55                  60

Leu Ser Phe Val Phe Phe Arg Phe Ile Leu Pro Leu Arg Tyr His Ser
65                  70                  75                  80

Phe Thr Asp Leu Ile Cys Tyr Phe Leu Ile Ala Glu Phe Val Phe Gly
                85                  90                  95

Trp Tyr Leu Thr Ile Asn Phe Gln Val Ser His Val Ala Glu Asp Leu
            100                 105                 110

Lys Phe Phe Ala Thr Pro Glu Arg Pro Asp Glu Pro Ser Gln Ile Asn
        115                 120                 125

Glu Asp Trp Ala Ile Leu Gln Leu Lys Thr Thr Gln Asp Tyr Gly His
    130                 135                 140

Gly Ser Leu Leu Cys Thr Phe Phe Ser Gly Ser Leu Asn His Gln Val
145                 150                 155                 160

Val His His Leu Phe Pro Ser Ile Ala Gln Asp Phe Tyr Pro Gln Leu
                165                 170                 175

Val Pro Ile Val Lys Glu Val Cys Lys Glu His Asn Ile Thr Tyr His
            180                 185                 190

Ile Lys Pro Asn Phe Thr Glu Ala Ile Met Ser His Ile Asn Tyr Leu
        195                 200                 205

Tyr Lys Met Gly Asn Asp Pro Asp Tyr Val Lys Lys Pro Leu Ala Ser
    210                 215                 220

Lys Asp Asp Xaa
225


<210> SEQ ID NO 21
<211> LENGTH: 494
<212> TYPE: DNA
<213> ORGANISM: Phaeodactylum tricornutum
<220> FEATURE:
<221> NAME/KEY: misc_feature
<222> LOCATION: ()..()
```

<223> OTHER INFORMATION: n at positions 11,20,29,31,40,53,453,489 may be a, c, g, or t

<400> SEQUENCE: 21

```
ttttggaagg ntccaagttn accacggant nggcaagttn acggggcgga aancggtttt     60

ccccccaagc cttttgtcga ctggttctgt ggtggcttcc agtaccaagt cgaccaccac    120

ttattcccca gcctgccccg acacaatctg gccaagacac acgcactggt cgaatcgttc    180

tgcaaggagt ggggtgtcca gtaccacgaa gccgacctcg tggacgggac catggaagtc    240

ttgcaccatt tgggcagcgt ggccggcgaa ttcgtcgtgg attttgtacg cgacggaccc    300

gccatgtaat cgtcgttcgt gacgatgcaa gggttcacgc acatctacac acactcactc    360

acacaactag tgtaactcgt atagaattcg gtgtcgacct ggaccttgtt tgactggttg    420

gggatagggt aggtaggcgg acgcgtgggt cgnccccggg aattctgtga ccggtacctg    480

gcccgcgtna aagt                                                      494
```

<210> SEQ ID NO 22
<211> LENGTH: 102
<212> TYPE: PRT
<213> ORGANISM: Phaeodactylum tricornutum
<220> FEATURE:
<221> NAME/KEY: UNSURE
<222> LOCATION: (1)..(102)
<223> OTHER INFORMATION: Amino acids 4,7,10,11,14, and 18 uncertain of sequence

<400> SEQUENCE: 22

```
Phe Trp Lys Xaa Pro Ser Xaa Pro Arg Xaa Xaa Gln Val Xaa Gly Ala
1               5                   10                  15

Glu Xaa Gly Phe Pro Pro Lys Pro Phe Val Asp Trp Phe Cys Gly Gly
            20                  25                  30

Phe Gln Tyr Gln Val Asp His His Leu Phe Pro Ser Leu Pro Arg His
        35                  40                  45

Asn Leu Ala Lys Thr His Ala Leu Val Glu Ser Phe Cys Lys Glu Trp
    50                  55                  60

Gly Val Gln Tyr His Glu Ala Asp Leu Val Asp Gly Thr Met Glu Val
65                  70                  75                  80

Leu His His Leu Gly Ser Val Ala Gly Glu Phe Val Val Asp Phe Val
                85                  90                  95

Arg Asp Gly Pro Ala Met
            100
```

<210> SEQ ID NO 23
<211> LENGTH: 520
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence: Schizochytrium cDNA Clone

<400> SEQUENCE: 23

```
ggatggagtt cgtctggatc gctgtgcgct acgcgacgtg gtttaagcgt catgggtgcg     60

cttgggtaca cgccggggca gtcgttgggc atgtacttgt gcgcctttgg tctcggctgc    120

atttacattt ttctgcagtt cgccgtaagt cacacccatt tgcccgtgag caacccggag    180

gatcagctgc attggctcga gtacgcgcgg accacactgt gaacatcagc accaagtcgt    240

ggtttgtcac atggtggatg tcgaacctca actttcagat cgagcaccac cttttcccca    300
```

```
cggcgcccca gttccgtttc aaggagatca gcccgcgcgt cgaggccctc ttcaagcgcc    360

acggtctccc ttactacgac atgccctaca cgagcgccgt ctccaccacc tttgccaacc    420

tctactccgt cggccattcc gtcggcgacg ccaagcgcga ctagcctctt ttcctagacc    480

ttaattcccc accccacccc atgttctgtc ttcctcccgc                          520


<210> SEQ ID NO 24
<211> LENGTH: 153
<212> TYPE: PRT
<213> ORGANISM: Artificial/Unknown
<220> FEATURE:
<221> NAME/KEY: misc_feature
<222> LOCATION: ()..()
<223> OTHER INFORMATION: Description of Artificial Sequence:
      Schizochytrium cDNA Clone

<400> SEQUENCE: 24

Met Glu Phe Val Trp Ile Ala Val Arg Tyr Ala Thr Trp Phe Lys Arg
1               5                   10                  15

His Gly Cys Ala Trp Val His Ala Gly Ala Val Val Gly His Val Leu
            20                  25                  30

Val Arg Leu Trp Ser Arg Leu His Leu His Phe Ser Ala Val Arg Arg
        35                  40                  45

Lys Ser His Pro Phe Ala Arg Glu Gln Pro Gly Gly Ser Ala Ala Leu
    50                  55                  60

Ala Arg Val Arg Ala Asp His Thr Val Asn Ile Ser Thr Lys Ser Trp
65                  70                  75                  80

Phe Val Thr Trp Trp Met Ser Asn Leu Asn Phe Gln Ile Glu His His
                85                  90                  95

Leu Phe Pro Thr Ala Pro Gln Phe Arg Phe Lys Glu Ile Ser Pro Arg
            100                 105                 110

Val Glu Ala Leu Phe Lys Arg His Gly Leu Pro Tyr Tyr Asp Met Pro
        115                 120                 125

Tyr Thr Ser Ala Val Ser Thr Thr Phe Ala Asn Leu Tyr Ser Val Gly
    130                 135                 140

His Ser Val Gly Asp Ala Lys Arg Asp
145                 150


<210> SEQ ID NO 25
<211> LENGTH: 420
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence:
      Schizochytrium cDNA Clone

<400> SEQUENCE: 25

acgcgtccgc ccacgcgtcc gccgcgagca actcatcaag gaaggctact ttgacccctc     60

gctcccgcac atgacgtacc gcgtggtcga gattgttgtt ctcttcgtgc tttccttttg    120

gctgatgggt cagtcttcac ccctcgcgct cgctctcggc attgtcgtca gcggcatctc    180

tcagggtcgc tgcggctggg taatgcatga gatgggccat gggtcgttca ctggtgtcat    240

ttggcttgac gaccggttgt gcgagttctt ttacggcgtt ggttgtggca tgagcggtca    300

ttactggaaa aaccagcaca gcaaacacca cgcagcgcca aaccggctcg agcacgatgt    360

agatctcaac accttgccat tggtggcctt caacgagcgc gtcgtgcgca aggtccgacc    420


<210> SEQ ID NO 26
```

<211> LENGTH: 140
<212> TYPE: PRT
<213> ORGANISM: Artificial/Unknown
<220> FEATURE:
<221> NAME/KEY: misc_feature
<222> LOCATION: ()..()
<223> OTHER INFORMATION: Description of Artificial Sequence: Schizochytrium cDNA Clone

<400> SEQUENCE: 26

```
Arg Val Arg Pro Arg Val Arg Arg Glu Gln Leu Ile Lys Glu Gly Tyr
1               5                   10                  15

Phe Asp Pro Ser Leu Pro His Met Thr Tyr Arg Val Val Glu Ile Val
            20                  25                  30

Val Leu Phe Val Leu Ser Phe Trp Leu Met Gly Gln Ser Ser Pro Leu
        35                  40                  45

Ala Leu Ala Leu Gly Ile Val Val Ser Gly Ile Ser Gln Gly Arg Cys
    50                  55                  60

Gly Trp Val Met His Glu Met Gly His Gly Ser Phe Thr Gly Val Ile
65                  70                  75                  80

Trp Leu Asp Asp Arg Leu Cys Glu Phe Phe Tyr Gly Val Gly Cys Gly
                85                  90                  95

Met Ser Gly His Tyr Trp Lys Asn Gln His Ser Lys His His Ala Ala
            100                 105                 110

Pro Asn Arg Leu Glu His Asp Val Asp Leu Asn Thr Leu Pro Leu Val
        115                 120                 125

Ala Phe Asn Glu Arg Val Val Arg Lys Val Arg Pro
    130                 135                 140
```

<210> SEQ ID NO 27
<211> LENGTH: 1219
<212> TYPE: DNA
<213> ORGANISM: Homo sapiens

<400> SEQUENCE: 27

```
gcacgccgac cggcgccggg agatcctggc aaagtatcca gagataaagt ccttgatgaa     60

acctgatccc aatttgatat ggattataat tatgatggtt ctcacccagt tgggtgcatt    120

ttacatagta aaagacttgg actggaaatg ggtcatattt ggggcctatg cgtttggcag    180

ttgcattaac cactcaatga ctctggctat tcatgagatt gcccacaatg ctgcctttgg    240

caactgcaaa gcaatgtgga atcgctggtt tggaatgttt gctaatcttc ctattgggat    300

tccatattca atttccttta agaggtatca catggatcat catcggtacc ttggagctga    360

tggcgtcgat gtagatattc ctaccgattt tgagggctgg ttcttctgta ccgctttcag    420

aaagtttata tgggttattc ttcagcctct cttttatgcc tttcgacctc tgttcatcaa    480

ccccaaacca attacgtatc tggaagttat caataccgtg gcacaggtca cttttgacat    540

tttaatttat tactttttgg gaattaaatc cttagtctac atgttggcag catctttact    600

tggcctgggt ttgcacccaa tttctggaca ttttatagct gagcattaca tgttcttaaa    660

gggtcatgaa acttactcat attatgggcc tctgaattta cttaccttca atgtgggtta    720

tcataatgaa catcatgatt tccccaacat tcctggaaaa agtcttccac tggtgaggaa    780

aatagcagct gaatactatg acaacctccc tcactacaat tcctggataa aagtactgta    840

tgattttgtg atggatgata caataagtcc ctactcaaga atgaagaggc accaaaaagg    900

agagatggtg ctggagtaaa tatcattagt gccaaaggga ttcttctcca aaactttaga    960

tgataaaatg gaatttttgc attattaaac ttgagaccag tgatgctcag aagctcccct   1020
```

```
ggcacaattt cagagtaaga gctcggtgat accaagaagt gaatctggct tttaaacagt   1080

cagcctgact ctgtactgct cagtttcact cacaggaaac ttgtgacttg tgtattatcg   1140

tcattgagga tgtttcactc atgtctgtca ttttataagc atatcattta aaaagcttct   1200

aaaaagctat ttcgccagg                                                1219


<210> SEQ ID NO 28
<211> LENGTH: 655
<212> TYPE: DNA
<213> ORGANISM: Homo sapiens

<400> SEQUENCE: 28

ttaccttcta cgtccgcttc ttcctcactt atgtgccact attggggctg aaagcttcct     60

gggccttttc ttcatagtca ggttcctgga aagcaactgg tttgtgtggg tgacacagat    120

gaaccatatt cccatgcaca ttgatcatga ccggaacatg gactgggttt ccacccagct    180

ccaggccaca tgcaatgtcc acaagtctgc cttcaatgac tggttcagtg gacacctcaa    240

cttccagatt gagcaccatc tttttcccac gatgcctcga cacaattacc acaaagtggc    300

tcccctggtg cagtccttgt gtgccaagca tggcatagag taccagtcca agcccctgct    360

gtcagccttc gccgacatca tccactcact aaaggagtca gggcagctct ggctagatgc    420

ctatcttcac caataacaac agccaccctg cccagtctgg aagaagagga ggaagactct    480

ggagccaagg cagaggggag cttgagggac aatgccacta tagtttaata ctcagagggg    540

gttgggtttg gggacataaa gcctctgact caaactcctc ccttttatct tctagccaca    600

gttctaagac ccaaagtggg gggtggacac agaagtccct aggagggaag gagct         655


<210> SEQ ID NO 29
<211> LENGTH: 304
<212> TYPE: DNA
<213> ORGANISM: Homo sapiens

<400> SEQUENCE: 29

gtcttttact ttggcaatgg ctggattcct accctcatca cggcctttgt ccttgctacc     60

tctcaggccc aagctggatg gctgcaacat gattatggcc acctgtctgt ctacagaaaa    120

cccaagtgga accaccttgt ccacaaattc gtcattggcc acttaaaggg tgcctctgcc    180

aactggtgga atcatcgcca cttccagcac cacgccaagc ctaacatctt ccacaaggat    240

cccgatgtga acatgctgca cgtgtttgtt ctgggcgaat ggcagcccat cgagtacggc    300

aaga                                                                 304


<210> SEQ ID NO 30
<211> LENGTH: 918
<212> TYPE: DNA
<213> ORGANISM: Homo sapiens

<400> SEQUENCE: 30

cagggaccta ccccgcgcta cttcacctgg gacgaggtgg cccagcgctc agggtgcgag     60

gagcggtggc tagtgatcga ccgtaaggtg tacaacatca gcgagttcac ccgccggcat    120

ccagggggct cccgggtcat cagccactac gccgggcagg atgccacgga tccctttgtg    180

gccttccaca tcaacaaggg ccttgtgaag aagtatatga actctctcct gattggagaa    240

ctgtctccag agcagcccag ctttgagccc accaagaata aagagctgac agatgagttc    300

cgggagctgc gggccacagt ggagcggatg gggctcatga aggccaacca tgtcttcttc    360

ctgctgtacc tgctgcacat cttgctgctg gatggtgcag cctggctcac cctttgggtc    420
```

```
tttgggacgt ccttttttgcc cttcctcctc tgtgcggtgc tgctcagtgc agttcaggcc    480

caggctggct ggctgcagca tgactttggg cacctgtcgg tcttcagcac ctcaaagtgg    540

aaccatctgc tacatcattt tgtgattggc cacctgaagg gggcccccgc cagttggtgg    600

aaccacatgc acttccagca ccatgccaag cccaactgct tccgcaaaga cccagacatc    660

aacatgcatc ccttcttctt tgccttgggg aagatcctct ctgtggagct tgggaaacag    720

aagaaaaaat atatgccgta caaccaccag cacaratact tcttcctaat tgggccccca    780

gccttgctgc ctctctactt ccagtggtat attttctatt ttgttatcca gcgaaagaag    840

tgggtggact tggcctggat cagcaaacag gaatacgatg aagccgggct tccattgtcc    900

accgcaaatg cttctaaa                                                   918
```

<210> SEQ ID NO 31
<211> LENGTH: 1686
<212> TYPE: DNA
<213> ORGANISM: Homo sapiens

<400> SEQUENCE: 31

```
gccacttaaa gggtgcctct gccaactggt ggaatcatcg ccacttccag caccacgcca     60

agcctaacat cttccacaag gatcccgatg tgaacatgct gcacgtgttt gttctgggcg    120

aatggcagcc catcgagtac ggcaagaaga agctgaaata cctgccctac aatcaccagc    180

acgaatactt cttcctgatt gggccgccgc tgctcatccc catgtatttc cagtaccaga    240

tcatcatgac catgatcgtc cataagaact gggtggacct ggcctgggcc gtcagctact    300

acatccggtt cttcatcacc tacatccctt tctacggcat cctgggagcc ctccttttcc    360

tcaacttcat caggttcctg gagagccact ggtttgtgtg ggtcacacag atgaatcaca    420

tcgtcatgga gattgaccag gaggcctacc gtgactggtt cagtagccag ctgacagcca    480

cctgcaacgt ggagcagtcc ttcttcaacg actggttcag tggacacctt aacttccaga    540

ttgagcacca cctcttcccc accatgcccc ggcacaactt acacaagatc gccccgctgg    600

tgaagtctct atgtgccaag catggcattg aataccagga gaagccgcta ctgagggccc    660

tgctggacat catcaggtcc ctgaagaagt ctgggaagct gtggctggac gcctaccttc    720

acaaatgaag ccacagcccc cgggacaccg tggggaaggg gtgcaggtgg ggtgatggcc    780

agaggaatga tgggcttttg ttctgagggg tgtccgagag gctggtgtat gcactgctca    840

cggaccccat gttggatctt tctccctttc tcctctcctt tttctcttca catctccccc    900

atagcaccct gccctcatgg gacctgccct ccctcagccg tcagccatca gccatggccc    960

tcccagtgcc tcctagcccc ttcttccaag gagcagagag gtggccaccg ggggtggctc   1020

tgtcctacct ccactctctg cccctaaaga tgggaggaga ccagcggtcc atgggtctgg   1080

cctgtgagtc tccccttgca gcctggtcac taggcatcac ccccgctttg gttcttcaga   1140

tgctcttggg gttcataggg gcaggtccta gtcgggcagg gcccctgacc ctcccggcct   1200

ggcttcactc tccctgacgg ctgccattgg tccacccttt catagagagg cctgctttgt   1260

tacaaagctc gggtctccct cctgcagctc ggttaagtac ccgaggcctc tcttaagatg   1320

tccagggccc caggcccgcg ggcacagcca gcccaaacct tgggccctgg aagagtcctc   1380

caccccatca ctagagtgct ctgaccctgg gctttcacgg gccccattcc accgcctccc   1440

caacttgagc ctgtgacctt gggaccaaag gggggagtccc tcgtctcttg tgactcagca   1500

gaggcagtgg ccacgttcag ggagggggccg gctggcctgg aggctcagcc caccctccag   1560

cttttcctca gggtgtcctg aggtccaaga ttctggagca atctgaccct tctccaaagg   1620
```

```
ctctgttatc agctgggcag tgccagccaa tccctggcca tttggcccca ggggacgtgg   1680

gccctg                                                              1686
```

<210> SEQ ID NO 32
<211> LENGTH: 1843
<212> TYPE: DNA
<213> ORGANISM: Homo sapiens

<400> SEQUENCE: 32

```
gtcttttact ttggcaatgg ctggattcct accctcatca cggcctttgt ccttgctacc     60

tctcaggccc aagctggatg gctgcaacat gattatggcc acctgtctgt ctacagaaaa    120

cccaagtgga accaccttgt ccacaaattc gtcattggcc acttaaaggg tgcctctgcc    180

aactggtgga atcatcgcca cttccagcac cacgccaagc ctaacatctt ccacaaggat    240

cccgatgtga acatgctgca cgtgtttgtt ctgggcgaat ggcagcccat cgagtacggc    300

aagaagaagc tgaaatacct gccctacaat caccagcacg aatacttctt cctgattggg    360

ccgccgctgc tcatccccat gtatttccag taccagatca tcatgaccat gatcgtccat    420

aagaactggg tggacctggc ctgggccgtc agctactaca tccggttctt catcacctac    480

atccctttct acggcatcct gggagccctc cttttcctca acttcatcag gttcctggag    540

agccactggt ttgtgtgggt cacacagatg aatcacatcg tcatggagat tgaccaggag    600

gcctaccgtg actggttcag tagccagctg acagccacct gcaacgtgga gcagtccttc    660

ttcaacgact ggttcagtgg acaccttaac ttccagattg agcaccacct cttccccacc    720

atgccccggc acaacttaca caagatcgcc ccgctggtga agtctctatg tgccaagcat    780

ggcattgaat accaggagaa gccgctactg agggccctgc tggacatcat caggtccctg    840

aagaagtctg ggaagctgtg gctggacgcc taccttcaca aatgaagcca cagcccccgg    900

gacaccgtgg ggaaggggtg caggtggggt gatggccaga ggaatgatgg gcttttgttc    960

tgaggggtgt ccgagaggct ggtgtatgca ctgctcacgg accccatgtt ggatctttct   1020

ccctttctcc tctccttttt ctcttcacat ctcccccata gcaccctgcc ctcatgggac   1080

ctgccctccc tcagccgtca gccatcagcc atggccctcc cagtgcctcc tagccccttc   1140

ttccaaggag cagagaggtg gccaccgggg gtggctctgt cctacctcca ctctctgccc   1200

ctaaagatgg gaggagacca gcggtccatg ggtctggcct gtgagtctcc ccttgcagcc   1260

tggtcactag gcatcacccc cgctttggtt cttcagatgc tcttggggtt cataggggca   1320

ggtcctagtc gggcagggcc cctgaccctc ccggcctggc ttcactctcc ctgacggctg   1380

ccattggtcc accctttcat agagaggcct gctttgttac aaagctcggg tctccctcct   1440

gcagctcggt taagtacccg aggcctctct taagatgtcc agggccccag gcccgcgggc   1500

acagccagcc caaaccttgg gccctggaag agtcctccac cccatcacta gagtgctctg   1560

accctgggct ttcacgggcc ccattccacc gcctccccaa cttgagcctg tgaccttggg   1620

accaaagggg gagtccctcg tctcttgtga ctcagcagag gcagtggcca cgttcaggga   1680

ggggccggct ggcctggagg ctcagcccac cctccagctt ttcctcaggg tgtcctgagg   1740

tccaagattc tggagcaatc tgacccttct ccaaaggctc tgttatcagc tgggcagtgc   1800

cagccaatcc ctggccattt ggccccaggg gacgtgggcc ctg                     1843
```

<210> SEQ ID NO 33
<211> LENGTH: 2257
<212> TYPE: DNA
<213> ORGANISM: Homo sapiens

<400> SEQUENCE: 33

```
cagggaccta ccccgcgcta cttcacctgg gacgaggtgg cccagcgctc agggtgcgag     60
gagcggtggc tagtgatcga ccgtaaggtg tacaacatca gcgagttcac ccgccggcat    120
ccagggggct cccgggtcat cagccactac gccgggcagg atgccacgga tccctttgtg    180
gccttccaca tcaacaaggg ccttgtgaag aagtatatga actctctcct gattggagaa    240
ctgtctccag agcagcccag ctttgagccc accaagaata aagagctgac agatgagttc    300
cgggagctgc gggccacagt ggagcggatg ggctcatga aggccaacca tgtcttcttc    360
ctgctgtacc tgctgcacat cttgctgctg gatggtgcag cctggctcac cctttgggtc    420
tttgggacgt cctttttgcc cttcctcctc tgtgcggtgc tgctcagtgc agttcagcag    480
gcccaagctg gatggctgca acatgattat ggccacctgt ctgtctacag aaaacccaag    540
tggaaccacc ttgtccacaa attcgtcatt ggccacttaa agggtgcctc tgccaactgg    600
tggaatcatc gccacttcca gcaccacgcc aagcctaaca tcttccacaa ggatcccgat    660
gtgaacatgc tgcacgtgtt tgttctgggc gaatggcagc ccatcgagta cggcaagaag    720
aagctgaaat acctgcccta caatcaccag cacgaatact tcttcctgat tgggccgccg    780
ctgctcatcc ccatgtattt ccagtaccag atcatcatga ccatgatcgt ccataagaac    840
tgggtggacc tggcctgggc cgtcagctac tacatccggt tcttcatcac ctacatccct    900
ttctacggca tcctgggagc cctccttttc ctcaacttca tcaggttcct ggagagccac    960
tggtttgtgt gggtcacaca gatgaatcac atcgtcatgg agattgacca ggaggcctac   1020
cgtgactggt tcagtagcca gctgacagcc acctgcaacg tggagcagtc cttcttcaac   1080
gactggttca gtggacacct taacttccag attgagcacc acctcttccc caccatgccc   1140
cggcacaact tacacaagat cgccccgctg gtgaagtctc tatgtgccaa gcatggcatt   1200
gaataccagg agaagccgct actgagggcc ctgctggaca tcatcaggtc cctgaagaag   1260
tctgggaagc tgtggctgga cgcctacctt cacaaatgaa gccacagccc ccgggacacc   1320
gtggggaagg ggtgcaggtg gggtgatggc cagaggaatg atgggctttt gttctgaggg   1380
gtgtccgaga ggctggtgta tgcactgctc acggacccca tgttggatct ttctcccttt   1440
ctcctctcct ttttctcttc acatctcccc catagcaccc tgccctcatg ggacctgccc   1500
tccctcagcc gtcagccatc agccatggcc ctcccagtgc ctcctagccc cttcttccaa   1560
ggagcagaga ggtggccacc gggggtggct ctgtcctacc tccactctct gcccctaaag   1620
atgggaggag accagcggtc catgggtctg gcctgtgagt ctccccttgc agcctggtca   1680
ctaggcatca cccccgcttt ggttcttcag atgctcttgg ggttcatagg ggcaggtcct   1740
agtcgggcag ggcccctgac cctcccggcc tggcttcact ctccctgacg gctgccattg   1800
gtccaccctt tcatagagag gcctgctttg ttacaaagct cgggtctccc tcctgcagct   1860
cggttaagta cccgaggcct ctcttaagat gtccagggcc ccaggcccgc gggcacagcc   1920
agcccaaacc ttgggccctg gaagagtcct ccaccccatc actagagtgc tctgaccctg   1980
ggctttcacg ggccccattc caccgcctcc ccaacttgag cctgtgacct tgggaccaaa   2040
gggggagtcc ctcgtctctt gtgactcagc agaggcagtg gccacgttca gggaggggcc   2100
ggctggcctg gaggctcagc ccaccctcca gcttttcctc agggtgtcct gaggtccaag   2160
attctggagc aatctgaccc ttctccaaag gctctgttat cagctgggca gtgccagcca   2220
atccctggcc atttggcccc aggggacgtg ggccctg                            2257
```

<210> SEQ ID NO 34

```
<211> LENGTH: 406
<212> TYPE: PRT
<213> ORGANISM: Homo sapiens
<220> FEATURE:
<221> NAME/KEY: UNSURE
<222> LOCATION: (1)..(406)
<223> OTHER INFORMATION: Amino acids 306,329,331,334,358,375,and 382
      uncertain of sequence

<400> SEQUENCE: 34

His Ala Asp Arg Arg Arg Glu Ile Leu Ala Lys Tyr Pro Glu Ile Lys
1               5                   10                  15

Ser Leu Met Lys Pro Asp Pro Asn Leu Ile Trp Ile Ile Ile Met Met
            20                  25                  30

Val Leu Thr Gln Leu Gly Ala Phe Tyr Ile Val Lys Asp Leu Asp Trp
        35                  40                  45

Lys Trp Val Ile Phe Gly Ala Tyr Ala Phe Gly Ser Cys Ile Asn His
    50                  55                  60

Ser Met Thr Leu Ala Ile His Glu Ile Ala His Asn Ala Ala Phe Gly
65                  70                  75                  80

Asn Cys Lys Ala Met Trp Asn Arg Trp Phe Gly Met Phe Ala Asn Leu
                85                  90                  95

Pro Ile Gly Ile Pro Tyr Ser Ile Ser Phe Lys Arg Tyr His Met Asp
            100                 105                 110

His His Arg Tyr Leu Gly Ala Asp Gly Val Asp Val Asp Ile Pro Thr
        115                 120                 125

Asp Phe Glu Gly Trp Phe Phe Cys Thr Ala Phe Arg Lys Phe Ile Trp
    130                 135                 140

Val Ile Leu Gln Pro Leu Phe Tyr Ala Phe Arg Pro Leu Phe Ile Asn
145                 150                 155                 160

Pro Lys Pro Ile Thr Tyr Leu Glu Val Ile Asn Thr Val Ala Gln Val
                165                 170                 175

Thr Phe Asp Ile Leu Ile Tyr Tyr Phe Leu Gly Ile Lys Ser Leu Val
            180                 185                 190

Tyr Met Leu Ala Ala Ser Leu Leu Gly Leu Gly Leu His Pro Ile Ser
        195                 200                 205

Gly His Phe Ile Ala Glu His Tyr Met Phe Leu Lys Gly His Glu Thr
    210                 215                 220

Tyr Ser Tyr Tyr Gly Pro Leu Asn Leu Leu Thr Phe Asn Val Gly Tyr
225                 230                 235                 240

His Asn Glu His His Asp Phe Pro Asn Ile Pro Gly Lys Ser Leu Pro
                245                 250                 255

Leu Val Arg Lys Ile Ala Ala Glu Tyr Tyr Asp Asn Leu Pro His Tyr
            260                 265                 270

Asn Ser Trp Ile Lys Val Leu Tyr Asp Phe Val Met Asp Asp Thr Ile
        275                 280                 285

Ser Pro Tyr Ser Arg Met Lys Arg His Gln Lys Gly Glu Met Val Leu
    290                 295                 300

Glu Xaa Ile Ser Leu Val Pro Lys Gly Phe Phe Ser Lys Thr Leu Asp
305                 310                 315                 320

Asp Lys Met Glu Phe Leu His Tyr Xaa Thr Xaa Asp Gln Xaa Cys Ser
                325                 330                 335

Glu Ala Pro Leu Ala Gln Phe Gln Ser Lys Ser Ser Val Ile Pro Arg
            340                 345                 350

Ser Glu Ser Gly Phe Xaa Thr Val Ser Leu Thr Leu Tyr Cys Ser Val
        355                 360                 365
```

```
Ser Leu Thr Gly Asn Leu Xaa Leu Val Tyr Tyr Arg His Xaa Gly Cys
    370                 375                 380

Phe Thr His Val Cys His Phe Ile Ser Ile Ser Phe Lys Lys Leu Leu
385                 390                 395                 400

Lys Ser Tyr Phe Ala Arg
                405


<210> SEQ ID NO 35
<211> LENGTH: 218
<212> TYPE: PRT
<213> ORGANISM: Homo sapiens
<220> FEATURE:
<221> NAME/KEY: UNSURE
<222> LOCATION: (1)..(218)
<223> OTHER INFORMATION: Amino acids 145,168,174,186,189,198, and 202
      uncertain of sequence

<400> SEQUENCE: 35

Tyr Leu Leu Arg Pro Leu Leu Pro His Leu Cys Ala Thr Ile Gly Ala
1               5                   10                  15

Glu Ser Phe Leu Gly Leu Phe Phe Ile Val Arg Phe Leu Glu Ser Asn
            20                  25                  30

Trp Phe Val Trp Val Thr Gln Met Asn His Ile Pro Met His Ile Asp
        35                  40                  45

His Asp Arg Asn Met Asp Trp Val Ser Thr Gln Leu Gln Ala Thr Cys
    50                  55                  60

Asn Val His Lys Ser Ala Phe Asn Asp Trp Phe Ser Gly His Leu Asn
65                  70                  75                  80

Phe Gln Ile Glu His His Leu Phe Pro Thr Met Pro Arg His Asn Tyr
                85                  90                  95

His Lys Val Ala Pro Leu Val Gln Ser Leu Cys Ala Lys His Gly Ile
            100                 105                 110

Glu Tyr Gln Ser Lys Pro Leu Leu Ser Ala Phe Ala Asp Ile Ile His
        115                 120                 125

Ser Leu Lys Glu Ser Gly Gln Leu Trp Leu Asp Ala Tyr Leu His Gln
    130                 135                 140

Xaa Gln Gln Pro Pro Cys Pro Val Trp Lys Lys Arg Arg Lys Thr Leu
145                 150                 155                 160

Glu Pro Arg Gln Arg Gly Ala Xaa Gly Thr Met Pro Leu Xaa Phe Asn
                165                 170                 175

Thr Gln Arg Gly Leu Gly Leu Gly Thr Xaa Ser Leu Xaa Leu Lys Leu
            180                 185                 190

Leu Pro Phe Ile Phe Xaa Pro Gln Phe Xaa Asp Pro Lys Trp Gly Val
        195                 200                 205

Asp Thr Glu Val Pro Arg Arg Glu Gly Ala
    210                 215


<210> SEQ ID NO 36
<211> LENGTH: 87
<212> TYPE: PRT
<213> ORGANISM: Homo sapiens
<220> FEATURE:
<221> NAME/KEY: UNSURE
<222> LOCATION: (1)..(87)
<223> OTHER INFORMATION: Amino acid 87 uncertain of sequence

<400> SEQUENCE: 36

Val Phe Tyr Phe Gly Asn Gly Trp Ile Pro Thr Leu Ile Thr Ala Phe
1               5                   10                  15

Val Leu Ala Thr Ser Gln Ala Gln Ala Gly Trp Leu Gln His Asp Tyr
```

```
            20                  25                  30

Gly His Leu Ser Val Tyr Arg Lys Pro Lys Trp Asn His Leu Val His
        35                  40                  45

Lys Phe Val Ile Gly His Leu Lys Gly Ala Ser Ala Asn Trp Trp Asn
    50                  55                  60

His Arg His Phe Gln His His Ala Lys Pro Asn Leu Gly Glu Trp Gln
65                  70                  75                  80

Pro Ile Glu Tyr Gly Lys Xaa
                85


<210> SEQ ID NO 37
<211> LENGTH: 306
<212> TYPE: PRT
<213> ORGANISM: Homo sapiens
<220> FEATURE:
<221> NAME/KEY: UNSURE
<222> LOCATION: (1)..(306)
<223> OTHER INFORMATION: Amino acid 252 uncertain of sequence

<400> SEQUENCE: 37

Gln Gly Pro Thr Pro Arg Tyr Phe Thr Trp Asp Glu Val Ala Gln Arg
1               5                   10                  15

Ser Gly Cys Glu Glu Arg Trp Leu Val Ile Asp Arg Lys Val Tyr Asn
            20                  25                  30

Ile Ser Glu Phe Thr Arg Arg His Pro Gly Gly Ser Arg Val Ile Ser
        35                  40                  45

His Tyr Ala Gly Gln Asp Ala Thr Asp Pro Phe Val Ala Phe His Ile
    50                  55                  60

Asn Lys Gly Leu Val Lys Lys Tyr Met Asn Ser Leu Leu Ile Gly Glu
65                  70                  75                  80

Leu Ser Pro Glu Gln Pro Ser Phe Glu Pro Thr Lys Asn Lys Glu Leu
                85                  90                  95

Thr Asp Glu Phe Arg Glu Leu Arg Ala Thr Val Glu Arg Met Gly Leu
            100                 105                 110

Met Lys Ala Asn His Val Phe Phe Leu Leu Tyr Leu Leu His Ile Leu
        115                 120                 125

Leu Leu Asp Gly Ala Ala Trp Leu Thr Leu Trp Val Phe Gly Thr Ser
    130                 135                 140

Phe Leu Pro Phe Leu Leu Cys Ala Val Leu Leu Ser Ala Val Gln Ala
145                 150                 155                 160

Gln Ala Gly Trp Leu Gln His Asp Phe Gly His Leu Ser Val Phe Ser
                165                 170                 175

Thr Ser Lys Trp Asn His Leu Leu His His Phe Val Ile Gly His Leu
            180                 185                 190

Lys Gly Ala Pro Ala Ser Trp Trp Asn His Met His Phe Gln His His
        195                 200                 205

Ala Lys Pro Asn Cys Phe Arg Lys Asp Pro Asp Ile Asn Met His Pro
    210                 215                 220

Phe Phe Phe Ala Leu Gly Lys Ile Leu Ser Val Glu Leu Gly Lys Gln
225                 230                 235                 240

Lys Lys Lys Tyr Met Pro Tyr Asn His Gln His Xaa Tyr Phe Phe Leu
                245                 250                 255

Ile Gly Pro Pro Ala Leu Leu Pro Leu Tyr Phe Gln Trp Tyr Ile Phe
            260                 265                 270

Tyr Phe Val Ile Gln Arg Lys Lys Trp Val Asp Leu Ala Trp Ile Ser
        275                 280                 285
```

```
Lys Gln Glu Tyr Asp Glu Ala Gly Leu Pro Leu Ser Thr Ala Asn Ala
    290                 295                 300

Ser Lys
305


<210> SEQ ID NO 38
<211> LENGTH: 562
<212> TYPE: PRT
<213> ORGANISM: Homo sapiens
<220> FEATURE:
<221> NAME/KEY: UNSURE
<222> LOCATION: (1)..(562)
<223> OTHER INFORMATION: Amino acids 242,268,405,438,464,482,497, and
      562 uncertain of sequence

<400> SEQUENCE: 38

His Leu Lys Gly Ala Ser Ala Asn Trp Trp Asn His Arg His Phe Gln
1               5                   10                  15

His His Ala Lys Pro Asn Ile Phe His Lys Asp Pro Asp Val Asn Met
            20                  25                  30

Leu His Val Phe Val Leu Gly Glu Trp Gln Pro Ile Glu Tyr Gly Lys
        35                  40                  45

Lys Lys Leu Lys Tyr Leu Pro Tyr Asn His Gln His Glu Tyr Phe Phe
    50                  55                  60

Leu Ile Gly Pro Pro Leu Leu Ile Pro Met Tyr Phe Gln Tyr Gln Ile
65                  70                  75                  80

Ile Met Thr Met Ile Val His Lys Asn Trp Val Asp Leu Ala Trp Ala
                85                  90                  95

Val Ser Tyr Tyr Ile Arg Phe Phe Ile Thr Tyr Ile Pro Phe Tyr Gly
            100                 105                 110

Ile Leu Gly Ala Leu Leu Phe Leu Asn Phe Ile Arg Phe Leu Glu Ser
        115                 120                 125

His Trp Phe Val Trp Val Thr Gln Met Asn His Ile Val Met Glu Ile
    130                 135                 140

Asp Gln Glu Ala Tyr Arg Asp Trp Phe Ser Ser Gln Leu Thr Ala Thr
145                 150                 155                 160

Cys Asn Val Glu Gln Ser Phe Phe Asn Asp Trp Phe Ser Gly His Leu
                165                 170                 175

Asn Phe Gln Ile Glu His His Leu Phe Pro Thr Met Pro Arg His Asn
            180                 185                 190

Leu His Lys Ile Ala Pro Leu Val Lys Ser Leu Cys Ala Lys His Gly
        195                 200                 205

Ile Glu Tyr Gln Glu Lys Pro Leu Leu Arg Ala Leu Leu Asp Ile Ile
    210                 215                 220

Arg Ser Leu Lys Lys Ser Gly Lys Leu Trp Leu Asp Ala Tyr Leu His
225                 230                 235                 240

Lys Xaa Ser His Ser Pro Arg Asp Thr Val Gly Lys Gly Cys Arg Trp
                245                 250                 255

Gly Asp Gly Gln Arg Asn Asp Gly Leu Leu Phe Xaa Gly Val Ser Glu
            260                 265                 270

Arg Leu Val Tyr Ala Leu Leu Thr Asp Pro Met Leu Asp Leu Ser Pro
        275                 280                 285

Phe Leu Leu Ser Phe Phe Ser Ser His Leu Pro His Ser Thr Leu Pro
    290                 295                 300

Ser Trp Asp Leu Pro Ser Leu Ser Arg Gln Pro Ser Ala Met Ala Leu
305                 310                 315                 320

Pro Val Pro Pro Ser Pro Phe Phe Gln Gly Ala Glu Arg Trp Pro Pro
```

```
                325                 330                 335

Gly Val Ala Leu Ser Tyr Leu His Ser Leu Pro Leu Lys Met Gly Gly
            340                 345                 350

Asp Gln Arg Ser Met Gly Leu Ala Cys Glu Ser Pro Leu Ala Ala Trp
        355                 360                 365

Ser Leu Gly Ile Thr Pro Ala Leu Val Leu Gln Met Leu Leu Gly Phe
    370                 375                 380

Ile Gly Ala Gly Pro Ser Arg Ala Gly Pro Leu Thr Leu Pro Ala Trp
385                 390                 395                 400

Leu His Ser Pro Xaa Arg Leu Pro Leu Val His Pro Phe Ile Glu Arg
                405                 410                 415

Pro Ala Leu Leu Gln Ser Ser Gly Leu Pro Pro Ala Ala Arg Leu Ser
            420                 425                 430

Thr Arg Gly Leu Ser Xaa Asp Val Gln Gly Pro Arg Pro Ala Gly Thr
        435                 440                 445

Ala Ser Pro Asn Leu Gly Pro Trp Lys Ser Pro Pro Pro His His Xaa
    450                 455                 460

Ser Ala Leu Thr Leu Gly Phe His Gly Pro His Ser Thr Ala Ser Pro
465                 470                 475                 480

Thr Xaa Ala Cys Asp Leu Gly Thr Lys Gly Gly Val Pro Arg Leu Leu
                485                 490                 495

Xaa Leu Ser Arg Gly Ser Gly His Val Gln Gly Gly Ala Gly Trp Pro
            500                 505                 510

Gly Gly Ser Ala His Pro Pro Ala Phe Pro Gln Gly Val Leu Arg Ser
        515                 520                 525

Lys Ile Leu Glu Gln Ser Asp Pro Ser Pro Lys Ala Leu Leu Ser Ala
    530                 535                 540

Gly Gln Cys Gln Pro Ile Pro Gly His Leu Ala Pro Gly Asp Val Gly
545                 550                 555                 560

Pro Xaa


<210> SEQ ID NO 39
<211> LENGTH: 615
<212> TYPE: PRT
<213> ORGANISM: Homo sapiens
<220> FEATURE:
<221> NAME/KEY: UNSURE
<222> LOCATION: (1)..(615)
<223> OTHER INFORMATION: Amino acids 295,321,458,491,517,535,550, and
      615 uncertain of sequence

<400> SEQUENCE: 39

Val Phe Tyr Phe Gly Asn Gly Trp Ile Pro Thr Leu Ile Thr Ala Phe
1               5                   10                  15

Val Leu Ala Thr Ser Gln Ala Gln Ala Gly Trp Leu Gln His Asp Tyr
            20                  25                  30

Gly His Leu Ser Val Tyr Arg Lys Pro Lys Trp Asn His Leu Val His
        35                  40                  45

Lys Phe Val Ile Gly His Leu Lys Gly Ala Ser Ala Asn Trp Trp Asn
    50                  55                  60

His Arg His Phe Gln His His Ala Lys Pro Asn Ile Phe His Lys Asp
65                  70                  75                  80

Pro Asp Val Asn Met Leu His Val Phe Val Leu Gly Glu Trp Gln Pro
                85                  90                  95

Ile Glu Tyr Gly Lys Lys Lys Leu Lys Tyr Leu Pro Tyr Asn His Gln
            100                 105                 110
```

```
His Glu Tyr Phe Phe Leu Ile Gly Pro Pro Leu Leu Ile Pro Met Tyr
        115                 120                 125

Phe Gln Tyr Gln Ile Ile Met Thr Met Ile Val His Lys Asn Trp Val
    130                 135                 140

Asp Leu Ala Trp Ala Val Ser Tyr Tyr Ile Arg Phe Phe Ile Thr Tyr
145                 150                 155                 160

Ile Pro Phe Tyr Gly Ile Leu Gly Ala Leu Leu Phe Leu Asn Phe Ile
                165                 170                 175

Arg Phe Leu Glu Ser His Trp Phe Val Trp Val Thr Gln Met Asn His
            180                 185                 190

Ile Val Met Glu Ile Asp Gln Glu Ala Tyr Arg Asp Trp Phe Ser Ser
        195                 200                 205

Gln Leu Thr Ala Thr Cys Asn Val Glu Gln Ser Phe Phe Asn Asp Trp
    210                 215                 220

Phe Ser Gly His Leu Asn Phe Gln Ile Glu His His Leu Phe Pro Thr
225                 230                 235                 240

Met Pro Arg His Asn Leu His Lys Ile Ala Pro Leu Val Lys Ser Leu
                245                 250                 255

Cys Ala Lys His Gly Ile Glu Tyr Gln Glu Lys Pro Leu Leu Arg Ala
            260                 265                 270

Leu Leu Asp Ile Ile Arg Ser Leu Lys Lys Ser Gly Lys Leu Trp Leu
        275                 280                 285

Asp Ala Tyr Leu His Lys Xaa Ser His Ser Pro Arg Asp Thr Val Gly
    290                 295                 300

Lys Gly Cys Arg Trp Gly Asp Gly Gln Arg Asn Asp Gly Leu Leu Phe
305                 310                 315                 320

Xaa Gly Val Ser Glu Arg Leu Val Tyr Ala Leu Leu Thr Asp Pro Met
                325                 330                 335

Leu Asp Leu Ser Pro Phe Leu Leu Ser Phe Phe Ser Ser His Leu Pro
            340                 345                 350

His Ser Thr Leu Pro Ser Trp Asp Leu Pro Ser Leu Ser Arg Gln Pro
        355                 360                 365

Ser Ala Met Ala Leu Pro Val Pro Pro Ser Pro Phe Phe Gln Gly Ala
    370                 375                 380

Glu Arg Trp Pro Pro Gly Val Ala Leu Ser Tyr Leu His Ser Leu Pro
385                 390                 395                 400

Leu Lys Met Gly Gly Asp Gln Arg Ser Met Gly Leu Ala Cys Glu Ser
                405                 410                 415

Pro Leu Ala Ala Trp Ser Leu Gly Ile Thr Pro Ala Leu Val Leu Gln
            420                 425                 430

Met Leu Leu Gly Phe Ile Gly Ala Gly Pro Ser Arg Ala Gly Pro Leu
        435                 440                 445

Thr Leu Pro Ala Trp Leu His Ser Pro Xaa Arg Leu Pro Leu Val His
    450                 455                 460

Pro Phe Ile Glu Arg Pro Ala Leu Leu Gln Ser Ser Gly Leu Pro Pro
465                 470                 475                 480

Ala Ala Arg Leu Ser Thr Arg Gly Leu Ser Xaa Asp Val Gln Gly Pro
                485                 490                 495

Arg Pro Ala Gly Thr Ala Ser Pro Asn Leu Gly Pro Trp Lys Ser Pro
            500                 505                 510

Pro Pro His His Xaa Ser Ala Leu Thr Leu Gly Phe His Gly Pro His
        515                 520                 525

Ser Thr Ala Ser Pro Thr Xaa Ala Cys Asp Leu Gly Thr Lys Gly Gly
    530                 535                 540
```

```
Val Pro Arg Leu Leu Xaa Leu Ser Arg Gly Ser Gly His Val Gln Gly
545                 550                 555                 560

Gly Ala Gly Trp Pro Gly Gly Ser Ala His Pro Pro Ala Phe Pro Gln
                565                 570                 575

Gly Val Leu Arg Ser Lys Ile Leu Glu Gln Ser Asp Pro Ser Pro Lys
            580                 585                 590

Ala Leu Leu Ser Ala Gly Gln Cys Gln Pro Ile Pro Gly His Leu Ala
        595                 600                 605

Pro Gly Asp Val Gly Pro Xaa
    610                 615


<210> SEQ ID NO 40
<211> LENGTH: 753
<212> TYPE: PRT
<213> ORGANISM: Homo sapiens
<220> FEATURE:
<221> NAME/KEY: UNSURE
<222> LOCATION: (1)..(753)
<223> OTHER INFORMATION: Amino acids 433,459,596,629,655,673,688, and
      753 uncertain of sequence

<400> SEQUENCE: 40

Gln Gly Pro Thr Pro Arg Tyr Phe Thr Trp Asp Glu Val Ala Gln Arg
1               5                   10                  15

Ser Gly Cys Glu Glu Arg Trp Leu Val Ile Asp Arg Lys Val Tyr Asn
            20                  25                  30

Ile Ser Glu Phe Thr Arg Arg His Pro Gly Gly Ser Arg Val Ile Ser
        35                  40                  45

His Tyr Ala Gly Gln Asp Ala Thr Asp Pro Phe Val Ala Phe His Ile
    50                  55                  60

Asn Lys Gly Leu Val Lys Lys Tyr Met Asn Ser Leu Leu Ile Gly Glu
65                  70                  75                  80

Leu Ser Pro Glu Gln Pro Ser Phe Glu Pro Thr Lys Asn Lys Glu Leu
                85                  90                  95

Thr Asp Glu Phe Arg Glu Leu Arg Ala Thr Val Glu Arg Met Gly Leu
            100                 105                 110

Met Lys Ala Asn His Val Phe Phe Leu Leu Tyr Leu Leu His Ile Leu
        115                 120                 125

Leu Leu Asp Gly Ala Ala Trp Leu Thr Leu Trp Val Phe Gly Thr Ser
    130                 135                 140

Phe Leu Pro Phe Leu Leu Cys Ala Val Leu Leu Ser Ala Val Gln Gln
145                 150                 155                 160

Ala Gln Ala Gly Trp Leu Gln His Asp Tyr Gly His Leu Ser Val Tyr
                165                 170                 175

Arg Lys Pro Lys Trp Asn His Leu Val His Lys Phe Val Ile Gly His
            180                 185                 190

Leu Lys Gly Ala Ser Ala Asn Trp Trp Asn His Arg His Phe Gln His
        195                 200                 205

His Ala Lys Pro Asn Ile Phe His Lys Asp Pro Asp Val Asn Met Leu
    210                 215                 220

His Val Phe Val Leu Gly Glu Trp Gln Pro Ile Glu Tyr Gly Lys Lys
225                 230                 235                 240

Lys Leu Lys Tyr Leu Pro Tyr Asn His Gln His Glu Tyr Phe Phe Leu
                245                 250                 255

Ile Gly Pro Pro Leu Leu Ile Pro Met Tyr Phe Gln Tyr Gln Ile Ile
            260                 265                 270
```

```
Met Thr Met Ile Val His Lys Asn Trp Val Asp Leu Ala Trp Ala Val
        275                 280                 285

Ser Tyr Tyr Ile Arg Phe Phe Ile Thr Tyr Ile Pro Phe Tyr Gly Ile
    290                 295                 300

Leu Gly Ala Leu Leu Phe Leu Asn Phe Ile Arg Phe Leu Glu Ser His
305                 310                 315                 320

Trp Phe Val Trp Val Thr Gln Met Asn His Ile Val Met Glu Ile Asp
                325                 330                 335

Gln Glu Ala Tyr Arg Asp Trp Phe Ser Ser Gln Leu Thr Ala Thr Cys
            340                 345                 350

Asn Val Glu Gln Ser Phe Phe Asn Asp Trp Phe Ser Gly His Leu Asn
        355                 360                 365

Phe Gln Ile Glu His His Leu Phe Pro Thr Met Pro Arg His Asn Leu
    370                 375                 380

His Lys Ile Ala Pro Leu Val Lys Ser Leu Cys Ala Lys His Gly Ile
385                 390                 395                 400

Glu Tyr Gln Glu Lys Pro Leu Leu Arg Ala Leu Leu Asp Ile Ile Arg
                405                 410                 415

Ser Leu Lys Lys Ser Gly Lys Leu Trp Leu Asp Ala Tyr Leu His Lys
            420                 425                 430

Xaa Ser His Ser Pro Arg Asp Thr Val Gly Lys Gly Cys Arg Trp Gly
        435                 440                 445

Asp Gly Gln Arg Asn Asp Gly Leu Leu Phe Xaa Gly Val Ser Glu Arg
    450                 455                 460

Leu Val Tyr Ala Leu Leu Thr Asp Pro Met Leu Asp Leu Ser Pro Phe
465                 470                 475                 480

Leu Leu Ser Phe Phe Ser Ser His Leu Pro His Ser Thr Leu Pro Ser
                485                 490                 495

Trp Asp Leu Pro Ser Leu Ser Arg Gln Pro Ser Ala Met Ala Leu Pro
            500                 505                 510

Val Pro Pro Ser Pro Phe Phe Gln Gly Ala Glu Arg Trp Pro Pro Gly
        515                 520                 525

Val Ala Leu Ser Tyr Leu His Ser Leu Pro Leu Lys Met Gly Gly Asp
    530                 535                 540

Gln Arg Ser Met Gly Leu Ala Cys Glu Ser Pro Leu Ala Ala Trp Ser
545                 550                 555                 560

Leu Gly Ile Thr Pro Ala Leu Val Leu Gln Met Leu Leu Gly Phe Ile
                565                 570                 575

Gly Ala Gly Pro Ser Arg Ala Gly Pro Leu Thr Leu Pro Ala Trp Leu
            580                 585                 590

His Ser Pro Xaa Arg Leu Pro Leu Val His Pro Phe Ile Glu Arg Pro
        595                 600                 605

Ala Leu Leu Gln Ser Ser Gly Leu Pro Pro Ala Ala Arg Leu Ser Thr
    610                 615                 620

Arg Gly Leu Ser Xaa Asp Val Gln Gly Pro Arg Pro Ala Gly Thr Ala
625                 630                 635                 640

Ser Pro Asn Leu Gly Pro Trp Lys Ser Pro Pro Pro His His Xaa Ser
                645                 650                 655

Ala Leu Thr Leu Gly Phe His Gly Pro His Ser Thr Ala Ser Pro Thr
            660                 665                 670

Xaa Ala Cys Asp Leu Gly Thr Lys Gly Gly Val Pro Arg Leu Leu Xaa
        675                 680                 685

Leu Ser Arg Gly Ser Gly His Val Gln Gly Gly Ala Gly Trp Pro Gly
    690                 695                 700
```

-continued

```
Gly Ser Ala His Pro Pro Ala Phe Pro Gln Gly Val Leu Arg Ser Lys
705                 710                 715                 720

Ile Leu Glu Gln Ser Asp Pro Ser Pro Lys Ala Leu Leu Ser Ala Gly
            725                 730                 735

Gln Cys Gln Pro Ile Pro Gly His Leu Ala Pro Gly Asp Val Gly Pro
        740                 745                 750

Xaa
```

METHODS AND COMPOSITIONS FOR SYNTHESIS OF LONG CHAIN POLYUNSATURATED FATTY ACIDS

RELATED APPLICATIONS

This application is a divisional application of U.S. patent application Ser. No. 09/367,013 filed Aug. 5, 1999, which is a continuation-in-part application of U.S. patent application Ser. No. 08/834,655 filed Apr. 11, 1997, both of which are incorporated by reference in their entireties.

INTRODUCTION

1. Field of the Invention

This invention relates to modulating levels of enzymes and/or enzyme components relating to production of long chain poly-unsaturated fatty acids (PUFAs) in a microorganism or animal.

2. Background

Two main families of polyunsaturated fatty acids (PUFAs) are the ω3 fatty acids, exemplified by eicosapentaenoic acid (EPA), and the ω6 fatty acids, exemplified by arachidonic acid (ARA). PUFAs are important components of the plasma membrane of the cell, where they may be found in such forms as phospholipids. PUFAs are necessary for proper development, particularly in the developing infant brain, and for tissue formation and repair. PUFAs also serve as precursors to other molecules of importance in human beings and animals, including the prostacyclins, eicosanoids, leukotrienes and prostaglandins. Four major long chain PUFAs of importance include docosahexaenoic acid (DHA) and EPA, which are primarily found in different types of fish oil, γ-linolenic acid (GLA), which is found in the seeds of a number of plants, including evening primrose (*Oenothera biennis*), borage (*Borago officinalis*) and black currants (*Ribes nigrum*), and stearidonic acid (SDA), which is found in marine oils and plant seeds. Both GLA and another important long chain PUFA, arachidonic acid (ARA), are found in filamentous fungi. ARA can be purified from animal tissues including liver and adrenal gland. GLA, ARA, EPA and SDA are themselves, or are dietary precursors to, important long chain fatty acids involved in prostaglandin synthesis, in treatment of heart disease, and in development of brain tissue.

For DHA, a number of sources exist for commercial production including a variety of marine organisms, oils obtained from cold water marine fish, and egg yolk fractions. For ARA, microorganisms including the genera *Mortierella, Entomophthora, Phytium* and *Porphyridium* can be used for commercial production. Commercial sources of SDA include the genera *Trichodesma* and *Echium*. Commercial sources of GLA include evening primrose, black currants and borage. However, there are several disadvantages associated with commercial production of PUFAs from natural sources. Natural sources of PUFAs, such as animals and plants, tend to have highly heterogeneous oil compositions. The oils obtained from these sources therefore can require extensive purification to separate out one or more desired PUFAs or to produce an oil which is enriched in one or more PUFA. Natural sources also are subject to uncontrollable fluctuations in availability. Fish stocks may undergo natural variation or may be depleted by overfishing. Fish oils have unpleasant tastes and odors, which may be impossible to economically separate from the desired product, and can render such products unacceptable as food supplements. Animal oils, and particularly fish oils, can accumulate environmental pollutants. Weather and disease can cause fluctuation in yields from both fish and plant sources. Cropland available for production of alternate oil-producing crops is subject to competition from the steady expansion of human populations and the associated increased need for food production on the remaining arable land. Crops which do produce PUFAs, such as borage, have not been adapted to commercial growth and may not perform well in monoculture. Growth of such crops is thus not economically competitive where more profitable and better established crops can be grown. Large scale fermentation of organisms such as *Mortierella* is also expensive. Natural animal tissues contain low amounts of ARA and are difficult to process. Microorganisms such as *Porphyridium* and *Mortierella* are difficult to cultivate on a commercial scale.

Dietary supplements and pharmaceutical formulations containing PUFAs can retain the disadvantages of the PUFA source. Supplements such as fish oil capsules can contain low levels of the particular desired component and thus require large dosages. High dosages result in ingestion of high levels of undesired components, including contaminants. Unpleasant tastes and odors of the supplements can make such regimens undesirable, and may inhibit compliance by the patient. Care must be taken in providing fatty acid supplements, as overaddition may result in suppression of endogenous biosynthetic pathways and lead to competition with other necessary fatty acids in various lipid fractions in vivo, leading to undesirable results. For example, Eskimos having a diet high in ω3 fatty acids have an increased tendency to bleed (U.S. Pat. No. 4,874,603).

A number of enzymes are involved in PUFA biosynthesis. Linoleic acid (LA, 18:2 Δ9, 12) is produced from oleic acid (18:1 Δ9) by a Δ12-desaturase. GLA (18:3 Δ6, 9, 12) is produced from linoleic acid (LA, 18:2 Δ9, 12) by a Δ6-desaturase. ARA (20:4 Δ5, 8, 11, 14) production from dihomo-γ-linolenic acid (DGLA, 20:3 Δ8, 11, 14) is catalyzed by a Δ5-desaturase. However, animals cannot desaturate beyond the Δ9 position and therefore cannot convert oleic acid (18:1 Δ9) into linoleic acid (18:2 Δ9, 12). Likewise, α-linolenic acid (ALA, 18:3 Δ9, 12, 15) cannot be synthesized by mammals. Other eukaryotes, including fungi and plants, have enzymes which desaturate at positions Δ12 and Δ15. The major poly-unsaturated fatty acids of animals therefore are either derived from diet and/or from desaturation and elongation of linoleic acid (18:2 Δ9, 12) or ∝-linolenic acid (18:3 Δ9, 12, 15). Therefore it is of interest to obtain genetic material involved in PUFA biosynthesis from species that naturally produce these fatty acids and to express the isolated material in a microbial or animal system which can be manipulated to provide production of commercial quantities of one or more PUFAs. Thus there is a need for fatty acid desaturases, genes encoding them, and recombinant methods of producing them. A need further exists for oils containing higher relative proportions of and/or enriched in specific PUFAs. A need also exists for reliable economical methods of producing specific PUFAs.

Relevant Literature

Production of γ-linolenic acid by a Δ6-desaturase is described in U.S. Pat. No. 5,552,306. Production of 8,11-eicosadienoic acid using *Mortierella alpina* is disclosed in U.S. Pat. No. 5,376,541. Production of docosahexaenoic acid by dinoflagellates is described in U.S. Pat. No. 5,407,957. Cloning of a Δ6-palmitoyl-acyl carrier protein desaturase is described in PCT publication WO 96/13591 and U.S. Pat. No. 5,614,400. Cloning of a Δ6-desaturase from borage is described in PCT publication WO 96/21022. Cloning of Δ9-desaturases is described in the published patent applications PCT WO 91/13972, EP 0 550 162 A1, EP 0 561 569 A2, EP 0 644 263 A2, and EP 0 736 598 A1, and in U.S. Pat. No.

5,057,419. Cloning of Δ12-desaturases from various organisms is described in PCT publication WO 94/11516 and U.S. Pat. No. 5,443,974. Cloning of Δ15-desaturases from various organisms is described in PCT publication WO 93/11245. All publications and U.S. patents or applications referred to herein are hereby incorporated in their entirety by reference.

SUMMARY OF THE INVENTION

Novel compositions and methods are provided for preparation of poly-unsaturated long chain fatty acids. The compositions include nucleic acid encoding a Δ6- and Δ12-desaturase and/or polypeptides having Δ6- and/or Δ12-desaturase activity, the polypeptides, and probes isolating and detecting the same. The methods involve growing a host microorganism or animal expressing an introduced gene or genes encoding at least one desaturase, particularly a Δ6-, Δ9-, Δ12- or Δ5-desaturase. The methods also involve the use of antisense constructs or gene disruptions to decrease or eliminate the expression level of undesired desaturases. Regulation of expression of the desaturase polypeptide(s) provides for a relative increase in desired desaturated PUFAs as a result of altered concentrations of enzymes and substrates involved in PUFA biosynthesis. The invention finds use, for example, in the large scale production of GLA, DGLA, ARA, EPA, DHA and SDA.

In a preferred embodiment of the invention, an isolated nucleic acid comprising: a nucleotide sequence depicted in FIG. 3A-E (SEQ ID NO: 1) or FIG. 5A-D (SEQ ID NO: 3), a polypeptide encoded by a nucleotide sequence according FIG. 3A-E (SEQ ID NO: 1) or FIG. 5A-D (SEQ ID NO: 3), and a purified or isolated polypeptide comprising an amino acid sequence depicted in FIG. 3A-E (SEQ ID NO: 2) or FIG. 5A-D (SEQ ID NO: 4). In another embodiment of the invention, provided is an isolated nucleic acid encoding a polypeptide having an amino acid sequence depicted in FIG. 3A-E (SEQ ID NO: 2) or FIG. 5A-D (SEQ ID NO: 4).

Also provided is an isolated nucleic acid comprising a nucleotide sequence which encodes a polypeptide which desaturates a fatty acid molecule at carbon 6 or 12 from the carboxyl end, wherein said nucleotide sequence has an average A/T content of less than about 60%. In a preferred embodiment, the isolated nucleic acid is derived from a fungus, such as a fungus of the genus *Mortierella*. More preferred is a fungus of the species *Mortierella alpina.*

In another preferred embodiment of the invention, an isolated nucleic acid is provided wherein the nucleotide sequence of the nucleic acid is depicted in FIG. 3A-E (SEQ ID NO: 1) or FIG. 5A-D (SEQ ID NO: 3). The invention also provides an isolated or purified polypeptide which desaturates a fatty acid molecule at carbon 6 or 12 from the carboxyl end, wherein the polypeptide is a eukaryotic polypeptide or is derived from a eukaryotic polypeptide, where a preferred eukaryotic polypeptide is derived from a fungus.

The present invention further includes a nucleic acid sequence which hybridizes to FIG. 3A-E (SEQ ID NO: 1) or FIG. 5A-D (SEQ ID NO: 3). Preferred is an isolated nucleic acid having a nucleotide sequence with at least about 50% homology to FIG. 3A-E (SEQ ID NO: 1) or FIG. 5A-D (SEQ ID NO: 3). The invention also includes an isolated nucleic acid having a nucleotide sequence with at least about 50% homology to FIG. 3A-E (SEQ ID NO: 1) or FIG. 5A-D (SEQ ID NO: 3). In a preferred embodiment, the nucleic acid of the invention includes a nucleotide sequence which encodes an amino acid sequence depicted in FIG. 3A-D (SEQ ID NO: 2) which is selected from the group consisting of amino acid residues 50-53, 39-43, 172-176, 204-213, and 390-402.

Also provided by the present invention is a nucleic acid construct comprising a nucleotide sequence depicted in a FIG. 3A-E (SEQ ID NO: 1) or FIG. 5A-D (SEQ ID NO: 3) linked to a heterologous nucleic acid. In another embodiment, a nucleic acid construct is provided which comprises a nucleotide sequence depicted in a FIG. 3A-E (SEQ ID NO: 1) or FIG. 5A-D (SEQ ID NO: 3) operably associated with an expression control sequence functional in a host cell. The host cell is either eukaryotic or prokaryotic. Preferred eukaryotic host cells are those selected from the group consisting of a mammalian cell, an insect cell, a fungal cell, and an algae cell. Preferred mammalian cells include an avian cell, a preferred fungal cell includes a yeast cell, and a preferred algae cell is a marine algae cell. Preferred prokaryotic cells include those selected from the group consisting of a bacteria, a cyanobacteria, cells which contain a bacteriophage, and/or a virus. The DNA sequence of the recombinant host cell preferably contains a promoter which is functional in the host cell, which promoter is preferably inducible. In a more preferred embodiment, the microbial cell is a fungal cell of the genus *Mortierella*, with a more preferred fungus is of the species *Mortierella alpina.*

In addition, the present invention provides a nucleic acid construct comprising a nucleotide sequence which encodes a polypeptide comprising an amino acid sequence which corresponds to or is complementary to an amino acid sequence depicted in FIG. 3A-E (SEQ ID NO: 2) or FIG. 5A-D (SEQ ID NO: 4), wherein the nucleic acid is operably associated with an expression control sequence functional in a microbial cell, wherein the nucleotide sequence encodes a functionally active polypeptide which desaturates a fatty acid molecule at carbon 6 or carbon 12 from the carboxyl end of a fatty acid molecule. Another embodiment of the present invention is a nucleic acid construct comprising a nucleotide sequence which encodes a functionally active Δ6-desaturase having an amino acid sequence which corresponds to or is complementary to all of or a portion of an amino acid sequence depicted in a FIG. 3A-E (SEQ ID NO: 2), wherein the nucleotide sequence is operably associated with a transcription control sequence functional in a host cell.

Yet another embodiment of the present invention is a nucleic acid construct comprising a nucleotide sequence which encodes a functionally active Δ2-desaturase having an amino acid sequence which corresponds to or is complementary to all of or a portion of an amino acid sequence depicted in a FIG. 5A-D (SEQ ID NO: 4), wherein the nucleotide sequence is operably associated with a transcription control sequence functional in a host cell. The host cell, is either a eukaryotic or prokaryotic host cell. Preferred eukaryotic host cells are those selected from the group consisting of a mammalian cell, an insect cell, a fungal cell, and an algae cell. Preferred mammalian cells include an avian cell, a preferred fungal cell includes a yeast cell, and a preferred algae cell is a marine algae cell. Preferred prokaryotic cells include those selected from the group consisting of a bacteria, a cyanobacteria, cells which contain a bacteriophage, and/or a virus. The DNA sequence of the recombinant host cell preferably contains a promoter which is functional in the host cell and which preferably is inducible. A preferred recombinant host cell is a microbial cell such as a yeast cell, such as a *Saccharomyces* cell.

The present invention also provides a recombinant microbial cell comprising at least one copy of a nucleic acid which encodes a functionally active *Mortierella alpina* fatty acid desaturase having an amino acid sequence as depicted in FIG. 3A-E (SEQ ID NO: 2), wherein the cell or a parent of the cell was transformed with a vector comprising said DNA sequence, and wherein the DNA sequence is operably associated with an expression control sequence. In a preferred embodiment, the cell is a microbial cell which is enriched in 18:2 fatty acids, particularly where the microbial cell is from a genus selected from the group consisting of a prokaryotic cell and eukaryotic cell. In another preferred embodiment, the microbial cell according to the invention includes an expression control sequence which is endogenous to the microbial cell.

Also provided by the present invention is a method for production of GLA in a host cell, where the method comprises growing a host culture having a plurality of host cells which contain one or more nucleic acids encoding a polypeptide which converts LA to GLA, wherein said one or more nucleic acids is operably associated with an expression control sequence, under conditions whereby said one or more nucleic acids are expressed, whereby GLA is produced in the host cell. In several preferred embodiments of the methods, the polypeptide employed in the method is a functionally active enzyme which desaturates a fatty acid molecule at carbon 6 from the carboxyl end of a fatty acid molecule; the said one or more nucleic acids is derived from a *Mortierella alpina*; the substrate for the polypeptide is exogenously supplied; the host cells are microbial cells; the microbial cells are yeast cells, such as *Saccharomyces* cells; and the growing conditions are inducible.

Also provided is an oil comprising one or more PUFA, wherein the amount of said one or more PUFAs is approximately 0.3-30% arachidonic acid (ARA), approximately 0.2-30% dihomo-γ-linolenic acid (DGLA), and approximately 0.2-30% γ-linoleic acid (GLA). A preferred oil of the invention is one in which the ratio of ARA:DGLA:GLA is approximately 1.0:19.0:30 to 6.0:1.0:0.2. Another preferred embodiment of the invention is a pharmaceutical composition comprising the oils in a pharmaceutically acceptable carrier. Further provided is a nutritional composition comprising the oils of the invention. The nutritional compositions of the invention preferably are administered to a mammalian host parenterally or internally. A preferred composition of the invention for internal consumption is an infant formula. In a preferred embodiment, the nutritional compositions of the invention are in a liquid form or a solid form, and can be formulated in or as a dietary supplement, and the oils provided in encapsulated form. The oils of the invention can be free of particular components of other oils and can be derived from a microbial cell, such as a yeast cell.

The present invention further provides a method for desaturating a fatty acid. In a preferred embodiment the method comprises culturing a recombinant microbial cell according to the invention under conditions suitable for expression of a polypeptide encoded by said nucleic acid, wherein the host cell further comprises a fatty acid substrate of said polypeptide. Also provided is a fatty acid desaturated by such a method, and an oil composition comprising a fatty acid produced according to the methods of the invention.

The present invention further includes a purified nucleotide sequence or polypeptide sequence that is substantially related or homologous to the nucleotide and peptide sequences presented in SEQ ID NO:1-SEQ ID NO:40. The present invention is further directed to methods of using the sequences presented in SEQ ID NO:1 to SEQ ID NO:40 as probes to identify related sequences, as components of expression systems and as components of systems useful for producing transgenic oil.

The present invention is further directed to formulas, dietary supplements or dietary supplements in the form of a liquid or a solid containing the long chain fatty acids of the invention. These formulas and supplements may be administered to a human or an animal.

The formulas and supplements of the invention may further comprise at least one macronutrient selected from the group consisting of coconut oil, soy oil, canola oil, mono- and diglycerides, glucose, edible lactose, electrodialysed whey, electrodialysed skim milk, milk whey, soy protein, and other protein hydrolysates.

The formulas of the present invention may further include at least one vitamin selected from the group consisting of Vitamins A, C, D, E, and B complex; and at least one mineral selected from the group consisting of calcium, magnesium, zinc, manganese, sodium, potassium, phosphorus, copper, chloride, iodine, selenium, and iron.

The present invention is further directed to a method of treating a patient having a condition caused by insufficient intake or production of polyunsaturated fatty acids comprising administering to the patient a dietary substitute of the invention in an amount sufficient to effect treatment of the patient.

The present invention is further directed to cosmetic and pharmaceutical compositions of the material of the invention.

The present invention is further directed to transgenic oils in pharmaceutically acceptable carriers. The present invention is further directed to nutritional supplements, cosmetic agents and infant formulae containing transgenic oils.

The present invention is further directed to a method for obtaining altered long chain polyunsaturated fatty acid biosynthesis comprising the steps of: growing a microbe having cells which contain a transgene which encodes a transgene expression product which desaturates a fatty acid molecule at carbon 6 or 12 from the carboxyl end of said fatty acid molecule, wherein the transgene is operably associated with an expression control sequence, under conditions whereby the transgene is expressed, whereby long chain polyunsaturated fatty acid biosynthesis in the cells is altered.

The present invention is further directed toward pharmaceutical compositions comprising at least one nutrient selected from the group consisting of a vitamin, a mineral, a carbohydrate, a sugar, an amino acid, a free fatty acid, a phospholipid, an antioxidant, and a phenolic compound.

BRIEF DESCRIPTION OF THE DRAWINGS

FIG. 3A-E shows the DNA sequence of the *Mortierella alpina* Δ6-desaturase and the deduced amino acid sequence:

FIG. 3A-E (SEQ ID NO: 1 Δ6 DESATURASE cDNA)

FIG. 3A-E (SEQ ID NO: 2 Δ6 DESATURASE AMINO ACID)

FIG. 4 shows an alignment of a portion of the *Mortierella alpina* Δ6-desaturase amino acid sequence with other related sequences.

FIG. 5A-D shows the DNA sequence of the *Mortierella alpina* Δ12-desaturase and the deduced amino acid sequence:

FIG. 5A-D (SEQ ID NO: 3 Δ12 DESATURASE AMINO ACID)

FIG. 5A-D (SEQ ID NO: 4 Δ12 DESATURASE AMINO ACID)

FIG. 9 shows alignments of the protein sequence of the Ma 29 and contig 253538a.

FIG. 10 shows alignments of the protein sequence of Ma 524 and contig 253538a.

BRIEF DESCRIPTION OF THE SEQUENCE LISTINGS

Figure 1:
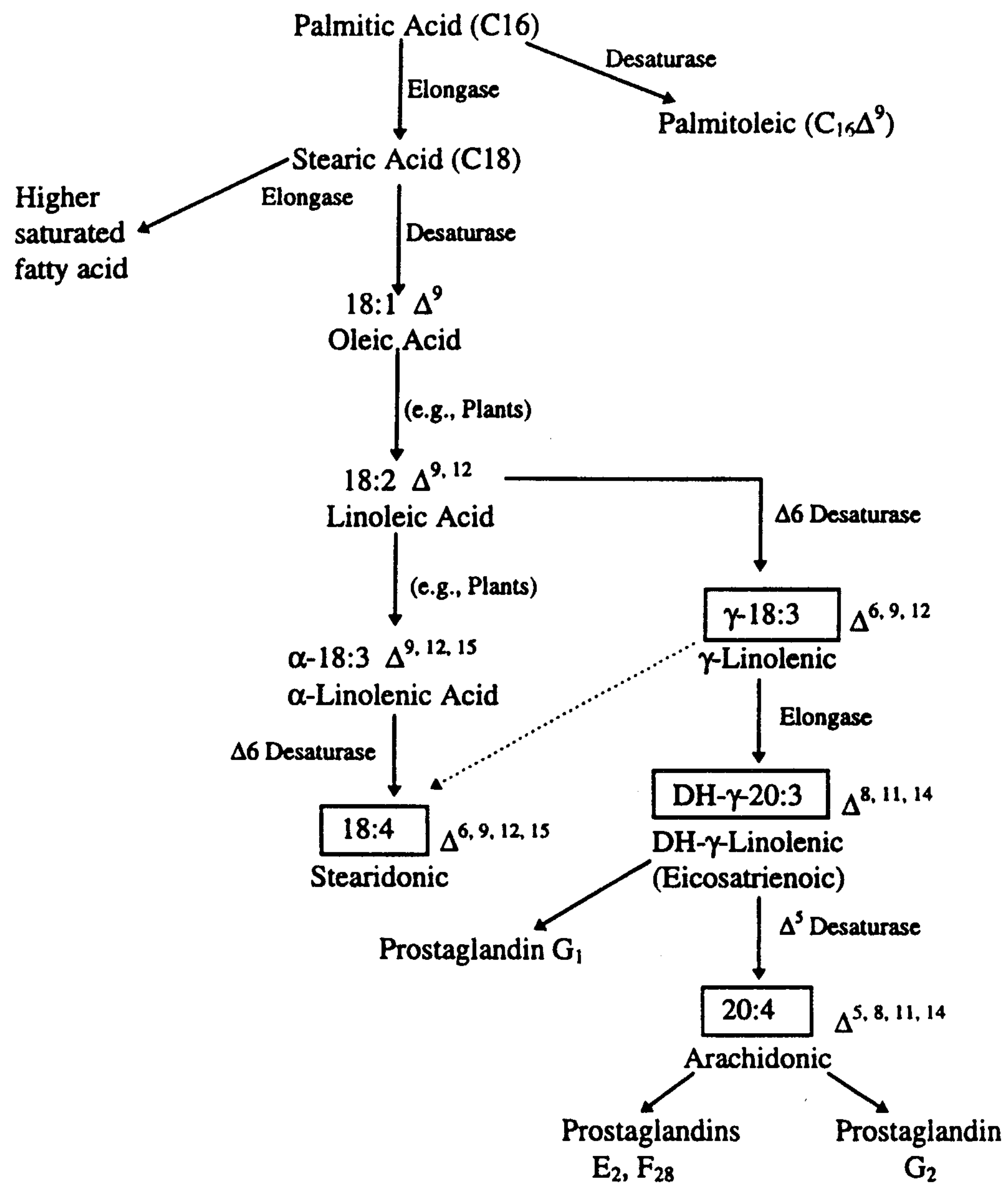
FIG. 1 shows possible pathways for the synthesis of arachidonic acid (20:4 Δ5, 8, 11, 14) and stearidonic acid (18:4 Δ6, 9, 12, 15) from palmitic acid ($C_{16}$) from a variety of organisms, including algae, *Mortierella* and humans. These PUFAs can serve as precursors to other molecules important for humans and other animals, including prostacyclins, leukotrienes, and prostaglandins, some of which are shown.

SEQ ID NO:1 shows the DNA sequence of the *Mortierella alpina* Δ6-desaturase.

SEQ ID NO:2 shows the protein sequence of the *Mortierella alpina* Δ6-desaturase.

SEQ ID NO:3 shows the DNA sequence of the *Mortierella alpina* Δ12-desaturase.

SEQ ID NO:4 shows the protein sequence of the *Mortierella alpina* Δ12-desaturase.

SEQ ID NO:5-11 show various desaturase sequences.

SEQ ID NO:13-18 show various PCR primer sequences.

SEQ ID NO:19 and SEQ ID NO:20 show the nucleotide and amino acid sequence of a *Dictyostelium discoideum* desaturase.

SEQ ID NO:21 and SEQ ID NO:22 show the nucleotide and amino acid sequence of a *Phaeodactylum tricornutum* desaturase.

SEQ ID NO:23-26 show the nucleotide and deduced amino acid sequence of a *Schizochytrium* cDNA clone.

SEQ ID NO: 27-33 show nucleotide sequences for human desaturases.

SEQ ID NO:34-SEQ ID NO:40 show peptide sequences for human desaturases.

DESCRIPTION OF THE PREFERRED EMBODIMENTS

In order to ensure a complete understanding of the invention, the following definitions are provided:

Δ5-Desaturase: Δ5 desaturase is an enzyme which introduces a double bond between carbons 5 and 6 from the carboxyl end of a fatty acid molecule.

Δ6-Desaturase: Δ6-desaturase is an enzyme which introduces a double bond between carbons 6 and 7 from the carboxyl end of a fatty acid molecule.

Δ9-Desaturase: Δ9-desaturase is an enzyme which introduces a double bond between carbons 9 and 10 from the carboxyl end of a fatty acid molecule.

Δ2-Desaturase: Δ12-desaturase is an enzyme which introduces a double bond between carbons 12 and 13 from the carboxyl end of a fatty acid molecule.

Fatty Acids: Fatty acids are a class of compounds containing a long hydrocarbon chain and a terminal carboxylate group. Fatty acids include the following:

| Fatty Acid | | |
|---|---|---|
| 12:0 | lauric acid | |
| 16:0 | palmitic acid | |
| 16:1 | palmitoleic acid | |
| 18:0 | stearic acid | |
| 18:1 | oleic acid | Δ9-18:1 |
| 18:2 Δ5, 9 | taxoleic acid | Δ5, 9-18:2 |
| 18:2 Δ6, 9 | 6,9-octadecadienoic acid | Δ6, 9-18:2 |
| 18:2 | Linolenic acid | Δ9, 12-18:2 (LA) |
| 18:3 Δ6, 9, 12 | Gamma-linolenic acid | Δ6, 9, 12-18:3 (GLA) |
| 18:3 Δ5, 9, 12 | Pinolenic acid | Δ5, 9, 12-18:3 |
| 18:3 | alpha-linoleic acid | Δ9, 12, 15-18:3 (ALA) |
| 18:4 | stearidonic acid | Δ6, 9, 12, 15-18:4 (SDA) |
| 20:0 | Arachidic acid | |
| 20:1 | Eicoscenic Acid | |
| 22:0 | behehic acid | |
| 22:1 | erucic acid | |
| 22:2 | docasadienoic acid | |
| 20:4 ω6 | arachidonic acid | Δ5, 8, 11, 14-20:4 (ARA) |
| 20:3 ω6 | ω6-eicosatrienoic dihomo-gamma linolenic | Δ8, 11, 14-20:3 (DGLA) |
| 20:5 ω3 | Eicosapentanoic (Timnodonic acid) | Δ5, 8, 11, 14, 17-20:5 (EPA) |
| 20:3 ω3 | ω3-eicosatrienoic | Δ11, 16, 17-20:3 |
| 20:4 ω3 | ω3-eicosatetraenoic | Δ8, 11, 14, 17-20:4 |
| 22:5 ω3 | Docosapentaenoic | Δ7, 10, 13, 16, 19-22:5 (ω3DPA) |
| 22:6 ω3 | Docosahexaenoic (cervonic acid) | Δ4, 7, 10, 13, 16, 19-22:6 (DHA) |
| 24:0 | Lignoceric acid | |

Taking into account these definitions, the present invention is directed to novel DNA sequences, DNA constructs, methods and compositions are provided which permit modification of the poly-unsaturated long chain fatty acid content of, for example, microbial cells or animals. Host cells are manipulated to express a sense or antisense transcript of a DNA encoding a polypeptide(s) which catalyzes the desaturation of a fatty acid. The substrate(s) for the expressed enzyme may be produced by the host cell or may be exogenously supplied. To achieve expression, the transformed DNA is operably associated with transcriptional and translational initiation and termination regulatory regions that are functional in the host cell. Constructs comprising the gene to be expressed can provide for integration into the genome of the host cell or can autonomously replicate in the host cell. For production of linoleic acid (LA), the expression cassettes generally used include a cassette which provides for Δ12-desaturase activity, particularly in a host cell which produces or can take up oleic acid (U.S. Pat. No. 5,443,974). Production of LA also can be increased by providing an expression cassette for a Δ9-desaturase where that enzymatic activity is limiting. For production of ALA, the expression cassettes generally used include a cassette which provides for Δ15- or ω3-desaturase activity, particularly in a host cell which produces or can take up LA. For production of GLA or SDA, the expression cassettes generally used include a cassette which provides for Δ6-desaturase activity, particularly in a host cell which produces or can take up LA or ALA, respectively. Production of ω6-type unsaturated fatty acids, such as LA or GLA, is favored in a host microorganism or animal which is incapable of producing ALA. The host ALA production can be removed, reduced and/or inhibited by inhibiting the activity of a Δ15- or ω3-type desaturase (see FIG. 2). This can be accomplished by standard selection, providing an expression cassette for an antisense Δ15 or ω3 transcript, by disrupting a target Δ15- or ω3-desaturase gene through insertion, deletion, substitution of part or all of the target gene, or by adding an inhibitor of Δ15- or ω3-desaturase. Similarly, production of LA or ALA is favored in a microorganism or animal having Δ6-desaturase activity by providing an expression cassette for an antisense Δ6 transcript, by disrupting a Δ6-desaturase gene, or by use of a Δ6-desaturase inhibitor.

Microbial Production of Fatty Acids

Microbial production of fatty acids has several advantages over purification from natural sources such as fish or plants. Many microbes are known with greatly simplified oil compositions compared with those of higher organisms, making purification of desired components easier. Microbial production is not subject to fluctuations caused by external variables such as weather and food supply. Microbially produced oil is substantially free of contamination by environmental pollutants. Additionally, microbes can provide PUFAs in particular forms which may have specific uses. For example, *Spirulina* can provide PUFAs predominantly at the first and third positions of triglycerides; digestion by pancreatic lipases preferentially releases fatty acids from these positions. Following human or animal ingestion of triglycerides derived from *Spirulina*, these PUFAs are released by pancreatic lipases as free fatty acids and thus are directly available, for example, for infant brain development. Additionally, microbial oil production can be manipulated by controlling culture conditions, notably by providing particular substrates for microbially expressed enzymes, or by addition of compounds which suppress undesired biochemical pathways. In addition to these advantages, production of fatty acids from recombinant microbes provides the ability to alter the naturally occurring microbial fatty acid profile by providing new synthetic pathways in the host or by suppressing undesired pathways, thereby increasing levels of desired PUFAs, or conjugated forms thereof, and decreasing levels of undesired PUFAs.

Production of Fatty Acids in Animals

Production of fatty acids in animals also presents several advantages. Expression of desaturase genes in animals can produce greatly increased levels of desired PUFAs in animal tissues, making recovery from those tissues more economical. For example, where the desired PUFAs are expressed in the breast milk of animals, methods of isolating PUFAs from animal milk are well established. In addition to providing a source for purification of desired PUFAs, animal breast milk can be manipulated through expression of desaturase genes, either alone or in combination with other human genes, to provide animal milks substantially similar to human breast milk during the different stages of infant development. Humanized animal milks could serve as infant formulas where human nursing is impossible or undesired, or in cases of malnourishment or disease.

Depending upon the host cell, the availability of substrate, and the desired end product(s), several polypeptides, particularly desaturases, are of interest. By “desaturase” is intended a polypeptide which can desaturate one or more fatty acids to produce a mono- or poly-unsaturated fatty acid or precursor thereof of interest. Of particular interest are polypeptides which can catalyze the conversion of stearic acid to oleic acid, of oleic acid to LA, of LA to ALA, of LA to GLA, or of ALA to SDA, which includes enzymes which desaturate at the Δ9, Δ12, (ω6), Δ15, (ω3) or Δ6 positions. By “polypeptide” is meant any chain of amino acids, regardless of length or post-translational modification, for example, glycosylation or phosphorylation. Considerations for choosing a specific polypeptide having desaturase activity include the pH optimum of the polypeptide, whether the polypeptide is a rate limiting enzyme or a component thereof, whether the desaturase used is essential for synthesis of a desired poly-unsaturated fatty acid, and/or co-factors required by the polypeptide. The expressed polypeptide preferably has parameters compatible with the biochemical environment of its location in the host cell. For example, the polypeptide may have to compete for substrate with other enzymes in the host cell. Analyses of the $K_m$ and specific activity of the polypeptide in question therefore are considered in determining the suitability of a given polypeptide for modifying PUFA production in a given host cell. The polypeptide used in a particular situation is one which can function under the conditions present in the intended host cell but otherwise can be any polypeptide having desaturase activity which has the desired characteristic of being capable of modifying the relative production of a desired PUFA.

Figure 2:
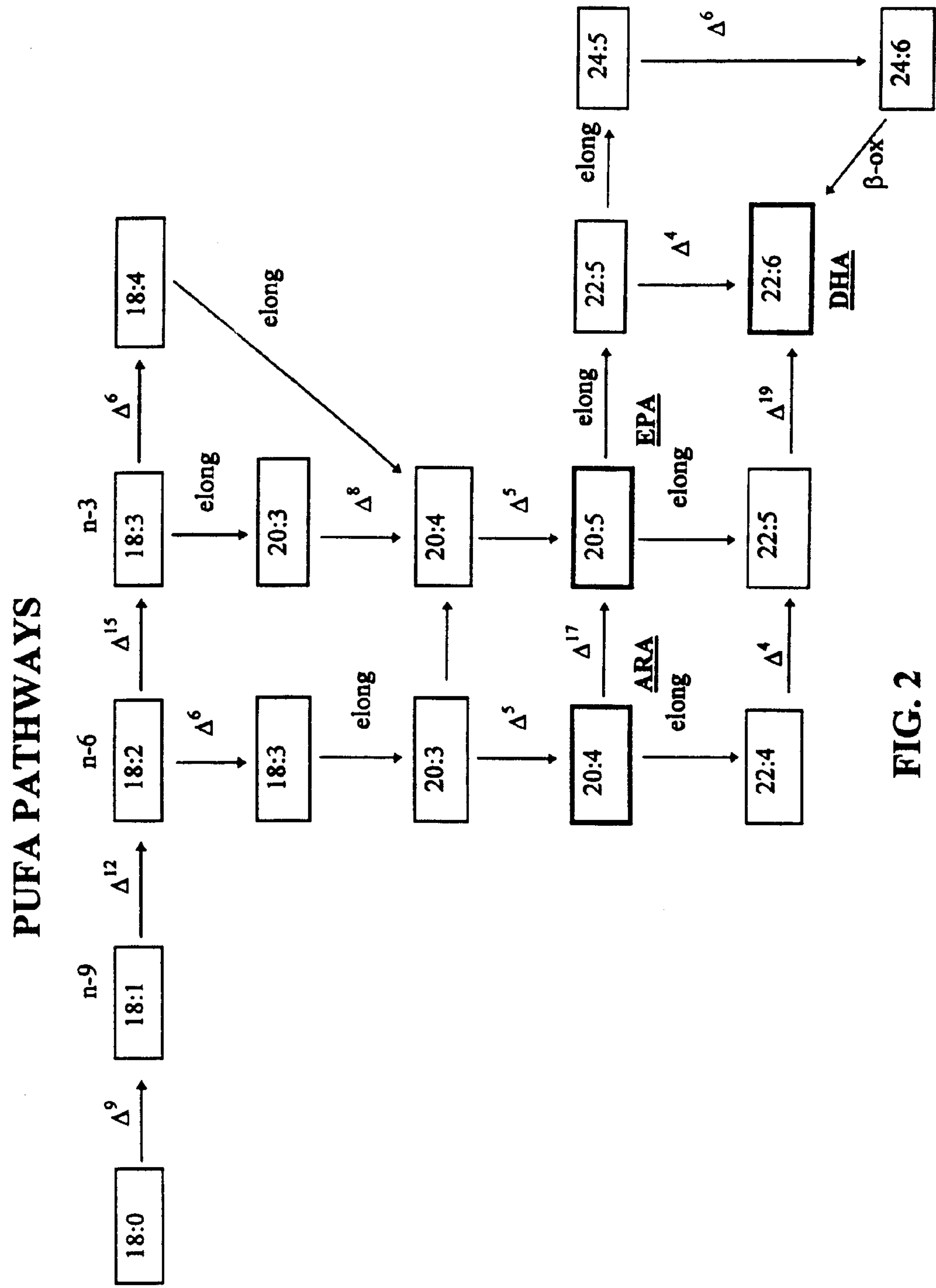
FIG. 2 shows possible pathways for production of PUFAs in addition to ARA, including EPA and DHA, again compiled from a variety of organisms.

For production of linoleic acid from oleic acid, the DNA sequence used encodes a polypeptide having Δ12-desaturase activity. For production of GLA from linoleic acid, the DNA sequence used encodes a polypeptide having Δ6-desaturase activity. In particular instances, expression of Δ6-desaturase activity can be coupled with expression of Δ12-desaturase activity and the host cell can optionally be depleted of any Δ15-desaturase activity present, for example by providing a transcription cassette for production of antisense sequences to the Δ15-desaturase transcription product, by disrupting the Δ15-desaturase gene, or by using a host cell which naturally has, or has been mutated to have, low Δ15-desaturase activity. Inhibition of undesired desaturase pathways also can be accomplished through the use of specific desaturase inhibitors such as those described in U.S. Pat. No. 4,778,630. Also, a host cell for Δ6-desaturase expression may have, or have been mutated to have, high Δ12-desaturase activity. The choice of combination of cassettes used depends in part on the PUFA profile and/or desaturase profile of the host cell. Where the host cell expresses Δ12-desaturase activity and lacks or is depleted in Δ15-desaturase activity, overexpression of Δ6-desaturase alone generally is sufficient to provide for enhanced GLA production. Where the host cell expresses Δ9-desaturase activity, expression of a Δ12- and a Δ6-desaturase can provide for enhanced GLA production. When Δ9-desaturase activity is absent or limiting, an expression cassette for Δ9-desaturase can be used. A scheme for the synthesis of arachidonic acid (20:4 $\Delta^{5, 8, 11, 14}$) from stearic acid (18:0) is shown in FIG. 2. A key enzyme in this pathway is a Δ6-desaturase which converts the linoleic acid into γ-linolenic acid. Conversion of α-linolenic acid (ALA) to stearidonic acid by a Δ6-desaturase also is shown.

Sources of Polypeptides having Desaturase Activity

A source of polypeptides having desaturase activity and oligonucleotides encoding such polypeptides are organisms which produce a desired poly-unsaturated fatty acid. As an example, microorganisms having an ability to produce GLA or ARA can be used as a source of Δ6- or Δ12-desaturase activity. Such microorganisms include, for example, those belonging to the genera *Mortierella, Conidiobolus, Pythium, Phytophathora, Penicillium, Porphyridium, Coidosporium, Mucor, Fusarium, Aspergillus, Rhodotorula*, and *Entomophthora*. Within the genus *Porphyridium*, of particular interest is *Porphyridium cruentum*. Within the genus *Mortierella*, of particular interest are *Mortierella elongata, Mortierella exigua, Mortierella hygrophila, Mortierella ramanniana*, var. angulispora, and *Mortierella alpina*. Within the genus *Mucor*, of particular interest are *Mucor circinelloides* and *Mucor javanicus*.

DNAs encoding desired desaturases can be identified in a variety of ways. As an example, a source of the desired desaturase, for example genomic or cDNA libraries from *Mortierella*, is screened with detectable enzymatically- or chemically-synthesized probes, which can be made from DNA, RNA, or non-naturally occurring nucleotides, or mixtures thereof. Probes may be enzymatically synthesized from DNAs of known desaturases for normal or reduced-stringency hybridization methods. Oligonucleotide probes also can be used to screen sources and can be based on sequences of known desaturases, including sequences conserved among known desaturases, or on peptide sequences obtained from the desired purified protein. Oligonucleotide probes based on amino acid sequences can be degenerate to encompass the degeneracy of the genetic code, or can be biased in favor of the preferred codons of the source organism. Oligonucleotides also can be used as primers for PCR from reverse transcribed mRNA from a known or suspected source; the PCR product can be the full length cDNA or can be used to generate a probe to obtain the desired full length cDNA. Alternatively, a desired protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA also can be employed.

For the most part, some or all of the coding sequence for the polypeptide having desaturase activity is from a natural source. In some situations, however, it is desirable to modify all or a portion of the codons, for example, to enhance expression, by employing host preferred codons. Host preferred codons can be determined from the codons of highest frequency in the proteins expressed in the largest amount in a particular host species of interest. Thus, the coding sequence for a polypeptide having desaturase activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable in the desired host cell. Methods for synthesizing sequences and bringing sequences together are well established in the literature. In vitro mutagenesis and selection, site-directed mutagenesis, or other means can be employed to obtain mutations of naturally occurring desaturase genes to produce a polypeptide having desaturase activity in vivo with more desirable physical and kinetic parameters for function in the host cell, such as a longer half-life or a higher rate of production of a desired polyunsaturated fatty acid.

*Mortieralla alpina* Desaturase

Of particular interest is the *Mortierella alpina* Δ6-desaturase, which has 457 amino acids and a predicted molecular weight of 51.8 kD; the amino acid sequence is shown in FIG. 3. The gene encoding the *Mortierella alpina* Δ6-desaturase can be expressed in transgenic microorganisms or animals to effect greater synthesis of GLA from linoleic acid or of stearidonic acid from ALA. Other DNAs which are substantially identical to the *Mortierella alpina* Δ6-desaturase DNA, or which encode polypeptides which are substantially identical to the *Mortierella alpina* Δ6-desaturase polypeptide, also can be used. By substantially identical is intended an amino acid sequence or nucleic acid sequence exhibiting in order of increasing preference at least 60%, 80%, 90% or 95% homology to the *Mortierella alpina* Δ6-desaturase amino acid sequence or nucleic acid sequence encoding the amino acid sequence. For polypeptides, the length of comparison sequences generally is at least 16 amino acids, preferably at least 20 amino acids, or most preferably 35 amino acids. For nucleic acids, the length of comparison sequences generally is at least 50 nucleotides, preferably at least 60 nucleotides, and more preferably at least 75 nucleotides, and most preferably, 110 nucleotides. Homology typically is measured using sequence analysis software, for example, the Sequence Analysis software package of the Genetics Computer Group, University of Wisconsin Biotechnology Center, 1710 University Avenue, Madison, Wis. 53705, MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). Such software matches similar sequences by assigning degrees of homology to various substitutions, deletions, and other modifications. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* 157: 105-132, 1982), or on the basis of the ability to assume similar polypeptide secondary structure (Chou and Fasman, *Adv. Enzymol.* 47: 45-148, 1978).

Also of interest is the *Mortierella alpina* Δ12-desaturase, the nucleotide and amino acid sequence of which is shown in FIG. 5. The gene encoding the *Mortierella alpina* Δ12-desaturase can be expressed in transgenic microorganisms or animals to effect greater synthesis of LA from oleic acid. Other DNAs which are substantially identical to the *Mortierella alpina* Δ12-desaturase DNA, or which encode polypeptides which are substantially identical to the *Mortierella alpina* Δ12-desaturase polypeptide, also can be used.

Other Desaturases

Encompassed by the present invention are related desaturases from the same or other organisms. Such related desaturases include variants of the disclosed Δ6- or Δ12-desaturase naturally occurring within the same or different species of *Mortierella*, as well as homologues of the disclosed Δ6- or Δ12-desaturase from other species. Also included are desaturases which, although not substantially identical to the *Mortierella alpina* Δ6- or Δ12-desaturase, desaturate a fatty acid molecule at carbon 6 or 12, respectively, from the carboxyl end of a fatty acid molecule, or at carbon 12 or 6 from the terminal methyl carbon in an 18 carbon fatty acid molecule. Related desaturases can be identified by their ability to function substantially the same as the disclosed desaturases; that is, are still able to effectively convert LA to GLA, ALA to SDA or oleic acid to LA. Related desaturases also can be identified by screening sequence databases for sequences homologous to the disclosed desaturases, by hybridization of a probe based on the disclosed desaturases to a library constructed from the source organism, or by RT-PCR using mRNA from the source organism and primers based on the disclosed desaturases. Such desaturases include those from humans, *Dictyostelium discoideum* and *Phaeodactylum tricornum.*

The regions of a desaturase polypeptide important for desaturase activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a desaturase polypeptide important for activity. A mutated construct is expressed, and the ability of the resulting altered protein to function as a desaturase is assayed. Such structure-function analysis can determine which regions may be deleted, which regions tolerate insertions, and which point mutations allow the mutant protein to function in substantially the same way as the native desaturase. All such mutant proteins and nucleotide sequences encoding them are within the scope of the present invention.

Expression of Desaturase Genes

Once the DNA encoding a desaturase polypeptide has been obtained, it is placed in a vector capable of replication in a host cell, or is propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells. The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell.

For expression of a desaturase polypeptide, functional transcriptional and translational initiation and termination regions are operably linked to the DNA encoding the desaturase polypeptide. Expression of the polypeptide coding region can take place in vitro or in a host cell. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell.

Expression In Vitro

In vitro expression can be accomplished, for example, by placing the coding region for the desaturase polypeptide in an expression vector designed for in vitro use and adding rabbit reticulocyte lysate and cofactors; labeled amino acids can be incorporated if desired. Such in vitro expression vectors may provide some or all of the expression signals necessary in the system used. These methods are well known in the art and the components of the system are commercially available. The reaction mixture can then be assayed directly for the polypeptide, for example by determining its activity, or the synthesized polypeptide can be purified and then assayed.

Expression in a Host Cell

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When increased expression of the desaturase polypeptide in the source organism is desired, several methods can be employed. Additional genes encoding the desaturase polypeptide can be introduced into the host organism. Expression from the native desaturase locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (U.S. Pat. No. 4,910,141).

When it is desirable to express more than one different gene, appropriate regulatory regions and expression methods, introduced genes can be propagated in the host cell through use of replicating vectors or by integration into the host genome. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced genes are expressed at the necessary levels to provide for synthesis of the desired products.

As an example, where the host cell is a yeast, transcriptional and translational regions functional in yeast cells are provided, particularly from the host species. The transcriptional initiation regulatory regions can be obtained, for example from genes in the glycolytic pathway, such as alcohol dehydrogenase, glyceraldehyde-3-phosphate dehydrogenase (GPD), phosphoglucoisomerase, phosphoglycerate kinase, etc. or regulatable genes such as acid phosphatase, lactase, metallothionein, glucoamylase, etc. Any one of a number of regulatory sequences can be used in a particular situation, depending upon whether constitutive or induced transcription is desired, the particular efficiency of the promoter in conjunction with the open-reading frame of interest, the ability to join a strong promoter with a control region from a different promoter which allows for inducible transcription, ease of construction, and the like. Of particular interest are promoters which are activated in the presence of galactose. Galactose-inducible promoters (GAL1, GAL7, and GAL10) have been extensively utilized for high level and regulated expression of protein in yeast (Lue et al., *Mol. Cell. Biol*. Vol. 7, p. 3446, 1987; Johnston, *Microbiol. Rev*. Vol. 51, p. 458, 1987). Transcription from the GAL promoters is activated by the GAL4 protein, which binds to the promoter region and activates transcription when galactose is present. In the absence of galactose, the antagonist GAL80 binds to GAL4 and prevents GAL4 from activating transcription. Addition of galactose prevents GAL80 from inhibiting activation by GAL4.

Nucleotide sequences surrounding the translational initiation codon ATG have been found to affect expression in yeast cells. If the desired polypeptide is poorly expressed in yeast, the nucleotide sequences of exogenous genes can be modified to include an efficient yeast translation initiation sequence to obtain optimal gene expression. For expression in *Saccharomyces*, this can be done by site-directed mutagenesis of an inefficiently expressed gene by fusing it in-frame to an endogenous *Saccharomyces* gene, preferably a highly expressed gene, such as the lactase gene.

The termination region can be derived from the 3' region of the gene from which the initiation region was obtained or from a different gene. A large number of termination regions are known to and have been found to be satisfactory in a variety of hosts from the same and different genera and species. The termination region usually is selected more as a matter of convenience rather than because of any particular property. Preferably, the termination region is derived from a yeast gene, particularly *Saccharomyces, Schizosaccharomyces, Candida* or *Kluyveromyces*. The 3' regions of two mammalian genes, γ interferon and α2 interferon, are also known to function in yeast.

Introduction of Constructs into Host Cells

Constructs comprising the gene of interest may be introduced into a host cell by standard techniques. These techniques include transformation, protoplast fusion, lipofection, transfection, transduction, conjugation, infection, bolistic impact, electroporation, microinjection, scraping, or any other method which introduces the gene of interest into the host cell. Methods of transformation which are used include lithium acetate transformation (*Methods in Enzymology*, Vol. 194, p. 186-187, 1991). For convenience, a host cell which has been manipulated by any method to take up a DNA sequence or construct will be referred to as "transformed" or "recombinant" herein.

The subject host will have at least have one copy of the expression construct and may have two or more, depending upon whether the gene is integrated into the genome, amplified, or is present on an extrachromosomal element having multiple copy numbers. Where the subject host is a yeast, four principal types of yeast plasmid vectors can be used: Yeast Integrating plasmids (YIps), Yeast Replicating plasmids (YRps), Yeast Centromere plasmids (YCps), and Yeast Episomal plasmids (YEps). YIps lack a yeast replication origin and must be propagated as integrated elements in the yeast genome. YRps have a chromosomally derived autonomously replicating sequence and are propagated as medium copy number (20 to 40), autonomously replicating, unstably segregating plasmids. YCps have both a replication origin and a centromere sequence and propagate as low copy number (10-20), autonomously replicating, stably segregating plasmids. YEps have an origin of replication from the yeast 2 μm plasmid and are propagated as high copy number, autonomously replicating, irregularly segregating plasmids. The presence of the plasmids in yeast can be ensured by maintaining selection for a marker on the plasmid. Of particular interest are the yeast vectors pYES2 (a YEp plasmid available from Invitrogen, confers uracil prototrophy and a GAL1 galactose-inducible promoter for expression), pRS425-pG1 (a YEp plasmid obtained from Dr. T. H. Chang, Ass. Professor of Molecular Genetics, Ohio State University, containing a constitutive GPD promoter and conferring leucine prototrophy), and pYX424 (a YEp plasmid having a constitutive TP1 promoter and conferring leucine prototrophy; Alber, T. and Kawasaki, G. (1982). *J. Mol. & Appl. Genetics* 1: 419).

The transformed host cell can be identified by selection for a marker contained on the introduced construct. Alternatively, a separate marker construct may be introduced with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene therefor may confer antibiotic resistance, or encode an essential growth factor or enzyme, and permit growth on selective media when expressed in the transformed host. Selection of a transformed host can also occur when the expressed marker protein can be detected, either directly or indirectly. The marker protein may be expressed alone or as a fusion to another protein. The marker protein can be detected by its enzymatic activity; for example β galactosidase can convert the substrate X-gal to a colored product, and luciferase can convert luciferin to a light-emitting product. The marker protein can be detected by its light-producing or modifying characteristics; for example, the green fluorescent protein of *Aequorea victoria* fluoresces when illuminated with blue light. Antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Desirably, resistance to kanamycin and the amino glycoside G418 are of interest, as well as ability to grow on media lacking uracil, leucine, lysine or tryptophan.

Of particular interest is the Δ6- and Δ12-desaturase-mediated production of PUFAs in prokaryotic and eukaryotic host cells. Prokaryotic cells of interest include *Eschericia, Bacil-*

*lus, Lactobacillus*, cyanobacteria and the like. Eukaryotic cells include mammalian cells such as those of lactating animals, avian cells such as of chickens, and other cells amenable to genetic manipulation including insect, fungal, and algae cells. The cells may be cultured or formed as part or all of a host organism including an animal. Viruses and bacteriophage also may be used with the cells in the production of PUFAs, particularly for gene transfer, cellular targeting and selection. In a preferred embodiment, the host is any microorganism or animal which produces and/or can assimilate exogenously supplied substrate(s) for a Δ6- and/or Δ12-desaturase, and preferably produces large amounts of one or more of the substrates. Examples of host animals include mice, rats, rabbits, chickens, quail, turkeys, bovines, sheep, pigs, goats, yaks, etc., which are amenable to genetic manipulation and cloning for rapid expansion of the transgene expressing population. For animals, the desaturase transgene(s) can be adapted for expression in target organelles, tissues and body fluids through modification of the gene regulatory regions. Of particular interest is the production of PUFAs in the breast milk of the host animal.

Expression in Yeast

Examples of host microorganisms include *Saccharomyces cerevisiae, Saccharomyces carlsbergensis*, or other yeast such as *Candida, Kluyveromyces* or other fungi, for example, filamentous fungi such as *Aspergillus, Neurospora, Penicillium*, etc. Desirable characteristics of a host microorganism are, for example, that it is genetically well characterized, can be used for high level expression of the product using ultra-high density fermentation, and is on the GRAS (generally recognized as safe) list since the proposed end product is intended for ingestion by humans. Of particular interest is use of a yeast, more particularly baker's yeast (*S. cerevisiae*), as a cell host in the subject invention. Strains of particular interest are SC334 (Mat α pep4-3 prb1-1122 ura3-52 leu2-3, 112 reg1-501 gal1; *Gene* 83:57-64, 1989, Hovland P. et al.), YTC34 (α ade2-101 his3Δ200 lys2-801 ura3-52; obtained from Dr. T. H. Chang, Ass. Professor of Molecular Genetics, Ohio State University), YTC41 (a/α ura3-52/ura3=52 lys2-801/lys2-801 ade2-101/ade2-101 trp1-Δ1/trp1-Δ1 his3Δ200/his3Δ200 leu2Δ1/leu2Δ1; obtained from Dr. T. H. Chang, Ass. Professor of Molecular Genetics, Ohio State University), BJ1995 (obtained from the Yeast Genetic Stock Centre, 1021 Donner Laboratory, Berkeley, Calif. 94720), INVSC1 (Mat α hiw3Δ1 leu2 trp1-289 ura3-52; obtained from Invitrogen, 1600 Faraday Ave., Carlsbad, Calif. 92008) and INVSC2 (Mat α his3Δ200 ura3-167; obtained from Invitrogen).

Expression in Avian Species

For producing PUFAs in avian species and cells, such as chickens, turkeys, quail and ducks, gene transfer can be performed by introducing a nucleic acid sequence encoding a Δ6 and/or Δ12-desaturase into the cells following procedures known in the art. If a transgenic animal is desired, pluripotent stem cells of embryos can be provided with a vector carrying a desaturase encoding transgene and developed into adult animal (U.S. Pat. No. 5,162,215; Ono et al. (1996) *Comparative Biochemistry and Physiology A* 113(3):287-292; WO 9612793; WO 9606160). In most cases, the transgene will be modified to express high levels of the desaturase in order to increase production of PUFAs. The transgene can be modified, for example, by providing transcriptional and/or translational regulatory regions that function in avian cells, such as promoters which direct expression in particular tissues and egg parts such as yolk. The gene regulatory regions can be obtained from a variety of sources, including chicken anemia or avian leukosis viruses or avian genes such as a chicken ovalbumin gene.

Expression in Insect Cells

Production of PUFAs in insect cells can be conducted using baculovirus expression vectors harboring one or more desaturase transgenes. Baculovirus expression vectors are available from several commercial sources such as Clonetech. Methods for producing hybrid and transgenic strains of algae, such as marine algae, which contain and express a desaturase transgene also are provided. For example, transgenic marine algae may be prepared as described in U.S. Pat. No. 5,426,040. As with the other expression systems described above, the timing, extent of expression and activity of the desaturase transgene can be regulated by fitting the polypeptide coding sequence with the appropriate transcriptional and translational regulatory regions selected for a particular use. Of particular interest are promoter regions which can be induced under preselected growth conditions. For example, introduction of temperature sensitive and/or metabolite responsive mutations into the desaturase transgene coding sequences, its regulatory regions, and/or the genome of cells into which the transgene is introduced can be used for this purpose.

The transformed host cell is grown under appropriate conditions adapted for a desired end result. For host cells grown in culture, the conditions are typically optimized to produce the greatest or most economical yield of PUFAs, which relates to the selected desaturase activity. Media conditions which may be optimized include: carbon source, nitrogen source, addition of substrate, final concentration of added substrate, form of substrate added, aerobic or anaerobic growth, growth temperature, inducing agent, induction temperature, growth phase at induction, growth phase at harvest, pH, density, and maintenance of selection. Microorganisms of interest, such as yeast are preferably grown in selected medium. For yeast, complex media such as peptone broth (YPD) or a defined media such as a minimal media (contains amino acids, yeast nitrogen base, and ammonium sulfate, and lacks a component for selection, for example uracil) are preferred. Desirably, substrates to be added are first dissolved in ethanol. Where necessary, expression of the polypeptide of interest may be induced, for example by including or adding galactose to induce expression from a GAL promoter.

Expression in Plants

Production of PUFA's in plants can be conducted using various plant transformation systems such as the use of *Agrobacterium tumefaciens*, plant viruses, particle cell transformation and the like which are disclosed in Applicant's related applications U.S. application Ser. Nos. 08/834,033 and 08/956,985 and continuation-in-part applications filed simultaneously with this application all of which are hereby incorporated by reference.

Expression in an Animal

Expression in cells of a host animal can likewise be accomplished in a transient or stable manner. Transient expression can be accomplished via known methods, for example infection or lipofection, and can be repeated in order to maintain desired expression levels of the introduced construct (see Ebert, PCT publication WO 94/05782). Stable expression can be accomplished via integration of a construct into the host genome, resulting in a transgenic animal. The construct can be introduced, for example, by microinjection of the construct into the pronuclei of a fertilized egg, or by transfection, retroviral infection or other techniques whereby the construct is introduced into a cell line which may form or be incorporated into an adult animal (U.S. Pat. No. 4,873,191; U.S. Pat. No. 5,530,177; U.S. Pat. No. 5,565,362; U.S. Pat. No. 5,366,894; Willmut et al (1997) Nature 385:810). The recombinant eggs or embryos are transferred to a surrogate mother (U.S. Pat. No. 4,873,191; U.S. Pat. No. 5,530,177; U.S. Pat. No. 5,565,362; U.S. Pat. No. 5,366,894; Wilmut et al (supra)).

After birth, transgenic animals are identified, for example, by the presence of an introduced marker gene, such as for coat color, or by PCR or Southern blotting from a blood, milk or tissue sample to detect the introduced construct, or by an immunological or enzymological assay to detect the expressed protein or the products produced therefrom (U.S. Pat. No. 4,873,191; U.S. Pat. No. 5,530,177; U.S. Pat. No. 5,565,362; U.S. Pat. No. 5,366,894; Wilmut et al (supra)). The resulting transgenic animals may be entirely transgenic or may be mosaics, having the transgenes in only a subset of their cells. The advent of mammalian cloning, accomplished by fusing a nucleated cell with an enucleated egg, followed by transfer into a surrogate mother, presents the possibility of rapid, large-scale production upon obtaining a "founder" animal or cell comprising the introduced construct; prior to this, it was necessary for the transgene to be present in the germ line of the animal for propagation (Wilmut et al (supra)).

Expression in a host animal presents certain efficiencies, particularly where the host is a domesticated animal. For production of PUFAs in a fluid readily obtainable from the host animal, such as milk, the desaturase transgene can be expressed in mammary cells from a female host, and the PUFA content of the host cells altered. The desaturase transgene can be adapted for expression so that it is retained in the mammary cells, or secreted into milk, to form the PUFA reaction products localized to the milk (PCT publication WO 95/24488). Expression can be targeted for expression in mammary tissue using specific regulatory sequences, such as those of bovine α-lactalbumin, α-casein, β-casein, γ-casein, κ-casein, β-lactoglobulin, or whey acidic protein, and may optionally include one or more introns and/or secretory signal sequences (U.S. Pat. No. 5,530,177; Rosen, U.S. Pat. No. 5,565,362; Clark et al., U.S. Pat. No. 5,366,894; Garner et al., PCT publication WO 95/23868). Expression of desaturase transgenes, or antisense desaturase transcripts, adapted in this manner can be used to alter the levels of specific PUFAs, or derivatives thereof, found in the animals milk. Additionally, the desaturase transgene(s) can be expressed either by itself or with other transgenes, in order to produce animal milk containing higher proportions of desired PUFAs or PUFA ratios and concentrations that resemble human breast milk (Prieto et al., PCT publication WO 95/24494).

Purification of Fatty Acids

The desaturated fatty acids may be found in the host microorganism or animal as free fatty acids or in conjugated forms such as acylglycerols, phospholipids, sulfolipids or glycolipids, and may be extracted from the host cell through a variety of means well-known in the art. Such means may include extraction with organic solvents, sonication, supercritical fluid extraction using for example carbon dioxide, and physical means such as presses, or combinations thereof. Of particular interest is extraction with hexane or methanol and chloroform. Where desirable, the aqueous layer can be acidified to protonate negatively charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high speed centrifugation or distillation, or combinations of these techniques. Protection of reactive groups, such as the acid or alkenyl groups, may be done at any step through known techniques, for example alkylation or iodination. Methods used include methylation of the fatty acids to produce methyl esters. Similarly, protecting groups may be removed at any step. Desirably, purification of fractions containing GLA, SDA, ARA, DHA and EPA may be accomplished by treatment with urea and/or fractional distillation.

Uses of Fatty Acids

The fatty acids of the subject invention finds many applications. Probes based on the DNAs of the present invention may find use in methods for isolating related molecules or in methods to detect organisms expressing desaturases. When used as probes, the DNAs or oligonucleotides must be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practical to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labelling methods can be found in U.S. Pat. No. 5,011,770. Alternatively, the binding of target molecules can be directly detected by measuring the change in heat of solution on binding of probe to target via isothermal titration calorimetry, or by coating the probe or target on a surface and detecting the change in scattering of light from the surface produced by binding of target or probe, respectively, as may be done with the BIAcore system.

PUFAs produced by recombinant means find applications in a wide variety of areas. Supplementation of animals or humans with PUFAs in various forms can result in increased levels not only of the added PUFAs but of their metabolic progeny as well.

Nutritional Compositions

The present invention also includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic function.

The nutritional composition of the present invention comprises at least one oil or acid produced in accordance with the present invention and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will of semi-purified or purified origin. By semi-purified or purified is meant a material which has been prepared by purification of a natural material or by synthesis.

Examples of nutritional compositions of the present invention include but are not limited to infant formulas, dietary supplements, and rehydration compositions. Nutritional compositions of particular interest include but are not limited to those utilized for enteral and parenteral supplementation for infants, specialist infant formulae, supplements for the elderly, and supplements for those with gastrointestinal difficulties and/or malabsorption.

Nutritional Compositions

A typical nutritional composition of the present invention will contain edible macronutrients, vitamins and minerals in amounts desired for a particular use. The amounts of such ingredients will vary depending on whether the formulation is intended for use with normal, healthy individuals temporarily exposed to stress, or to subjects having specialized needs due to certain chronic or acute disease states (e.g., metabolic disorders). It will be understood by persons skilled in the art that the components utilized in a nutritional formulation of the present invention are of semi-purified or purified origin. By semi-purified or purified is meant a material that has been prepared by purification of a natural material or by synthesis. These techniques are well known in the art (See, e.g., Code of Federal Regulations for Food Ingredients and Food Processing; Recommended Dietary Allowances, $10^{th}$ Ed., National Academy Press, Washington, D.C., 1989).

In a preferred embodiment, a nutritional formulation of the present invention is an enteral nutritional product, more preferably an adult or child enteral nutritional product. Accordingly in a further aspect of the invention, a nutritional formulation is provided that is suitable for feeding adults or children, who are experiencing stress. The formula comprises, in addition to the PUFAs of the invention; macronutrients, vitamins and minerals in amounts designed to provide the daily nutritional requirements of adults.

The macronutritional components include edible fats, carbohydrates and proteins. Exemplary edible fats are coconut oil, soy oil, and mono- and diglycerides and the PUFA oils of this invention. Exemplary carbohydrates are glucose, edible lactose and hydrolyzed cornstarch. A typical protein source would be soy protein, electrodialysed whey or electrodialysed skim milk or milk whey, or the hydrolysates of these proteins, although other protein sources are also available and may be used. These macronutrients would be added in the form of commonly accepted nutritional compounds in amount equivalent to those present in human milk or an energy basis, i.e., on a per calorie basis.

Methods for formulating liquid and enteral nutritional formulas are well known in the art and are described in detail in the examples.

The enteral formula can be sterilized and subsequently utilized on a ready-to-feed (RTF) basis or stored in a concentrated liquid or a powder. The powder can be prepared by spray drying the enteral formula prepared as indicated above, and the formula can be reconstituted by rehydrating the concentrate. Adult and infant nutritional formulas are well known in the art and commercially available (e.g., Similac®, Ensure®, Jevity® and Alimentum® from Ross Products Division, Abbott Laboratories). An oil or acid of the present invention can be added to any of these formulas in the amounts described below.

The energy density of the nutritional composition when in liquid form, can typically range from about 0.6 to 3.0 Kcal per ml. When in solid or powdered form, the nutritional supplement can contain from about 1.2 to more than 9 Kcals per gm, preferably 3 to 7 Kcals per gm. In general, the osmolality of a liquid product should be less than 700 mOsm and more preferably less than 660 mOsm.

The nutritional formula would typically include vitamins and minerals, in addition to the PUFAs of the invention, in order to help the individual ingest the minimum daily requirements for these substances. In addition to the PUFAs listed above, it may also be desirable to supplement the nutritional composition with zinc, copper, and folic acid in addition to antioxidants. It is believed that these substances will also provide a boost to the stressed immune system and thus will provide further benefits to the individual. The presence of zinc, copper or folic acid is optional and is not required in order to gain the beneficial effects on immune suppression. Likewise a pharmaceutical composition can be supplemented with these same substances as well.

In a more preferred embodiment, the nutritional contains, in addition to the antioxidant system and the PUFA component, a source of carbohydrate wherein at least 5 weight % of said carbohydrate is an indigestible oligosaccharide. In yet a more preferred embodiment, the nutritional composition additionally contains protein, taurine and carnitine.

The PUFAs, or derivatives thereof, made by the disclosed method can be used as dietary substitutes, or supplements, particularly infant formulas, for patients undergoing intravenous feeding or for preventing or treating malnutrition. Typically, human breast milk has a fatty acid profile comprising from about 0.15% to about 0.36% as DHA, from about 0.03% to about 0.13% as EPA, from about 0.30% to about 0.88% as ARA, from about 0.22% to about 0.67% as DGLA, and from about 0.27% to about 1.04% as GLA. Additionally, the predominant triglyceride in human milk has been reported to be 1,3-di-oleoyl-2-palmitoyl, with 2-palmitoyl glycerides reported as better absorbed than 2-oleoyl or 2-lineoyl glycerides (U.S. Pat. No. 4,876,107). Thus, fatty acids such as ARA, DGLA, GLA and/or EPA produced by the invention can be used to alter the composition of infant formulas to better replicate the PUFA composition of human breast milk. In particular, an oil composition for use in a pharmacologic or food supplement, particularly a breast milk substitute or supplement, will preferably comprise one or more of ARA, DGLA and GLA. More preferably the oil will comprise from about 0.3 to 30% ARA, from about 0.2 to 30% DGLA, and from about 0.2 to about 30% GLA.

In addition to the concentration, the ratios of ARA, DGLA and GLA can be adapted for a particular given end use. When formulated as a breast milk supplement or substitute, an oil composition which contains two or more of ARA, DGLA and GLA will be provided in a ratio of about 1:19:30 to about 6:1:0.2, respectively. For example, the breast milk of animals can vary in ratios of ARA:DGLA:DGL ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to ARA can be used to precisely control the PUFA ratios. For example, a 5% to 10% conversion rate of DGLA to ARA can be used to produce an ARA to DGLA ratio of about 1:19, whereas a conversion rate of about 75% to 80% can be used to produce an ARA to DGLA ratio of about 6:1. Therefore, whether in a cell culture system or in a host animal, regulating the timing, extent and specificity of desaturase expression as described can be used to modulate the PUFA levels and ratios. Depending on the expression system used, e.g., cell culture or an animal expressing oil(s) in its milk, the oils also can be isolated and recombined in the desired concentrations and ratios. Amounts of oils providing these ratios of PUFA can be determined following standard protocols. PUFAs, or host cells containing them, also can be used as animal food supplements to alter an animal's tissue or milk fatty acid composition to one more desirable for human or animal consumption.

For dietary supplementation, the purified PUFAs, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents.

Pharmaceutical Compositions

The present invention also encompasses a pharmaceutical composition comprising one or more of the acids and/or resulting oils produced in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream.

Possible routes of administration include, for example, oral, rectal and parenteral. The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

Additionally, the composition of the present invention may be utilized for cosmetic purposes. It may be added to pre-existing cosmetic compositions such that a mixture is formed or may be used as a sole composition.

Pharmaceutical compositions may be utilized to administer the PUFA component to an individual. Suitable pharmaceutical compositions may comprise physiologically acceptable sterile aqueous or non-aqueous solutions, dispersions, suspensions or emulsions and sterile powders for reconstitution into sterile solutions or dispersions for ingestion. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the maintenance of the required particle size in the case of dispersions and by the use of surfactants. It may also be desirable to include isotonic agents, for example sugars, sodium chloride and the like. Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth or mixtures of these substances, and the like.

Solid dosage forms such as tablets and capsules can be prepared using techniques well known in the art. For example, PUFAs of the invention can be tableted with conventional tablet bases such as lactose, sucrose, and cornstarch in combination with binders such as acacia, cornstarch or gelatin, disintegrating agents such as potato starch or alginic acid and a lubricant such as stearic acid or magnesium stearate. Capsules can be prepared by incorporating these excipients into a gelatin capsule along with the antioxidants and the PUFA component. The amount of the antioxidants and PUFA component that should be incorporated into the pharmaceutical formulation should fit within the guidelines discussed above.

As used in this application, the term "treat" refers to either preventing, or reducing the incidence of, the undesired occurrence. For example, to treat immune suppression refers to either preventing the occurrence of this suppression or reducing the amount of such suppression. The terms "patient" and "individual" are being used interchangeably and both refer to an animal. The term "animal" as used in this application refers to any warm-blooded mammal including, but not limited to, dogs, humans, monkeys, and apes. As used in the application the term "about" refers to an amount varying from the stated range or number by a reasonable amount depending upon the context of use. Any numerical number or range specified in the specification should be considered to be modified by the term about.

"Dose" and "serving" are used interchangeably and refer to the amount of the nutritional or pharmaceutical composition ingested by the patient in a single setting and designed to deliver effective amounts of the antioxidants and the structured triglyceride. As will be readily apparent to those skilled in the art, a single dose or serving of the liquid nutritional powder should supply the amount of antioxidants and PUFAs discussed above. The amount of the dose or serving should be a volume that a typical adult can consume in one sitting. This amount can vary widely depending upon the age, weight, sex or medical condition of the patient. However as a general guideline, a single serving or dose of a liquid nutritional produce should be considered as encompassing a volume from 100 to 600 ml, more preferably from 125 to 500 ml and most preferably from 125 to 300 ml.

The PUFAs of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

Pharmaceutical Applications

For pharmaceutical use (human or veterinary), the compositions are generally administered orally but can be administered by any route by which they may be successfully absorbed, e.g., parenterally (i.e. subcutaneously, intramuscularly or intravenously), rectally or vaginally or topically, for example, as a skin ointment or lotion. The PUFAs of the present invention may be administered alone or in combination with a pharmaceutically acceptable carrier or excipient. Where available, gelatin capsules are the preferred form of oral administration. Dietary supplementation as set forth above also can provide an oral route of administration. The unsaturated acids of the present invention may be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, found in PCT publication WO 96/33155. The preferred esters are the ethyl esters. As solid salts, the PUFAs also can be administered in tablet form. For intravenous administration, the PUFAs or derivatives thereof may be incorporated into commercial formulations such as Intralipids. The typical normal adult plasma fatty acid profile comprises 6.64 to 9.46% of ARA, 1.45 to 3.11% of DGLA, and 0.02 to 0.08% of GLA. These PUFAs or their metabolic precursors can be administered, either alone or in mixtures with other PUFAs, to achieve a normal fatty acid profile in a patient. Where desired, the individual components of formulations may be individually provided in kit form, for single or multiple use. A typical dosage of a particular fatty acid is from 0.1 mg to 20 g, or even 100 g daily, and is preferably from 10 mg to 1, 2, 5 or 10 g daily as required, or molar equivalent amounts of derivative forms thereof. Parenteral nutrition compositions comprising from about 2 to about 30 weight percent fatty acids calculated as triglycerides are encompassed by the present invention; preferred is a composition having from about 1 to about 25 weight percent of the total PUFA composition as GLA (U.S. Pat. No. 5,196,198). Other vitamins, and particularly fat-soluble vitamins such as vitamin A, D, E and L-carnitine can optionally be included. Where desired, a preservative such as $\alpha$ tocopherol may be added, typically at about 0.1% by weight.

Suitable pharmaceutical compositions may comprise physiologically acceptable sterile aqueous or non-aqueous solutions, dispersions, suspensions or emulsions and sterile powders for reconstitution into sterile injectible solutions or dispersions. Examples of suitable aqueous and non-aqeuous carriers, diluents, solvents or vehicles include water, ethanol, polyols (propylleneglyol, polyethylenegycol, glycerol, and the like), suitable mixtures thereof, vegetable oils (such as olive oil) and injectable organic esters such as ehyl oleate. Proper fluidity can be maintained, for example, by the maintenance of the required particle size in the case of dispersions and by the use of surfactants. It may also be desirable to include isotonic agents, for example sugars, sodium chloride and the like. Besides such inert diluents, the composition can also include adjuvants, such as wetting agents, emulsifying and suspending agents, sweetening, flavoring and perfuming agents.

Suspensions in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances and the like.

An especially preferred pharmaceutical composition contains diacetyltartaric acid esters of mono- and diglycerides dissolved in an aqueous medium or solvent. Diacetyltartaric acid esters of mono- and diglycerides have an HLB value of about 9-12 and are significantly more hydrophilic than existing antimicrobial lipids that have HLB values of 2-4. Those existing hydrophobic lipids cannot be formulated into aqueous compositions. As disclosed herein, those lipids can now be solubilized into aqueous media in combination with diacetyltartaric acid esters of mono- and diglycerides. In accordance with this embodiment, diacetyltartaric acid esters of mono- and diglycerides (e.g., DATEM-C12:0) is melted with other active antimicrobial lipids (e.g., 18:2 and 12:0 monoglycerides) and mixed to obtain a homogeneous mixture. Homogeneity allows for increased antimicrobial activity. The mixture can be completely dispersed in water. This is not possible without the addition of diacetyltartaric acid esters of mono- and diglycerides and premixing with other monoglycerides prior to introduction into water. The aqueous composition can then be admixed under sterile conditions with physiologically acceptable diluents, preservatives, buffers or propellants as may be required to form a spray or inhalant.

The present invention also encompasses the treatment of numerous disorders with fatty acids. Supplementation with PUFAs of the present invention can be used to treat restenosis after angioplasty. Symptoms of inflammation, rheumatoid arthritis, and asthma and psoriasis can be treated with the PUFAs of the present invention. Evidence indicates that PUFAs may be involved in calcium metabolism, suggesting that PUFAs of the present invention may be used in the treatment or prevention of osteoporosis and of kidney or urinary tract stones.

The PUFAs of the present invention can be used in the treatment of cancer. Malignant cells have been shown to have altered fatty acid compositions; addition of fatty acids has been shown to slow their growth and cause cell death, and to increase their susceptibility to chemotherapeutic agents. GLA has been shown to cause reexpression on cancer cells of the E-cadherin cellular adhesion molecules, loss of which is associated with aggressive metastasis. Clinical testing of intravenous administration of the water soluble lithium salt of GLA to pancreatic cancer patients produced statistically significant increases in their survival. PUFA supplementation may also be useful for treating cachexia associated with cancer.

The PUFAs of the present invention can also be used to treat diabetes (U.S. Pat. No. 4,826,877; Horrobin et al., Am. J. Clin. Nutr. Vol. 57 (Suppl.), 732S-737S). Altered fatty acid metabolism and composition has been demonstrated in diabetic animals. These alterations have been suggested to be involved in some of the long-term complications resulting from diabetes, including retinopathy, neuropathy, nephropathy and reproductive system damage. Primrose oil, which contains GLA, has been shown to prevent and reverse diabetic nerve damage.

The PUFAs of the present invention can be used to treat eczema, reduce blood pressure and improve math scores. Essential fatty acid deficiency has been suggested as being involved in eczema, and studies have shown beneficial effects on eczema from treatment with GLA. GLA has also been shown to reduce increases in blood pressure associated with stress, and to improve performance on arithmetic tests. GLA and DGLA have been shown to inhibit platelet aggregation, cause vasodilation, lower cholesterol levels and inhibit proliferation of vessel wall smooth muscle and fibrous tissue (Brenner et al., Adv. Exp. Med. Biol. Vol. 83, p. 85-101, 1976). Administration of GLA or DGLA, alone or in combination with EPA, has been shown to reduce or prevent gastrointestinal bleeding and other side effects caused by non-steroidal anti-inflammatory drugs (U.S. Pat. No. 4,666,701). GLA and DGLA have also been shown to prevent or treat endometriosis and premenstrual syndrome (U.S. Pat. No. 4,758,592) and to treat myalgic encephalomyelitis and chronic fatigue after viral infections (U.S. Pat. No. 5,116,871).

Further uses of the PUFAs of this invention include use in treatment of AIDS, multiple schlerosis, acute respiratory syndrome, hypertension and inflammatory skin disorders. The PUFAs of the inventions also can be used for formulas for general health as well as for geriatric treatments.

Veterinary Applications

It should be noted that the above-described pharmaceutical and nutritional compositions may be utilized in connection with animals, as well as humans, as animals experience many of the same needs and conditions as human. For example, the oil or acids of the present invention may be utilized in animal feed supplements.

The following examples are presented by way of illustration, not of limitation.

EXAMPLES

Example 1

Construction of a cDNA Library from *Mortierella alpina*

Example 2

Isolation of a Δ6-Desaturase Nucleotide Sequence from *Mortierella alpina*

Example 3

Identification of Δ6-Desaturases Homologous to the *Mortierella alpina* Δ6-Desaturase Example 4

Isolation of a Δ2-Desaturase Nucleotide Sequence from *Mortierella Alpina*

Example 5

Expression of *M. alpina* Desaturase Clones in Baker's Yeast

Example 6

Initial Optimization of Culture Conditions

Example 7

Distribution of PUFAs in Yeast Lipid Fractions

Example 8

Further Culture Optimization and Coexpression of Δ6 and Δ12-Desaturases

Example 9

Identification of Homologues to *M. alpina* Δ5 and Δ6 Desaturases

Example 10

Identification of *M. alpina* Δ5 and Δ6 Homologues in other PUFA-Producing Organisms Example 11

Identification of *M. alpina* Δ5 and Δ6 Homologues in other PUFA-Producing Organisms Example 12

Human Desaturase Gene Sequences

Example 13

Nutritional Compositions

Example 1

Construction of a cDNA Library from *Mortierella alpina*

Total RNA was isolated from a 3 day old PUFA-producing culture of *Mortierella alpina* using the protocol of Hoge et al. (1982) *Experimental Mycology* 6:225-232. The RNA was used to prepare double-stranded cDNA using BRL's lambda-ZipLox system following the manufactures instructions. Several size fractions of the *M. alpina* cDNA were packaged separately to yield libraries with different average-sized inserts. A "full-length" library contains approximately $3\times10^6$ clones with an average insert size of 1.77 kb. The "sequencing-grade" library contains approximately $6\times10^5$ clones with an average insert size of 1.1 kb.

Example 2

Isolation of a Δ6-Desaturase Nucleotide Sequence from *Mortierella Alpina*

A nucleic acid sequence from a partial cDNA clone, Ma524, encoding a Δ6 fatty acid desaturase from *Mortierella alpina* was obtained by random sequencing of clones from the *M. alpina* cDNA sequencing grade library described in Example 1. cDNA-containing plasmids were excised as follows:

Five μl of phage were combined with 100 μl of *E. coli* DH10B(ZIP) grown in ECLB plus 10 μg/ml kanamycin, 0.2% maltose, and 10 mM $MgSO_4$ and incubated at 37 degrees for 15 minutes. 0.9 ml SOC was added and 100 μl of the bacteria immediately plated on each of 10 ECLB+50 μg Pen plates. No 45 minute recovery time was needed. The plates were incubated overnight at 37°. Colonies were picked into ECLB+50 μg Pen media for overnight cultures to be used for making glycerol stocks and miniprep DNA. An aliquot of the culture used for the miniprep is stored as a glycerol stock. Plating on ECLB+50 μg Pen/ml resulted in more colonies and a greater proportion of colonies containing inserts than plating on 100 μg/ml Pen.

Random colonies were picked and plasmid DNA purified using Qiagen miniprep kits. DNA sequence was obtained from the 5' end of the cDNA insert and compared to the National Center for Biotechnology Information (NCBI) nonredundant database using the BLASTX algorithm. Ma524 was identified as a putative desaturase based on DNA sequence homology to previously identified desaturases.

A full-length cDNA clone was isolated from the *M. alpina* full-length library and designed pCGN5532. The cDNA is contained as a 1617 bp insert in the vector pZL1 (BRL) and, beginning with the first ATG, contains an open reading frame encoding 457 amino acids. The three conserved "histidine boxes" known to be conserved among membrane-bound deaturases (Okuley, et al. (1994) *The Plant Cell* 6:147-158) were found to be present at amino acid positions 172-176, 209-213, and 395-399 (see FIG. 3). As with other membrane-bound Δ6-desaturases the final HXXHH histidine box motif was found to be QXXHH. The amino acid sequence of Ma524 was found to display significant homology to a portion of a *Caenorhabditis elegans* cosmid, WO6D2.4, a cytochrome b5/desaturase fusion protein from sunflower, and the *Synechocystis* and *Spirulina* Δ6-desaturases. In addition, Ma524 was shown to have homology to the borage Δ6-desaturase amino sequence (PCT publication W) 96/21022). Ma524 thus appears to encode a Δ6-desaturase that is related to the borage and algal Δ6-desaturases. The peptide sequences are shown as SEQ ID NO:5-SEQ ID NO:11.

The amino terminus of the encoded protein was found to exhibit significant homology to cytochrome b5 proteins. The *Mortierella* cDNA clone appears to represent a fusion between a cytochrome b5 and a fatty acid desaturase. Since cytochrome b5 is believed to function as the electron donor for membrane-bound desaturase enzymes, it is possible that the N-terminal cytochrome b5 domain of this desaturase protein is involved in its function. This may be advantageous when expressing the desaturase in heterologous systems for PUFA production. However, it should be noted that, although the amino acid sequences of Ma524 and the borage Δ6 were found to contain regions of homology, the base compositions of the cDNAs were shown to be significantly different. For example, the borage cDNA was shown to have an overall base composition of 60% A/T, with some regions exceeding 70%, while Ma524 was shown to have an average of 44% A/T base composition, with no regions exceeding 60%. This may have implications for expressing the cDNAs in microorganisms or animals which favor different base compositions. It is known that poor expression of recombinant genes can occur when the host prefers a base composition different from that of the introduced gene. Mechanisms for such poor expression include decreased stability, cryptic splice sites, and/or translatability of the mRNA and the like.

Example 3

Figure 4:
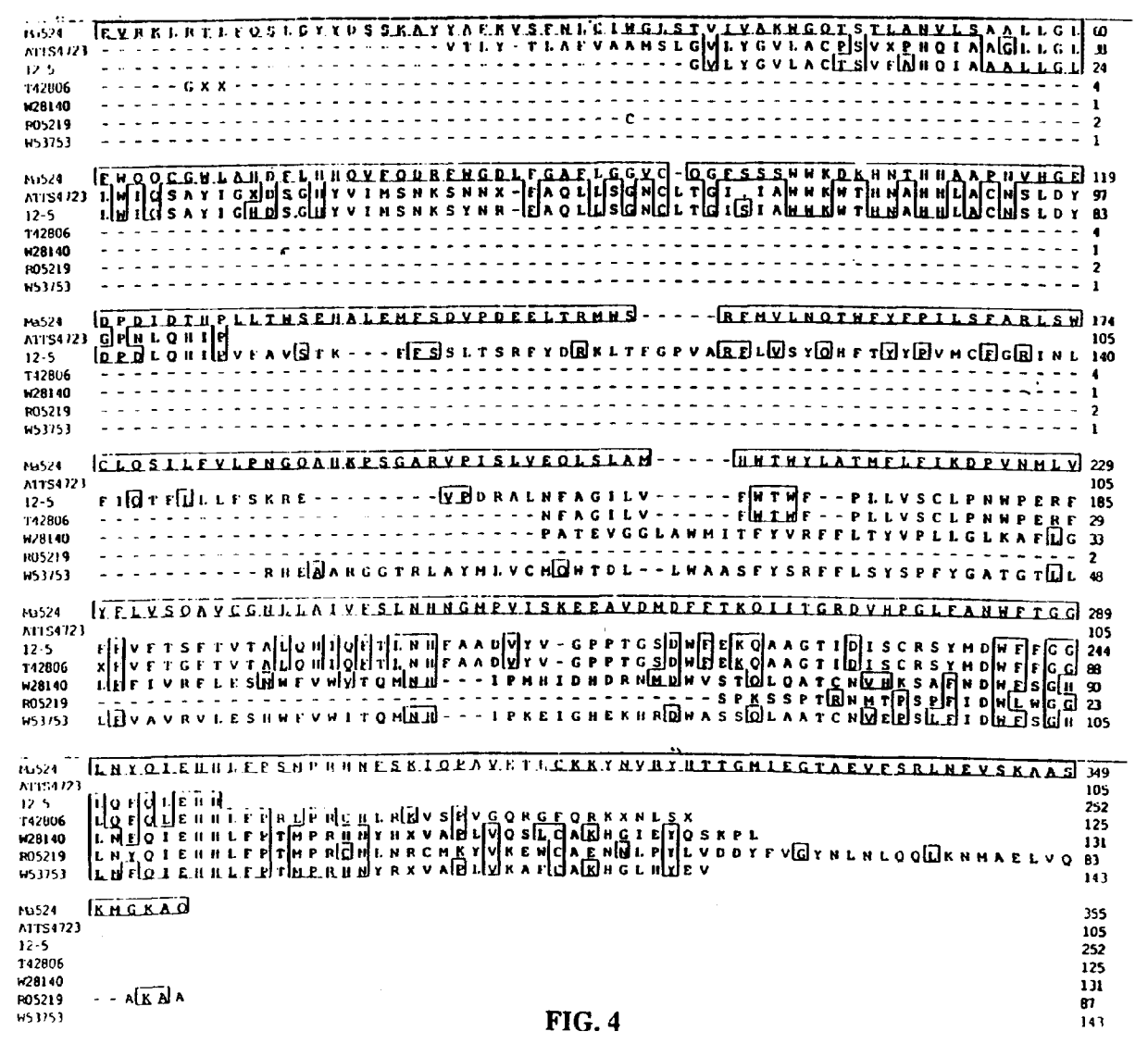

Identification of Δ6-Desaturases Homologous to the *Mortierella alpina* Δ6-Desaturase Nucleic acid sequences that encode putative Δ6-desaturases were identified through a BLASTX search of the Expressed Sequence Tag ("EST") databases through NCBI using the Ma524 amino acid sequence. Several sequences showed significant homology. In particular, the deduced amino acid sequence of two *Arabidopsis thaliana* sequences, (accession numbers F13728 and T42806) showed homology to two different regions of the deduced amino acid sequence of Ma524. The following PCR primers were designed: ATTS4723-FOR (complementary to F13728) SEQ ID NO:13 5' CUACUACUACUAGGAGTCCTCTACGGTGTTTTG and T42806-REV (complementary to T42806) SEQ ID NO:14 5' CAUCAUCAUCAUATGATGCTCAAGCTGAAACTG. Five μg of total RNA isolated from developing siliques of *Arabidopsis thaliana* was reverse transcribed using BRL Superscript RTase and the primer TSyn (5'-CCAAGCTTCTGCAGGAGCTCTTTTTTTTTTTTTTT-3') and is shown as SEQ ID NO:12. PCR was carried out in a 50 ul volume containing: template derived from 25 ng total RNA, 2 pM each primer, 200 μM each deoxyribonucleotide triphosphate, 60 mM Tris-Cl, pH 8.5, 15 mM $(NH_4)_2SO_4$, 2 mM $MgCl_2$, 0.2 U Taq Polymerase. Thermocycler conditions were as follows: 94 degrees for 30 sec., 50 degrees for 30 sec., 72 degrees for 30 sec. PCR was continued for 35 cycles followed by an additional extension at 72 degrees for 7 minutes. PCR resulted in a fragment of approximately ~750 base pairs which was subcloned, named 12-5, and sequenced. Each end of this fragment was formed to correspond to the *Arabidopsis* ESTs from which the PCR primers were designed. The putative amino acid sequence of 12-5 was compared to that of Ma524, and ESTs from human (W28140), mouse (W53753), and *C. elegans* (R05219) (see FIG. 4). Homology patterns with the *Mortierella* Δ6-desaturase indicate that these sequences represent putative desaturase polypeptides. Based on this experiment approach, it is likely that the full-length genes can be cloned using probes based on the EST sequences. Following the cloning, the genes can then be placed into expression vectors, expressed in host cells, and their specific Δ6- or other desaturase activity can be determined as described below.

Example 4

Isolation of a Δ12-Desaturase Nucleotide Sequence from *Mortierella alpina*

Based on the fatty acids it accumulates, it seemed probable that *Mortierella alpina* has an ω6 type desaturase. The ω6-desaturase is responsible for the production of linoleic acid (18:2) from oleic acid (18:1). Linoleic acid (18:2) is a substrate for a Δ6-desaturase. This experiment was designed to determine if *Mortierella alpina* has a Δ12-desaturase polypeptide, and if so, to identify the corresponding nucleotide sequence.

A random colony from the *M. alpina* sequencing grade library, Ma648, was sequenced and identified as a putative desaturase based on DNA sequence homology to previously identified desaturases, as described for Ma524 (see Example 2). The nucleotide sequence is shown in SEQ ID NO:13. The peptide sequence is shown in SEQ ID NO:4. The deduced amino acid sequence from the 5' end of the Ma648 cDNA displays significant homology to soybean microsomal ω6

(Δ12) desaturase (accession #L43921) as well as castor bean oleate 12-hydroxylase (accession #U22378). In addition, homology was observed when compared to a variety of other ω6 (Δ12) and ω3 (Δ15) fatty acid desaturase sequences.

Example 5

Expression of *M. alpina* Desaturase Clones in Baker's Yeast

Yeast Transformation

Lithium acetate transformation of yeast was performed according to standard protocols (*Methods in Enzymology*, Vol. 194, p. 186-187, 1991). Briefly, yeast were grown in YPD at 30° C. Cells were spun down, resuspended in TE, spun down again, resuspended in TE containing 100 mM lithium acetate, spun down again, and resuspended in TE/lithium acetate. The resuspended yeast were incubated at 30° C. for 60 minutes with shaking. Carrier DNA was added, and the yeast were aliquoted into tubes. Transforming DNA was added, and the tubes were incubated for 30 min. at 30° C. PEG solution (35% (w/v) PEG 4000, 100 mM lithium acetate, TE pH7.5) was added followed by a 50 min. incubation at 30° C. A 5 min. heat shock at 42° C. was performed, the cells were pelleted, washed with TE, pelleted again and resuspended in TE. The resuspended cells were then plated on selective media.

Desaturase Expression in Transformed Yeast cDNA clones from *Mortierella alpina* were screened for desaturase activity in baker's yeast. A canola Δ15-desaturase (obtained by PCR using 1$^{st}$ strand cDNA from *Brassica napus* cultivar 212/86 seeds using primers based on the published sequence (Arondel et al. *Science* 258:1353-1355)) was used as a positive control. The Δ15-desaturase gene and the gene from cDNA clones Ma524 and Ma648 were put in the expression vector pYES2 (Invitrogen), resulting in plasmids pCGR-2, pCGR-5 and pCGR-7, respectively. These plasmids were transfected into *S. cerevisiae* yeast strain 334 and expressed after induction with galactose and in the presence of substrates that allowed detection of specific desaturase activity. The control strain was *S. cerevisiae* strain 334 containing the unaltered pYES2 vector. The substrates used, the products produced and the indicated desaturase activity were: DGLA (conversion to ARA would indicate Δ5-desaturase activity), linoleic acid (conversion to GLA would indicate Δ6-desaturase activity; conversion to ALA would indicate Δ15-desaturase activity), oleic acid (an endogenous substrate made by *S. cerevisiae*, conversion to linoleic acid would indicate Δ12-desaturase activity, which *S. cerevisiae* lacks), or ARA (conversion to EPA would indicate Δ17-desaturase activity).

Cultures were grown for 48-52 hours at 15° C. in the presence of a particular substrate. Lipid fractions were extracted for analysis as follows: Cells were pelleted by centrifugation, washed once with sterile $ddH_20$, and repelleted. Pellets were vortexed with methanol; chloroform was added along with tritridecanoin (as an internal standard). The mixtures were incubated for at least one hour at room temperature or at 4° C. overnight. The chloroform layer was extracted and filtered through a Whatman filter with one gram of anhydrous sodium sulfate to remove particulates and residual water. The organic solvents were evaporated at 40° C. under a stream of nitrogen. The extracted lipids were then derivatized to fatty acid methyl esters (FAME) for gas chromatography analysis (GC) by adding 2 ml of 0.5 N potassium hydroxide in methanol to a closed tube. The samples were heated to 95° C. to 100° C. for 30 minutes and cooled to room temperature. Approximately 2 ml of 14% boron trifluoride in methanol was added and the heating repeated. After the extracted lipid mixture cooled, 2 ml of water and 1 ml of hexane were added to extract the FAME for analysis by GC. The percent conversion was calculated by dividing the product produced by the sum of (the product produced and the substrate added) and then multiplying by 100. To calculate the oleic acid percent conversion, as no substrate was added, the total linoleic acid produced was divided by the sum of oleic acid and linoleic acid produced, then multiplying by 100. The desaturase activity results are provided in Table 1 below.

TABLE 1

*M. alpina* Desaturase Expression in Baker's Yeast

| CLONE | ENZYME ACTIVITY | % CONVERSION OF SUBSTRATE |
|---|---|---|
| pCGR-2 | Δ6 | 0 (18:2 to 18:3w6) |
| (canola Δ15 | Δ15 | 16.3 (18:2 to 18:3w3) |
| desaturase) | Δ5 | 2.0 (20:3 to 20:4w6) |
| | Δ17 | 2.8 (20:4 to 20:5w3) |
| | Δ12 | 1.8 (18:1 to 18:2w6) |
| pCGR-5 | Δ6 | 6.0 |
| (*M. alpina* | Δ15 | 0 |
| Ma524 | Δ5 | 2.1 |
| | Δ17 | 0 |
| | Δ12 | 3.3 |
| pCGR-7 | Δ6 | 0 |
| (*M. alpina* | Δ15 | 3.8 |
| Ma648 | Δ5 | 2.2 |
| | Δ17 | 0 |
| | Δ12 | 63.4 |

The Δ15-desaturase control clone exhibited 16.3% conversion of the substrate. The pCGR-5 clone expressing the Ma524 cDNA showed 6% conversion of the substrate to GLA, indicating that the gene encodes a Δ6-desaturase. The pCGR-7 clone expressing the Ma648 cDNA converted 63.4% conversion of the substrate to LA, indicating that the gene encodes a Δ12-desaturase. The background (non-specific conversion of substrate) was between 0-3% in these cases. We also found substrate inhibition of the activity by using different concentrations of the substrate. When substrate was added to 100 μM, the percent conversion to product dropped compared to when substrate was added to 25 μM (see below). Additionally, by varying the substrate concentration between 5 μM and 200 μM, conversion ratios were found to range between about 5% to about 75% greater. These data show that desaturases with different substrate specificities can be expressed in a heterologous system and used to produce polyunsaturated long chain fatty acids.

Table 2 represents fatty acids of interest as a percent of the total lipid extracted from the yeast host *S. cerevisiae* 334 with the indicated plasmid. No glucose was present in the growth media. Affinity gas chromatography was used to separate the respective lipids. GC/MS was employed to verify the identity of the product(s). The expected product for the *B. napus* Δ15-desaturase, α-linolenic acid, was detected when its substrate, linoleic acid, was added exogenously to the induced yeast culture. This finding demonstrates that yeast expression of a desaturase gene can produce functional enzyme and detectable amounts of product under the current growth conditions. Both exogenously added substrates were taken up by yeast, although slightly less of the longer chain PUFA, dihomo-γ-linolenic acid (20:3), was incorporated into yeast than linoleic acid (18:2) when either was added in free form to the induced yeast cultures. γ-linolenic acid was detected when linoleic acid was present during induction and expression of *S. cerevisiae* 334 (pCGR-5). The presence of this PUFA demonstrates Δ6-desaturase activity from pCGR-5 (MA524). Linoleic acid, identified in the extracted lipids from expression of *S. cerevisiae* 334 (pCGR-7), classifies the cDNA MA648 from *M. alpina* as the Δ12-desaturase.

TABLE 2

| Fatty Acid as a Percentage of Total Lipid Extracted from Yeast | | | | | | | |
|---|---|---|---|---|---|---|---|
| Plasmid in Yeast (enzyme) | 18:2 Incorporated | α-18:3 Produced | γ-18:3 Produced | 20:3 Incorporated | 20:4 Produced | 18:1* Present | 18:2 Produced |
| pYES2 (control) | 66.9 | 0 | 0 | 58.4 | 0 | 4 | 0 |
| pCGR-2 (Δ15) | 60.1 | 5.7 | 0 | 50.4 | 0 | 0.7 | 0 |
| pCGR-5 (Δ6) | 62.4 | 0 | 4.0 | 49.9 | 0 | 2.4 | 0 |
| pCGR-7 (Δ12) | 65.6 | 0 | 0 | 45.7 | 0 | 7.1 | 12.2 |

100 μM substrate added
*18:1 is an endogenous fatty acid in yeast
Key To Tables
18:1 = oleic acid
18:2 = linoleic acid
α-18:3 = α-linolenic acid
γ-18:3 = γ-linolenic acid
18:4 = stearidonic acid
20:3 = dihomo-γ-linolenic acid
20:4 = arachidonic acid

Example 6

Optimization of Culture Conditions

Table 3A shows the effect of exogenous free fatty acid substrate concentration on yeast uptake and conversion to fatty acid product as a percentage of the total yeast lipid extracted. In all instances, low amounts of exogenous substrate (1-10 μM) resulted in low fatty acid substrate uptake and product formation. Between 25 and 50 μM concentration of free fatty acid in the growth and induction media gave the highest percentage of fatty acid product formed, while the 100 μM concentration and subsequent high uptake into yeast appeared to decrease or inhibit the desaturase activity. The amount of fatty acid substrate for yeast expressing Δ12-desaturase was similar under the same growth conditions, since the substrate, oleic acid, is an endogenous yeast fatty acid. The use of α-linolenic acid as an additional substrate for pCGR-5 (Δ6) produced the expected product, stearidonic acid (Table 3A). The feedback inhibition of high fatty acid substrate concentration was well illustrated when the percent conversion rates of the respective fatty acid substrates to their respective products were compared in Table 3B. In all cases, 100 μM substrate concentration in the growth media decreased the percent conversion to product. The uptake of α-linolenic was comparable to other PUFAs added in free form, while the Δ6-desaturase percent conversion, 3.8-17.5%, to the product stearidonic acid was the lowest of all the substrates examined (Table 3B). The effect of media, such as YPD (rich media) versus minimal media with glucose on the conversion rate of Δ12-desaturase was dramatic. Not only did the conversion rate for oleic to linoleic acid drop, (Table 3B) but the percent of linoleic acid formed also decreased by 11% when rich media was used for growth and induction of yeast desaturase Δ12 expression (Table 3A). The effect of media composition was also evident when glucose was present in the growth media for Δ6-desaturase, since the percent of substrate uptake was decreased at 25 μM (Table 3A). However, the conversion rate remained the same and percent product formed decreased for Δ6-desaturase for in the presence of glucose.

TABLE 3A

| Effect of Added Substrate on the Percentage of Incorporated Substrate and Product Formed in Yeast Extracts | | | | |
|---|---|---|---|---|
| | Plasmid in Yeast | | | |
| | pCGR-2 (Δ15) | PcGR-5 (Δ6) | pCGR-5 (Δ6) | pCGR-7 (Δ12) |
| Substrate/ product | 18:2/α-18:3 | 18:2/γ-18:3 | α-18:3/18:4 | 18:1*/18:2 |
| 1 μM sub. | ND | 0.9/0.7 | ND | ND |
| 10 μM sub. | ND | 4.2/2.4 | 10.4/2.2 | ND |
| 25 μM sub. | ND | 11/3.7 | 18.2/2.7 | ND |
| 25 μM ◇ sub. | 36.6/7.2 ◇ | 25.1/10.3 ◇ | ND | 6.6/15.8 ◇ |
| 50 μM sub. | 53.1/6.5 ◇ | ND | 36.2/3 | 10.8/13+ |
| 100 μM sub. | 60.1/5.7 ◇ | 62.4/4 ◇ | 47.7/1.9 | 10/24.8 |

TABLE 3B

| Effect of Substrate Concentration in Media on the Percent Conversion of Fatty Acid Substrate to Product in Yeast Extracts | | | | |
|---|---|---|---|---|
| | Plasmid in Yeast | | | |
| | pCGR-2 (Δ15) | pCGR-5 (Δ6) | pCGR-5 (Δ6) | pCGR-7 (Δ12) |
| substrate→product | 18:2 →α-18:3 | 18:2→γ18:3 | α-18:3→18:4 | 18:1*→18:2 |
| 1 μM sub. | ND | 43.8 | ND | ND |
| 10 μM sub. | ND | 36.4 | 17.5 | ND |
| 25 μM sub. | ND | 25.2 | 12.9 | ND |
| 25 μM ◇ sub. | 16.4 ◇ | 29.1 ◇ | ND | 70.5 ◇ |

TABLE 3B-continued

| Effect of Substrate Concentration in Media on the Percent Conversion of Fatty Acid Substrate to Product in Yeast Extracts | | | | |
|---|---|---|---|---|
| | Plasmid in Yeast | | | |
| | pCGR-2 (Δ15) | pCGR-5 (Δ6) | pCGR-5 (Δ6) | pCGR-7 (Δ12) |
| 50 μM sub. | 10.9 ◇ | ND | 7.7 | 54.6⁺ |
| 100 μM sub. | 8.7 ◇ | 6 ◇ | 3.8 | 71.3 |

◇ no glucose in media
⁺Yeast peptone broth (YPD)
*18:1 is an endogenous yeast lipid
sub. is substrate concentration
ND (not done)

Table 4 shows the amount of fatty acid produced by a recombinant desaturase from induced yeast cultures when different amounts of free fatty acid substrate were used. Fatty acid weight was determined since the total amount of lipid varied dramatically when the growth conditions were changed, such as the presence of glucose in the yeast growth and induction media. To better determine the conditions when the recombinant desaturase would produce the most PUFA product, the quantity of individual fatty acids were examined. The absence of glucose dramatically reduced by three fold the amount of linoleic acid produced by recombinant Δ12-desaturase. For the Δ12-desaturase the amount of total yeast lipid was decreased by almost half in the absence of glucose. Conversely, the presence of glucose in the yeast growth media for Δ6-desaturase drops the γ-linolenic acid produced by almost half, while the total amount of yeast lipid produced was not changed by the presence/absence of glucose. This points to a possible role for glucose as a modulator of Δ6-desaturase activity.

TABLE 4

| Fatty Acid Produced in μg from Yeast Extracts | | | |
|---|---|---|---|
| | Plasmid in Yeast (enzyme) | | |
| | pCGR-5 (Δ6) | pCGR-5 (Δ6) | pCGR-7 (Δ12) |
| product | Y-18:3 | 18:4 | 18:2* |
| 1 μM sub. | 1.9 | ND | ND |
| 10 μM sub. | 5.3 | 4.4 | ND |

TABLE 4-continued

| Fatty Acid Produced in μg from Yeast Extracts | | | |
|---|---|---|---|
| | Plasmid in Yeast (enzyme) | | |
| | pCGR-5 (Δ6) | pCGR-5 (Δ6) | pCGR-7 (Δ12) |
| 25 μM sub. | 10.3 | 8.7 | 115.7 |
| 25 μM ◇ sub. | 29.6 | ND | 39 ◇ |

◇ no glucose in media
sub. is substrate concentration
ND (not done)
*18:1, the substrate, is an endogenous yeast lipid

Example 7

Distribution of PUFAs in Yeast Lipid Fractions

Table 5 illustrates the uptake of free fatty acids and their new products formed in yeast lipids as distributed in the major lipid fractions. A total lipid extract was prepared as described above. The lipid extract was separated on TLC plates, and the fractions were identified by comparison to standards. The bands were collected by scraping, and internal standards were added. The fractions were then saponified and methylated as above, and subjected to gas chromatography. The gas chromatograph calculated the amount of fatty acid by comparison to a standard. The phospholipid fraction contained the highest amount of substrate and product PUFAs for Δ6-desaturase activity. It would appear that the substrates are accessible in the phospholipid form to the desaturases.

TABLE 5

Fatty Acid Distribution in Various Yeast Lipid Fractions in μg

| Fatty acid fraction | Phospholipid | Diglyceride | Free Fatty Acid | Triglyceride | Cholesterol Ester |
|---|---|---|---|---|---|
| SC (pCGR-5) substrate 18:2 | 166.6 | 6.2 | 15 | 18.2 | 15.6 |
| SC (pCGR-5) product γ-18:3 | 61.7 | 1.6 | 4.2 | 5.9 | 1.2 |

SC = *S. cerevisiae* (plasmid)

Example 8

Further Culture Optimization and Coexpression of Δ6 and Δ12-Desaturases

This experiment was designed to evaluate the growth and induction conditions for optimal activities of desaturases in *Saccharomyces cerevisiae*. A *Saccharomyces cerevisiae* strain (SC334) capable of producing γ-linolenic acid (GLA) was developed, to assess the feasibility of production of PUFA in yeast. The genes for Δ6 and Δ12-desaturases from *M. alpina* were coexpressed in SC334. Expression of Δ12-desaturase converted oleic acid (present in yeast) to linoleic acid. The linoleic acid was used as a substrate by the Δ6-desaturase to produce GLA. The quantity of GLA produced ranged between 5-8% of the total fatty acids produced in SC334 cultures and the conversion rate of linoleic acid to γ-linolenic acid ranged between 30% to 50%. The induction temperature was optimized, and the effect of changing host strain and upstream promoter sequences on expression of Δ6 and Δ12 (MA 524 and MA 648 respectively) desaturase genes was also determined.

Plasmid Construction

The cloning of pCGR5 as well as pCGR7 has been discussed above. To construct pCGR9a and pCGR9b, the Δ6 and Δ12-desaturase genes were amplified using the following sets of primers. The primers pRDS1 and 3 had Xho1 site and primers pRDS2 and 4 had Xba1 site (indicated in bold). These primer sequences are presented as SEQ ID NO:15-18.

I. Δ6-Desaturase Amplification Primers (SEQ ID NO: 15)
a. pRDS1 TAC CAA CTC GAG AAA ATG GCT GCT GCT CCC AGT GTG AGG (SEQ ID NO: 16)
b. pRDS2 AAC TGA TCT AGA TTA CTG CGC CTT ACC CAT CTT GGA GGC II. Δ12-Desaturase Amplification Primers (SEQ ID NO: 17)
a. pRDS3 TAC CAA CTC GAG AAA ATG GCA CCT CCC AAC ACT ATC GAT (SEQ ID NO: 18)
b. pRDS4 AAC TGA TCT AGA TTA CTT CTT GAA AAA GAC CAC GTC TCC The pCGR5 and pCGR7 constructs were used as template DNA for amplification of Δ6 and Δ12-desaturase genes, respectively. The amplified products were digested with Xba1 and XhoI to create “sticky ends”. The PCR amplified Δ6-desaturase with Xho1-Xba1 ends as cloned into pCGR7, which was also cut with Xho-1-Xba1. This procedure placed the Δ6-desaturase behind the Δ12-desaturase, under the control of an inducible promoter GAL1. This construct was designated pCGR9a. Similarly, to construct pCGR9b, the Δ12-desaturase with XhoI-XbaI ends was cloned in the XhoI-XbaI sites of pCGR5. In pCGR9b the Δ12-desaturase was behind the Δ6-desaturase gene, away from the GAL promoter.

To construct pCGR10, the vector pRS425, which contains the constitutive Glyceraldehyde 3-Phosphate Dehydrogenase (GPD) promoter, was digested with BamH1 and pCGR5 was digested with BamH1-Xho1 to release the Δ6-desaturase gene. This Δ6-desaturase fragment and BamH1 cut pRS425 were filled using Klenow Polymerase to create blunt ends and ligated, resulting in pCGR10a and pCGR10b containing the Δ6-desaturase gene in the sense and antisense orientation, respectively. To construct pCGR11 and pCGR12, the Δ6 and Δ12-desaturase genes were isolated from pCGR5 and pCGR7, respectively, using an EcoR1-XhoI double digest. The EcoR1-Xho1 fragments of Δ6 and Δ12-desaturases were cloned into the pYX242 vector digested with EcoR1-Xho1. The pYX242 vector has the promoter of TP1 (a yeast housekeeping gene), which allows constitutive expression.

Yeast Transformation and Expression

Different combinations of pCGR5, pCGR7, pCGR9a, pCGR9b, pCGR10a, pCGR11 and pCGR12 were introduced into various host strains of *Saccharomyces cerevisiae*. Transformation was done using PEG/LiAc protocol (Methods in Enzymology Vol. 194 (1991): 186-187). Transformants were selected by plating on synthetic media lacking the appropriate amino acid. The pCGR5, pCGR7, pCGR9a and pCGR9b can be selected on media lacking uracil. The pCGR10, pCGR11 and pCGR12 constructs can be selected on media lacking leucine. Growth of cultures and fatty acid analysis was performed as in Example 5 above.

Production of GLA

Production of GLA requires the expression of two enzymes (the Δ6 and Δ12-desaturases), which are absent in yeast. To express these enzymes at optimum levels the following constructs or combinations of constructs, were introduced into various host strains:

1) pCGR9a/SC334
2) pCGR9b/SC334
3) pCGR10a and pCGR7/SC334
4) pCGR11 and pCGR7/SC334
5) pCGR12 and pCGR5/SC334
6) pCGR10a and pCGR7/DBY746
7) pCGR10a and pCGR7/DBY746

The pCGR9a construct has both the Δ6 and Δ12-desaturase genes under the control of an inducible GAL promoter. The SC334 host cells transformed with this construct did not show any GLA accumulation in total fatty acids (FIGS. 6A and B, lane 1). However, when the Δ6 and Δ12-desaturase genes were individually controlled by the GAL promoter, the control constructs were able to express Δ6- and Δ12-desaturase, as evidenced by the conversion of their respective substrates to products. The Δ12-desaturase gene in pCGR9a was expressed as evidenced by the conversion of 18:1ω9 to 18:2ω6 in pCGR9a/SC334, while the Δ6-desaturase gene was not expressed/active, because the 18:2ω6 was not being converted to 18:3ω6 (FIGS. 6A and B, lane 1).

The pCGR9b construct also had both the Δ6 and Δ12-desaturase genes under the control of the GAL promoter but in an inverse order compared to pCGR9a. In this case, very little GLA (<1%) was seen in pCGR9b/SC334 cultures. The expression of Δ12-desaturase was also very low, as evidenced by the low percentage of 18:2ω6 in the total fatty acids (FIGS. 6A and B, lane 1).

Figure 6:
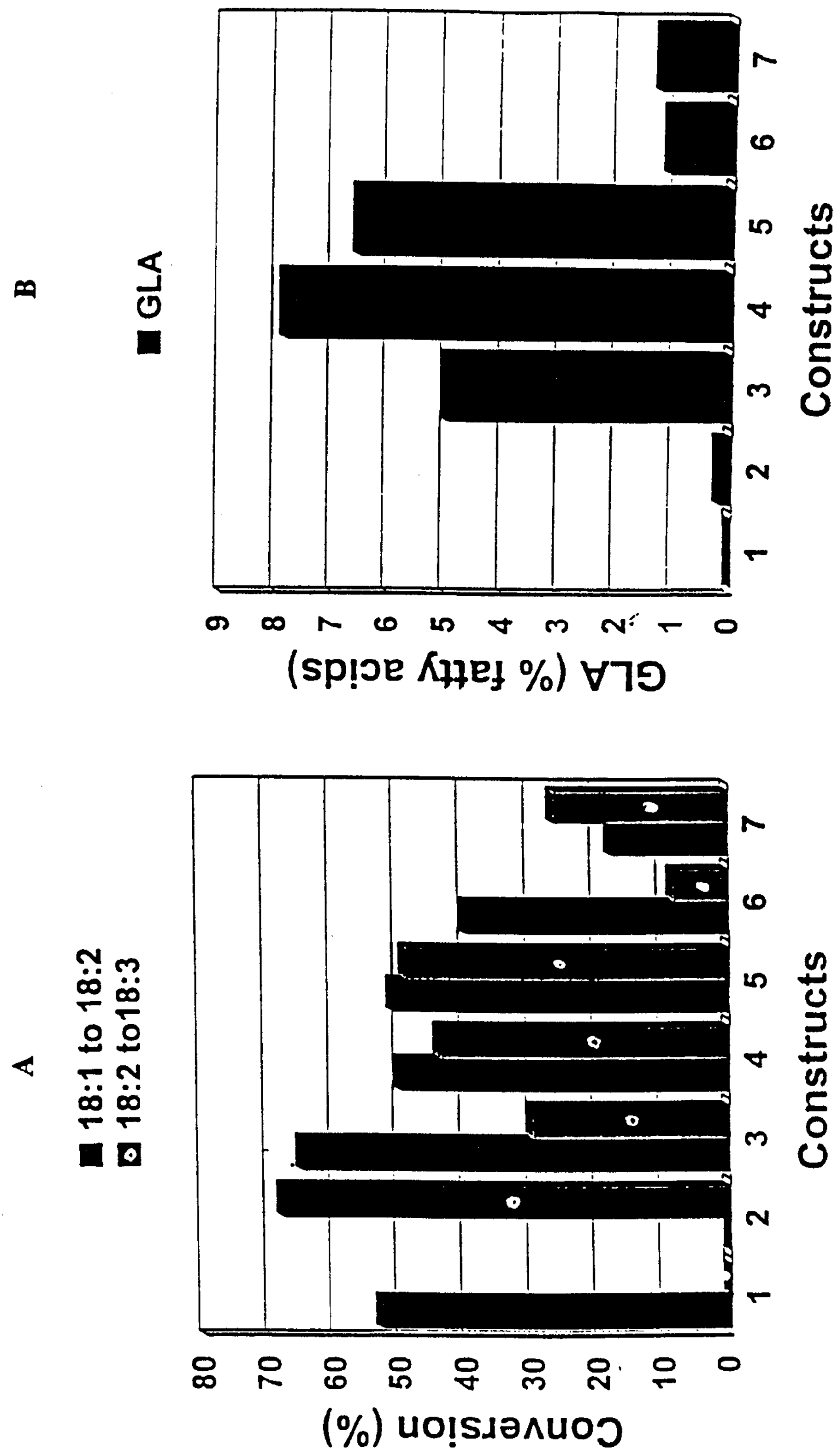
FIGS. 6A and 6B show the effect of different expression constructs on expression of GLA in yeast.

To test if expressing both enzymes under the control of independent promoters would increase GLA production, the Δ6-desaturase gene was cloned into the pRS425 vector. The construct of pCGR10a has the Δ6-desaturase in the correct orientation, under control of constitutive GPD promoter. The pCGR10b has the Δ6-desaturase gene in the inverse orientation, and serves as the negative control. The pCGR10a/SC334 cells produced significantly higher levels of GLA (5% of the total fatty acids, FIG. 6, lane 3), compared to pCGR9a. Both the Δ6 and Δ12-desaturase genes were expressed at high level because the conversion of 18:1ω9→18:2ω6 was 65%, while the conversion of 18:2ω6→18:3ω6 (Δ6-desaturase) was 30% (FIG. 6, lane 3). As expected, the negative control pCGR10b/SC334 did not show any GLA.

To further optimize GLA production, the Δ6 and Δ12 genes were introduced into the pYX242 vector, creating pCGR11 and pCGR12 respectively. The pYX242 vector allows for constitutive expression by the TP1 promoter (Alber, T. and Kawasaki, G. (1982). *J. Mol. & Appl. Genetics* 1: 419). The introduction of pCGR11 and pCGR7 in SC334 resulted in approximately 8% of GLA in total fatty acids of SC334. The rate of conversion of 18:1ω9→18:2ω6 and 18:2ω6→18:3ω6 was approximately 50% and 44% respectively (FIGS. 6A and B, lane 4). The presence of pCGR12 and pCGR5 in SC334 resulted in 6.6% GLA in total fatty acids with a conversion rate of approximately 50% for both 18:1ω9 to 18:2ω6 and 18:2ω6 to 18:3ω6, respectively (FIGS. 6A and B, lane 5). Thus although the quantity of GLA in total fatty acids was higher in the pCGR11/pCGR7 combination of constructs, the conversion rates of substrate to product were better for the pCGR12/pCGR5 combination.

Figure 7:
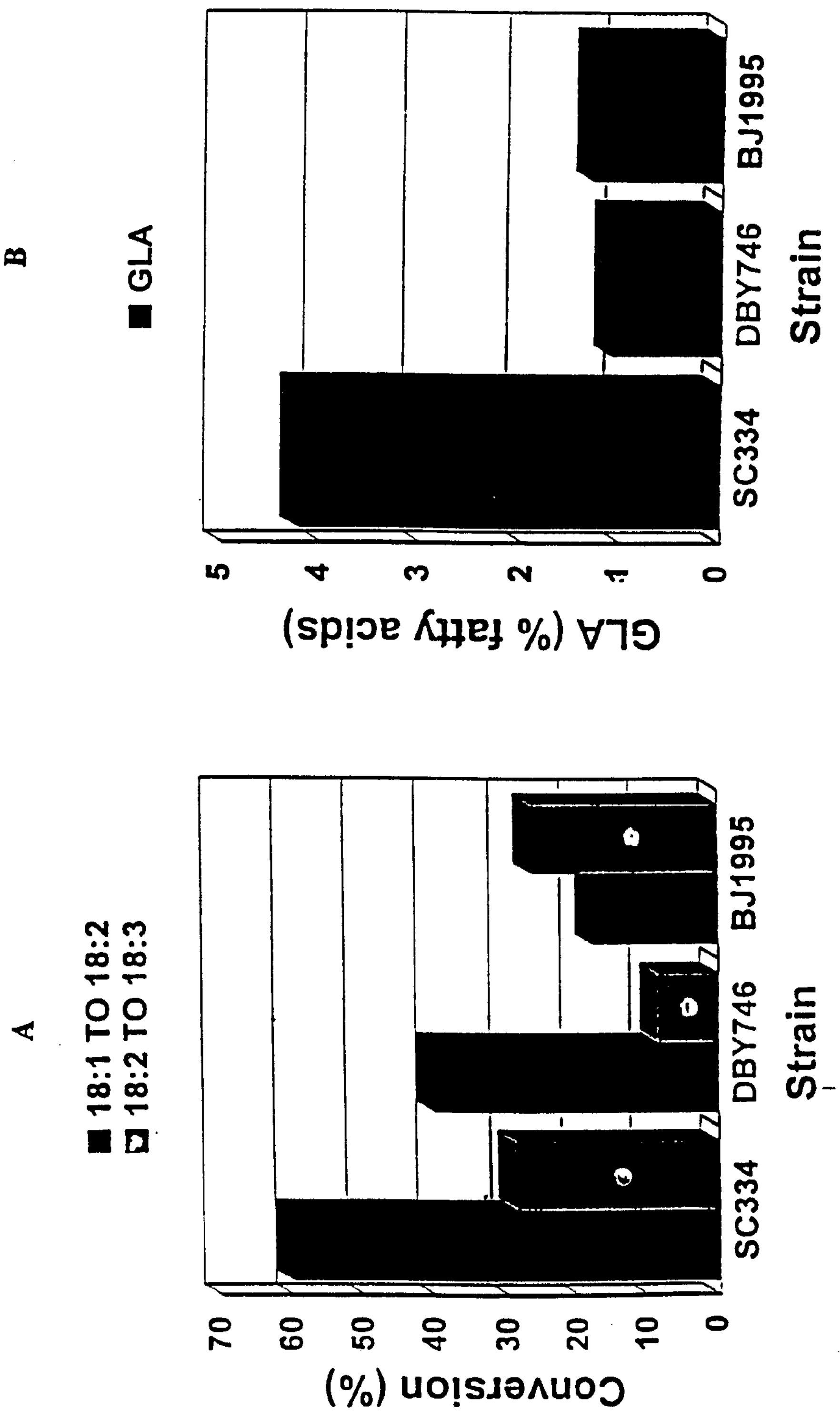
FIGS. 7A and 7B show the effect of host strain on GLA production.

To determine if changing host strain would increase GLA production, pCGR10a and pCGR7 were introduced into the host strain BJ1995 and DBY746 (obtained from the Yeast Genetic Stock Centre, 1021 Donner Laboratory, Berkeley, Calif. 94720. The genotype of strain DBY746 is Matα, his3-Δ1, leu2-3, leu2-112, ura3-32, trp1-289, gal). The results are shown in FIG. 7. Changing host strain to BJ1995 did not improve the GLA production, because the quantity of GLA was only 1.31% of total fatty acids and the conversion rate of 18:1ω9→18:2ω6 was approximately 17% in BJ1995. No GLA was observed in DBY746 and the conversion of 18:1ω9→18:2ω6 was very low (<1% in control) suggesting that a cofactor required for the expression of Δ12-desaturase might be missing in DB746 (FIG. 7, lane 2).

Figure 8:
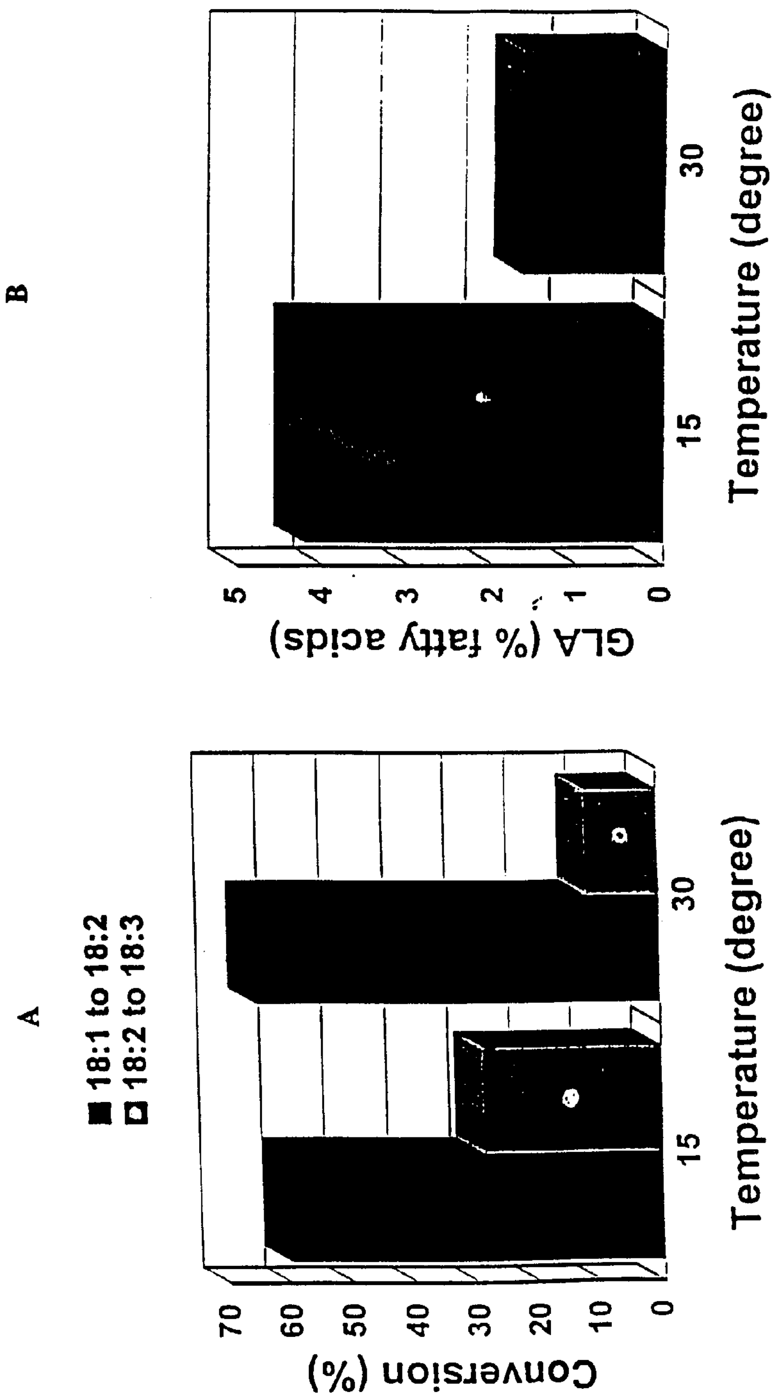
FIGS. 8A and 8B show the effect of temperature on GLA production in *S. cerevisiae* strain SC334.

To determine the effect of temperature on GLA production, SC334 cultures containing pCGR10a and pCGR7 were grown at 15° C. and 30° C. Higher levels of GLA were found in cultures grown and induced at 15° C. than those in cultures grown at 30° C. (4.23% vs. 1.68%). This was due to a lower conversion rate of 18:2ω6→18:3ω6 at 30° C. (11.6% vs. 29% in 15° C.) cultures, despite a higher conversion of 18:1ω9→18:2ω6 (65% vs. 60% at 30° C. (FIG. 8). These results suggest that Δ12- and Δ6-desaturases may have different optimal expression temperatures.

Of the various parameters examined in this study, temperature of growth, yeast host strain and media components had the most significant impact on the expression of desaturase, while timing of substrate addition and concentration of inducer did not significantly affect desaturase expression.

These data show that two DNAs encoding desaturases that can convert LA to GLA or oleic acid to LA can be isolated from *Mortierella alpina* and can be expressed, either individually or in combination, in a heterologous system and used to produce poly-unsaturated long chain fatty acids. Exemplified is the production of GLA from oleic acid by expression of Δ12- and Δ6-desaturases in yeast.

Example 9

Identification of Homologues to *M. Alpina* Δ5 and Δ6 Desaturases

A nucleic acid sequence that encodes a putative Δ5 desaturase was identified through a TBLASTN search of the expressed sequence tag databases through NCBI using amino acids 100-446 of Ma29 as a query. The truncated portion of the Ma29 sequence was used to avoid picking up homologies based on the cytochrome b5 portion at the N-terminus of the desaturase. The deduced amino acid sequence of an est from *Dictyostelium discoideum* (accession # C25549) shows very significant homology to Ma29 and lesser, but still significant homology to Ma524. The DNA sequence is presented as SEQ ID NO:19. The amino acid sequence is presented as SEQ ID NO:20.

Example 10

Identification of *M. Alpina* Δ5 and Δ6 Homologues in Other PUFA-Producing Organisms To look for desaturases involved in PUFA production, a cDNA library was constructed from total RNA isolated from *Phaeodactylum tricornutum*. A plasmid-based cDNA library was constructed in pSPORT1 (GIBCO-BRL) following manufacturer's instructions using a commercially available kit (GIBCO-BRL). Random cDNA clones were sequenced and nucleic acid sequences that encode putative Δ5 or Δ6 desaturases were identified through BLAST search of the databases and comparison to Ma29 and Ma524 sequences.

One clone was identified from the *Phaeodactylum* library with homology to Ma29 and Ma524; it is called 144-011-B12. The DNA sequence is presented as SEQ ID NO:21. The amino acid sequence is presented as SEQ ID NO:22.

Example 11

Identification of *M. Alpina* Δ5 and Δ6 Homologues in Other PUFA-Producing Organisms To look for desaturases involved in PUFA production, a cDNA library was constructed from total RNA isolated from *Schizochytrium* species. A plasmid-based cDNA library was constructed in pSPORT1 (GIBCO-BRL) following manufacturer's instructions using a commercially available kit (GIBCO-BRL). Random cDNA clones were sequenced and nucleic acid sequences that encode putative Δ5 or Δ6 desaturases were identified through BLAST search of the databases and comparison to Ma29 and Ma524 sequences.

One clone was identified from the *Schizochytrium* library with homology to Ma29 and Ma524; it is called 81-23-C7. This clone contains a ~1 kb insert. Partial sequence was obtained from each end of the clone using the universal forward and reverse sequencing primers. The DNA sequence from the forward primer is presented as SEQ ID NO:23. The peptide sequence is presented as SEQ ID NO:24. The DNA sequence from the reverse primer is presented as SEQ ID NO:25. The amino acid sequence from the reverse primer is presented as SEQ ID NO:26.

Example 12

Human Desaturase Gene Sequences

Human desaturase gene sequences potentially involved in long chain polyunsaturated fatty acid biosynthesis were isolated based on homology between the human cDNA sequences and *Mortierella alpina* desaturase gene sequences. The three conserved "histidine boxes" known to be conserved among membrane-bound desaturases were found. As with some other membrane-bound desaturases the final HXXHH histidine box motif was found to be QXXHH. The amino acid sequence of the putative human desaturases exhibited homology to *M. alpina* Δ5, Δ6, Δ9, and Δ12 desaturases.

The *M. alpina* Δ5 desaturase and Δ6 desaturase cDNA sequences were used to search the LifeSeq database of Incyte Pharmaceuticals, Inc., Palo Alto, Calif. 94304. The Δ5 desaturase sequence was divided into fragments; 1) amino acid no. 1-150, 2) amino acid no. 151-300, and 3) amino acid no. 301-446. The Δ6 desaturase sequence was divided into three fragments; 1) amino acid no. 1-150, 2) amino acid no. 151-300, and 3) amino acid no. 301-457. These polypeptide fragments were searched against the database using the "tblastn" algorithm. This algorithm compares a protein query sequence against a nucleotide sequence database dynamically translated in all six reading frames (both strands).

The polypeptide fragments 2 and 3 of *M. alpina* Δ5 and Δ6 have homologies with the CloneID sequences as outlined in Table 6. The CloneID represents an individual sequence from the Incyte LifeSeq database. After the "tblastn" results have been reviewed, Clone Information was searched with the default settings of Stringency of >=50, and Productscore<=100 for different CloneID numbers. The Clone Information Results displayed the information including the ClusterID, CloneID, Library, HitID, Hit Description. When selected, the ClusterID number displayed the clone information of all the clones that belong in that ClusterID. The Assemble command assembles all of the CloneID which comprise the ClusterID. The following default settings were used for GCG (Genetics Computer Group, University of Wisconsin Biotechnology Center, Madison, Wis. 53705) Assembly:

| | |
|---|---|
| Word Size: | 7 |
| Minimum Overlap: | 14 |
| Stringency: | 0.8 |
| Minimum Identity: | 14 |
| Maximum Gap: | 10 |
| Gap Weight: | 8 |
| Length Weight: | 2 |

GCG Assembly Results displayed the contigs generated on the basis of sequence information within the CloneID. A contig is an alignment of DNA sequences based on areas of homology among these sequences. A new sequence (consensus sequence) was generated based on the aligned DNA sequences within a contig. The contig containing the CloneID was identified, and the ambiguous sites of the consensus sequence was edited based on the alignment of the CloneIDs (see SEQ ID NO:27-SEQ ID NO:32) to generate the best possible sequence. The procedure was repeated for all six CloneID listed in Table 6. This produced five unique contigs. The edited consensus sequences of the 5 contigs were imported into the Sequencher software program (Gene Codes Corporation, Ann Arbor, Mich. 48 105). These consensus sequences were assembled. The contig 2511785 overlaps with contig 3506132, and this new contig was called 2535 (SEQ ID NO:33). The contigs from the Sequencher program were copied into the Sequence Analysis software package of GCG.

Each contig was translated in all six reading frames into protein sequences. The *M. alpina* Δ5 (MA29) and Δ6 (MA524) sequences were compared with each of the translated contigs using the FastA search (a Pearson and Lipman search for similarity between a query sequence and a group of sequences of the same type (nucleic acid or protein)). Homology among these sequences suggest the open reading frames of each contig. The homology among the *M. alpina* Δ5 and Δ6 to contigs 2535 and 3854933 were utilized to create the final contig called 253538a. FIG. 13 is the FastA match of the final contig 253538a and MA29, and FIG. 14 is the FastA match of the final contig 253538a and MA524. The DNA sequences for the various contigs are presented in SEQ ID NO:27-SEQ ID NO:33 The various peptide sequences are shown in SEQ ID NO:34-SEQ ID NO: 40.

Although the open reading frame was generated by merging the two contigs, the contig 2535 shows that there is a unique sequence in the beginning of this contig which does not match with the contig 3854933. Therefore, it is possible that these contigs were generated from independent desaturase like human genes.

The contig 253538a contains an open reading frame encoding 432 amino acids. It starts with Gln (CAG) and ends with the stop codon (TGA). The contig 253538a aligns with both *M. alpina* Δ5 and Δ6 sequences, suggesting that it could be either of the desaturases, as well as other known desaturases which share homology with each other. The individual contigs listed in Table 18, as well as the intermediate contig 2535 and the final contig 253538a can be utilized to isolate the complete genes for human desaturases.

Uses of the Human Desaturases

These human sequences can be express in yeast and plants utilizing the procedures described in the preceding examples. For expression in mammalian cells transgenic animals, these genes may provide superior codon bias.

In addition, these sequences can be used to isolate related desaturase genes from other organisms.

TABLE 6

| Sections of the Desaturases | Clone ID from LifeSeq Database | Keyword |
|---|---|---|
| 151-300 Δ5 | 3808675 | fatty acid desaturase |
| 301-446 Δ5 | 354535 | Δ6 |
| 151-300 Δ6 | 3448789 | Δ6 |
| 151-300 Δ6 | 1362863 | Δ6 |
| 151-300 Δ6 | 2394760 | Δ6 |
| 301-457 Δ6 | 3350263 | Δ6 |

Example 13

I. Infant Formulations

A. Isomil® Soy Formula with Iron.

Usage: As a beverage for infants, children and adults with an allergy or sensitivity to cow's milk. A feeding for patients with disorders for which lactose should be avoided: lactase deficiency, lactose intolerance and galactosemia.

Features:

- Soy protein isolate to avoid symptoms of cow's-milk-protein allergy or sensitivity
- Lactose-free formulation to avoid lactose-associated diarrhea
- Low osmolality (240 mOsm/kg water) to reduce risk of osmotic diarrhea.
- Dual carbohydrates (corn syrup and sucrose) designed to enhance carbohydrate absorption and reduce the risk of exceeding the absorptive capacity of the damaged gut.
- 1.8 mg of Iron (as ferrous sulfate) per 100 Calories to help prevent iron deficiency.
- Recommended levels of vitamins and minerals.
- Vegetable oils to provide recommended levels of essential fatty acids.
- Milk-white color, milk-like consistency and pleasant aroma.

Ingredients: (Pareve, ®) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and disglycerides, soy lecithin, carrageenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin $D_3$ and cyanocobalamin.

B. Isomil® DF Soy Formula for Diarrhea.

Usage: As a short-term feeding for the dietary management of diarrhea in infants and toddlers.

Features:

- First infant formula to contain added dietary fiber from soy fiber specifically for diarrhea management.
- Clinically shown to reduce the duration of loose, watery stools during mild to severe diarrhea in infants.
- Nutritionally complete to meet the nutritional needs of the infant.
- Soy protein isolate with added L-methionine meets or exceeds an infant's requirement for all essential amino acids.
- Lactose-free formulation to avoid lactose-associated diarrhea.
- Low osmolality (240 mOsm/kg water) to reduce the risk of osmotic diarrhea.
- Dual carbohydrates (corn syrup and sucrose) designed to enhance carbohydrate absorption and reduce the risk of exceeding the absorptive capacity of the damaged gut.
- Meets or exceeds the vitamin and mineral levels recommended by the Committee on Nutrition of the American Academy of Pediatrics and required by the Infant Formula Act.
- 1.8 mg of iron (as ferrous sulfate) per 100 Calories to help prevent iron deficiency.
- Vegetable oils to provide recommended levels of essential fatty acids.

Ingredients: (Pareve, Ⓤ) 86% water, 4.8% corn syrup, 2.5% sugar (sucrose), 2.1% soy oil, 2.0% soy protein isolate, 1.4% coconut oil, 0.77% soy fiber, 0.12% calcium citrate, 0.11% calcium phosphate tribasic, 0.10% potassium citrate, potassium chloride, potassium phosphate monobasic, mono- and disglycerides, soy lecithin, carrageenan, magnesium chloride, ascorbic acid, L-methionine, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin $D_3$ and cyanocobalamin.

C. Isomil® SF Sucrose-Free Soy Formula with Iron.

Usage: As a beverage for infants, children and adults with an allergy or sensitivity to cow's-milk protein or an intolerance to sucrose. A feeding for patients with disorders for which lactose and sucrose should be avoided.

Features:

- Soy protein isolate to avoid symptoms of cow's-milk-protein allergy or sensitivity.
- Lactose-free formulation to avoid lactose-associated diarrhea (carbohydrate source is Polycose® Glucose Polymers).
- Sucrose free for the patient who cannot tolerate sucrose.
- Low osmolality (180 mOsm/kg water) to reduce risk of osmotic diarrhea.
- 1.8 mg of iron (as ferrous sulfate) per 100 Calories to help prevent iron deficiency.
- Recommended levels of vitamins and minerals.
- Vegetable oils to provide recommended levels of essential fatty acids.
- Milk-white color, milk-like consistency and pleasant aroma.

Ingredients: (Pareve, Ⓤ) 75% water, 11.8% hydrolized cornstarch, 4.1% soy oil, 4.1% soy protein isolate, 2.8% coconut oil, 1.0% modified cornstarch, 0.38% calcium phosphate tribasic, 0.17% potassium citrate, 0.13% potassium chloride, mono- and disglycerides, soy lecithin, magnesium chloride, abscorbic acid, L-methionine, calcium carbonate, sodium chloride, choline chloride; carrageenan, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin $D_3$ and cyanocobalamin.

D. Isomil® 20 Soy Formula with Iron Ready to Feed, 20 Cal/fl oz.

Usage: When a soy feeding is desired.

Ingredients: (Pareve, Ⓤ) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and disglycerides, soy lecithin, carrageenan, abscorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin $D_3$ and cyanocobalamin E. Similac® Infant Formula Usage: When an infant formula is needed: if the decision is made to discontinue breastfeeding before age 1 year, if a supplement to breastfeeding is needed or as a routine feeding if breastfeeding is not adopted.

Features:

- Protein of appropriate quality and quantity for good growth; heat-denatured, which reduces the risk of milk-associated enteric blood loss.
- Fat from a blend of vegetable oils (doubly homogenized), providing essential linoleic acid that is easily absorbed.
- Carbohydrate as lactose in proportion similar to that of human milk.
- Low renal solute load to minimize stress on developing organs.
- Powder, Concentrated Liquid and Ready To Feed forms.

Ingredients: (Ⓤ-D) Water, nonfat milk, lactose, soy oil, coconut oil, mono- and diglycerides, soy lecithin, abscorbic acid, carrageenan, choline chloride, taurine, m-inositol, alpha-tocopheryl acetate, zinc sulfate, niacinamid, ferrous sulfate, calcium pantothenate, cupric sulfate, vitamin A palmitate, thiamine chloride hydrochloride, riboflavin, pyridoxine hydrochloride, folic acid, manganese sulfate, phylloquinone, biotin, sodium selenite, vitamin $D_3$ and cyanocobalamin F. Similac® NeoCare Premature Infant Formula with Iron Usage: For premature infants' special nutritional needs after hospital discharge. Similac NeoCare is a nutritionally complete formula developed to provide premature infants with extra calories, protein, vitamins and minerals needed to promote catch-up growth and support development.

Features:

Reduces the need for caloric and vitamin supplementation. More calories (22 Cal/fl oz) then standard term formulas (20 Cal/fl oz).

Highly absorbed fat blend, with medium-chain triglycerides (MCT oil) to help meet the special digestive needs of premature infants.

Higher levels of protein, vitamins and minerals per 100 Calories to extend the nutritional support initiated in-hospital.

More calcium and phosphorus for improved bone mineralization.

Ingredients: ® -D Corn syrup solids, nonfat milk, lactose, whey protein concentrate, soy oil, high-oleic safflower oil, fractionated coconut oil (medium-chain triglycerides), coconut oil, potassium citrate, calcium phosphate tribasic, calcium carbonate, ascorbic acid, magnesium chloride, potassium chloride, sodium chloride, taurine, ferrous sulfate, m-inositol, choline chloride, ascorbyl palmitate, L-carnitine, alpha-tocopheryl acetate, zinc sulfate, niacinamide, mixed tocopherols, sodium citrate, calcium pantothenate, cupric sulfate, thiamine chloride hydrochloride, vitamin A palmitate, beta carotene, riboflavin, pyridoxine hydrochloride, folic acid, manganese sulfate, phylloquinone, biotin, sodium selenite, vitamin $D_3$ and cyanocobalamin.

G. Similac Natural Care Low-Iron Human Milk Fortifier Ready to Use, 24 Cal/fl oz.

Usage: Designed to be mixed with human milk or to be fed alternatively with human milk to low-birth-weight infants.

Ingredients: ® -D Water, nonfat milk, hydrolyzed cornstarch, lactose, fractionated coconut oil (medium-chain triglycerides), whey protein concentrate, soil oil, coconut oil, calcium phosphate tribasic, potassium citrate, magnesium chloride, sodium citrate, ascorbic acid, calcium carbonate, mono- and diglycerides, soy lecithin, carrageenan, choline chloride, m-inositol, taurine, niacinamide, L-carnitine, alpha tocopheryl acetate, zinc sulfate, potassium chloride, calcium pantothenate, ferrous sulfate, cupric sulfate, riboflavin, vitamin A palmitate, thiamine chloride hydrochloride, pyridoxine hydrochloride, biotin, folic acid, manganese sulfate, phylloquinone, vitamin $D_3$, sodium selenite and cyanocobalamin.

Various PUFAs of this invention can be substituted and/or added to the infant formulae described above and to other infant formulae known to those in the art.

II. Nutritional Formulations

A. ENSURE®

Usage: ENSURE is a low-residue liquid food designed primarily as an oral nutritional supplement to be used with or between meals or, in appropriate amounts, as a meal replacement. ENSURE is lactose- and gluten-free, and is suitable for use in modified diets, including low-cholesterol diets. Although it is primarily an oral supplement, it can be fed by tube.

Patient Conditions:

For patients on modified diets

For elderly patients at nutrition risk

For patients with involuntary weight loss

For patients recovering from illness or surgery

For patients who need a low-residue diet

Ingredients:

® -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate.

B. ENSURE® BARS

Usage: ENSURE BARS are complete, balanced nutrition for supplemental use between or with meals. They provide a delicious, nutrient-rich alternative to other snacks. ENSURE BARS contain <1 g lactose/bar, and Chocolate Fudge Brownie flavor is gluten-free. (Honey Graham Crunch flavor contains gluten.)

Patient Conditions:

For patients who need extra calories, protein, vitamins and minerals

Especially useful for people who do not take in enough calories and nutrients

For people who have the ability to chew and swallow

Not to be used by anyone with a peanut allergy or any type of allergy to nuts.

Ingredients:

Honey Graham Crunch—High-Fructose Corn Syrup, Soy Protein Isolate, Brown Sugar, Honey, Maltodextrin (Corn), Crisp Rice (Milled Rice, Sugar [Sucrose], Salt [Sodium Chloride] and Malt), Oat Bran, Partially Hydrogenated Cottonseed and Soy Oils, Soy Polysaccharide, Glycerine, Whey Protein Concentrate, Polydextrose, Fructose, Calcium Caseinate, Cocoa Powder, Artificial Flavors, Canola Oil, High-Oleic Safflower Oil, Nonfat Dry Milk, Whey Powder, Soy Lecithin and Corn Oil. Manufactured in a facility that processes nuts.

Vitamins and Minerals:

Calcium Phosphate Tribasic, Potassium Phosphate Dibasic, Magnesium Oxide, Salt (Sodium Chloride), Potassium Chloride, Ascorbic Acid, Ferric Orthophosphate, Alpha-Tocopheryl Acetate, Niacinamide, Zinc Oxide, Calcium Pantothenate, Copper Gluconate, Manganese Sulfate, Riboflavin, Beta-Carotene, Pyridoxine Hydrochloride, Thiamine Mononitrate, Folic Acid, Biotin, Chromium Chloride, Potassium Iodide, Sodium Selenate, Sodium Molybdate, Phylloquinone, Vitamin $D_3$ and Cyanocobalamin.

Protein:

Honey Graham Crunch

The protein source is a blend of soy protein isolate and milk proteins.

| | |
|---|---|
| Soy protein isolate | 74% |
| Milk proteins | 26% |

Fat:

Honey Graham Crunch—The fat source is a blend of partially hydrogenated cottonseed and soybean, canola, high oleic safflower, and corn oils, and soy lecithin.

| | |
|---|---|
| Partially hydrogenated cottonseed and soybean oil | 76% |
| Canola oil | 8% |
| High-oleic safflower oil | 8% |
| Corn oil | 4% |
| Soy lecithin | 4% |

Carbohydrate:

Honey Graham Crunch—The carbohydrate source is a combination of high-fructose corn syrup, brown sugar, maltodextrin, honey, crisp rice, glycerine, soy polysaccharide, and oat bran.

| | |
|---|---|
| High-fructose corn syrup | 24% |
| Brown sugar | 21% |
| Maltodextrin | 12% |
| Honey | 11% |
| Crisp rice | 9% |
| Glycerine | 9% |
| Soy polysaccharide | 7% |
| Oat bran | 7%\ |

C. ENSURE® HIGH PROTEIN

Usage: ENSURE HIGH PROTEIN is a concentrated, high-protein liquid food designed for people who require additional calories, protein, vitamins, and minerals in their diets. It can be used as an oral nutritional supplement with or between meals or, in appropriate amounts, as a meal replacement. ENSURE HIGH PROTEIN is lactose- and gluten-free, and is suitable for use by people recovering from general surgery or hip fractures and by patients at risk for pressure ulcers.

Patient Conditions

For patients who require additional calories, protein, vitamins, and minerals, such as patients recovering from general surgery or hip fractures, patients at risk for pressure ulcers, and patients on low-cholesterol diets Features—

Low in saturated fat

Contains 6 g of total fat and <5 mg of cholesterol per serving

Rich, creamy taste

Excellent source of protein, calcium, and other essential vitamins and minerals

For low-cholesterol diets

Lactose-free, easily digested

Ingredients:

Vanilla Supreme: -Ⓤ-D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folio Acid, Sodium Molybdate, Chromium Chloride, Biotin, Potassium Iodide, Sodium Selenate, Phylloquinone, Vitamin D.3 and Cyanocobalarnin.

Protein:

The protein source is a blend of two high-biologic-value proteins: casein and soy.

| | |
|---|---|
| Sodium and calcium caseinates | 85% |
| Soy protein isolate | 15% |

Fat:

The fat source is a blend of three oils: high-oleic safflower, canola, and soy.

| | |
|---|---|
| High-oleic safflower oil | 40% |
| Canola oil | 30% |
| Soy oil | 30% |

The level of fat in ENSURE HIGH PROTEIN meets American Heart Association (AHA) guidelines. The 6 grams of fat in ENSURE HIGH PROTEIN represent 24% of the total calories, with 2.6% of the fat being from saturated fatty acids and 7.9% from polyunsaturated fatty acids. These values are within the AHA guidelines of ≤30% of total calories from fat, <10% of the calories from saturated fatty acids, and ≤10% of total calories from polyunsaturated fatty acids.

Carbohydrate:

ENSURE HIGH PROTEIN contains a combination of maltodextrin and sucrose. The mild sweetness and flavor variety (vanilla supreme, chocolate royal, wild berry, and banana), plus VARI-FLAVORSO® Flavor Pacs in pecan, cherry, strawberry, lemon, and orange, help to prevent flavor fatigue and aid in patient compliance.

Vanilla and Other Nonchocolate Flavors

| | |
|---|---|
| Sucrose | 60% |
| Maltodextrin | 40% |

Chocolate

| | |
|---|---|
| Sucrose | 70% |
| Maltodextrin | 30% |

D. ENSURE® LIGHT

Usage: ENSURE LIGHT is a low-fat liquid food designed for use as an oral nutritional supplement with or between meals. ENSURE LIGHT is lactose- and gluten-free, and is suitable for use in modified diets, including low-cholesterol diets.

Patient Conditions:

For normal-weight or overweight patients who need extra nutrition in a supplement that contains 50% less fat and 20% fewer calories than ENSURE For healthy adults who don't eat right and need extra nutrition Features:

Low in fat and saturated fat

Contains 3 g of total fat per serving and <5 mg cholesterol

Rich, creamy taste

Excellent source of calcium and other essential vitamins and minerals

For low-cholesterol diets

Lactose-free, easily digested

Ingredients:

French Vanilla: Ⓤ-D Water, Maltodextrin (Corn), Sugar (Sucrose), Calcium Caseinate, High-Oleic Safflower Oil, Canola Oil, Magnesium Chloride, Sodium Citrate, Potassium Citrate, Potassium Phosphate Dibasic, Magnesium Phosphate Dibasic, Natural and Artificial Flavor, Calcium Phosphate Tribasic, Cellulose Gel, Choline Chloride, Soy Lecithin, Carrageenan, Salt (Sodium Chloride), Ascorbic Acid, Cellulose Gum, Ferrous Sulfate, Alpha-Tocopheryl Acetate, Zinc Sulfate, Niacinamide, Manganese Sulfate, Calcium Pantothenate, Cupric Sulfate, Thiamine Chloride Hydrochloride, Vitamin A Palmitate, Pyridoxine Hydrochloride, Riboflavin, Chromium Chloride, Folic Acid, Sodium Molybdate, Biotin, Potassium Iodide, Sodium Selenate, Phylloquinone, Vitamin $D_3$ and Cyanocobalamin.

Protein:

The protein source is calcium caseinate.

| Calcium caseinate | 100% |
|---|---|

Fat

The fat source is a blend of two oils: high-oleic safflower and canola.

| High-oleic safflower oil | 70% |
|---|---|
| Canola oil | 30% |

The level of fat in ENSURE LIGHT meets American Heart Association (AHA) guidelines. The 3 grams of fat in ENSURE LIGHT represent 13.5% of the total calories, with 1.4% of the fat being from saturated fatty acids and 2.6% from polyunsaturated fatty acids. These values are within the AHA guidelines of ≤30% of total calories from fat, <10% of the calories from saturated fatty acids, and ≤10% of total calories from polyunsaturated fatty acids.

Carbohydrate

ENSURE LIGHT contains a combination of maltodextrin and sucrose. The chocolate flavor contains corn syrup as well. The mild sweetness and flavor variety (French vanilla, chocolate supreme, strawberry swirl), plus VARI-FLAVORS® Flavor Pacs in pecan, cherry, strawberry, lemon, and orange, help to prevent flavor fatigue and aid in patient compliance.

Vanilla and Other Nonchocolate Flavors

| Sucrose | 51% |
|---|---|
| Maltodextrin | 49% |

Chocolate

| Sucrose | 47.0% |
|---|---|
| Corn Syrup | 26.5% |
| Maltodextrin | 26.5% |

Vitamins and Minerals

An 8-fl-oz serving of ENSURE LIGHT provides at least 25% of the RDIs for 24 key vitamins and minerals.

Caffeine

Chocolate flavor contains 2.1 mg caffeine/8 fl oz.

E. ENSURE PLUS®

Usage: ENSURE PLUS is a high-calorie, low-residue liquid food for use when extra calories and nutrients, but a normal concentration of protein, are needed. It is designed primarily as an oral nutritional supplement to be used with or between meals or, in appropriate amounts, as a meal replacement. ENSURE PLUS is lactose- and gluten-free. Although it is primarily an oral nutritional supplement, it can be fed by tube.

Patient Conditions:

For patients who require extra calories and nutrients, but a normal concentration of protein, in a limited volume For patients who need to gain or maintain healthy weight Features Rich, creamy taste Good source of essential vitamins and minerals Ingredients Vanilla: ⓤ -D Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin $D_3$.

Protein

The protein source is a blend of two high-biologic-value proteins: casein and soy.

| Sodium and calcium caseinates | 84% |
|---|---|
| Soy protein isolate | 16% |

Fat

The fat source is corn oil.

| Corn oil | 100% |
|---|---|

Carbohydrate

ENSURE PLUS contains a combination of maltodextrin and sucrose. The mild sweetness and flavor variety (vanilla, chocolate, strawberry, coffee, buffer pecan, and eggnog), plus VARI-FLAVORS® Flavor Pacs in pecan, cherry, strawberry, lemon, and orange, help to prevent flavor fatigue and aid in patient compliance.

Vanilla, Strawberry, Butter Pecan, and Coffee Flavors

| Corn Syrup | 39% |
|---|---|
| Maltodextrin | 38% |
| Sucrose | 23% |

Chocolate and Eggnog Flavors

| Corn Syrup | 36% |
|---|---|
| Maltodextrin | 34% |
| Sucrose | 30% |

Vitamins and Minerals

An 8-fl-oz serving of ENSURE PLUS provides at least 15% of the RDIs for 25 key Vitamins and minerals.

Caffeine

Chocolate flavor contains 3.1 mg Caffeine/8 fl oz. Coffee flavor contains a trace amount of caffeine.

F. ENSURE PLUS® HN

Usage: ENSURE PLUS HN is a nutritionally complete high-calorie, high-nitrogen liquid food designed for people with higher calorie and protein needs or limited volume tolerance. It may be used for oral supplementation or for total nutritional support by tube. ENSURE PLUS HN is lactose- and gluten-free.

Patient Conditions:

For patients with increased calorie and protein needs, such as following surgery or injury For patients with limited volume tolerance and early satiety Features For supplemental or total nutrition For oral or tube feeding 1.5 CaVmL High nitrogen Calorically dense Ingredients Vanilla: ® -D Water, Maltodextrin (Corn), Sodium and Calcium Caseinates, Corn Oil, Sugar (Sucrose), Soy Protein Isolate, Magnesium Chloride, Potassium Citrate, Calcium Phosphate Tribasic, Soy Lecithin, Natural and Artificial Flavor, Sodium Citrate, Choline Chloride, Ascorbic Acid, Taurine, L-Carnitine, Zinc Sulfate, Ferrous Sulfate, Alpha-Tocopheryl Acetate, Niacinamide, Carrageenan, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin $D_3$.

G. ENSURE® POWDER

Usage: ENSURE POWDER (reconstituted with water) is a low-residue liquid food designed primarily as an oral nutritional supplement to be used with or between meals. ENSURE POWDER is lactose- and gluten-free, and is suitable for use in modified diets, including low-cholesterol diets.

Patient Conditions:

For patients on modified diets

For elderly patients at nutrition risk

For patients recovering from illness/surgery

For patients who need a low-residue diet

Features

Convenient, easy to mix

Low in saturated fat

Contains 9 g of total fat and <5 mg of cholesterol per serving

High in vitamins and minerals

For low-cholesterol diets

Lactose-free, easily digested

Ingredients: ® -D Corn Syrup, Maltodextrin (Corn), Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate Tribasic, Potassium Chloride, Soy Lecithin, Ascorbic Acid, Choline Chloride, Zinc Sulfate, Ferrous Sulfate, Alpha-Tocopheryl Acetate, Niacinamide, Calcium Pantothenate, Manganese Sulfate, Thiamine Chloride Hydrochloride, Cupric Sulfate, Pyridoxine Hydrochloride, Riboflavin, Vitamin A Palmitate, Folic Acid, Biotin, Sodium Molybdate, Chromium Chloride, Potassium Iodide, Sodium Selenate, Phylloquinone, Vitamin $D_3$ and Cyanocobalamin.

Protein

The protein source is a blend of two high-biologic-value proteins: casein and soy.

| | |
|---|---|
| Sodium and calcium caseinates | 84% |
| Soy protein isolate | 16% |

Fat

The fat source is corn oil.

| | |
|---|---|
| Corn oil | 100% |

Carbohydrate

ENSURE POWDER contains a combination of corn syrup, maltodextrin, and sucrose. The mild sweetness of ENSURE POWDER, plus VARI-FLAVORS® Flavor Pacs in pecan, cherry, strawberry, lemon, and orange, helps to prevent flavor fatigue and aid in patient compliance.

Vanilla

| | |
|---|---|
| Corn Syrup | 35% |
| Maltodextrin | 35% |
| Sucrose | 30% |

H. ENSURE® PUDDING

Usage: ENSURE PUDDING is a nutrient-dense supplement providing balanced nutrition in a nonliquid form to be used with or between meals. It is appropriate for consistency-modified diets (e.g., soft, pureed, or full liquid) or for people with swallowing impairments. ENSURE PUDDING is gluten-free.

Patient Conditions:

For patients on consistency-modified diets (e.g., soft, pureed, or full liquid)

For patients with swallowing impairments

Features

Rich and creamy, good taste

Good source of essential vitamins and minerals Convenient—needs no refrigeration Gluten-free Nutrient Profile per 5 oz: Calories 250, Protein 10.9%, Total Fat 34.9%, Carbohydrate 54.2%

Ingredients:

Vanilla: ® -D Nonfat Milk, Water, Sugar (Sucrose), Partially Hydrogenated Soybean Oil, Modified Food Starch, Magnesium Sulfate. Sodium Stearoyl Lactylate, Sodium Phosphate Dibasic, Artificial Flavor, Ascorbic Acid, Zinc Sulfate, Ferrous Sulfate, Alpha-Tocopheryl Acetate, Choline Chloride, Niacinamide, Manganese Sulfate, Calcium Pantothenate, FD&C Yellow #5, Potassium Citrate, Cupric Sulfate, Vitamin A Palmitate, Thiamine Chloride Hydrochloride, Pyridoxine Hydrochloride, Riboflavin, FD&C Yellow #6, Folic Acid, Biotin, Phylloquinone, Vitamin D3 and Cyanocobalamin.

Protein

The protein source is nonfat milk.

| | |
|---|---|
| Nonfat milk | 100% |

Fat

The fat source is hydrogenated soybean oil.

| | |
|---|---|
| Hydrogenated soybean oil | 100% |

Carbohydrate

ENSURE PUDDING contains a combination of sucrose and modified food starch. The mild sweetness and flavor variety (vanilla, chocolate, butterscotch, and tapioca) help prevent flavor fatigue. The product contains 9.2 grams of lactose per serving.

Vanilla and Other Nonchocolate Flavors

| | |
|---|---|
| Sucrose | 56% |
| Lactose | 27% |
| Modified food starch | 17% |

Chocolate

| | |
|---|---|
| Sucrose | 58% |
| Lactose | 26% |
| Modified food starch | 16% |

I. ENSURE® WITH FIBER

Usage: ENSURE WITH FIBER is a fiber-containing, nutritionally complete liquid food designed for people who can benefit from increased dietary fiber and nutrients. ENSURE WITH FIBER is suitable for people who do not require a low-residue diet. It can be fed orally or by tube, and can be used as a nutritional supplement to a regular diet or, in appropriate amounts, as a meal replacement. ENSURE WITH FIBER is lactose- and gluten-free, and is suitable for use in modified diets, including low-cholesterol diets.

Patient Conditions

For patients who can benefit from increased dietary fiber and nutrients

Features

New advanced formula-low in saturated fat, higher in vitamins and minerals

Contains 6 g of total fat and <5 mg of cholesterol per serving

Rich, creamy taste

Good source of fiber

Excellent source of essential vitamins and minerals

For low-cholesterol diets

Lactose- and gluten-free

Ingredients

Vanilla: ⓤ-D Water, Maltodextrin (Corn), Sugar (Sucrose), Sodium and Calcium Caseinates, Oat Fiber, High-Oleic Safflower Oil, Canola Oil, Soy Protein Isolate, Corn Oil, Soy Fiber, Calcium Phosphate Tribasic, Magnesium Chloride, Potassium Citrate, Cellulose Gel, Soy Lecithin, Potassium Phosphate Dibasic, Sodium Citrate, Natural and Artificial Flavors, Choline Chloride, Magnesium Phosphate, Ascorbic Acid, Cellulose Gum, Potassium Chloride, Carrageenan, Ferrous Sulfate, Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin $D_3$ and Cyanocobalamin.

Protein

The protein source is a blend of two high-biologic-value proteins—casein and soy.

| | |
|---|---|
| Sodium and calcium caseinates | 80% |
| Soy protein isolate | 20% |

Fat

The fat source is a blend of three oils: high-oleic safflower, canola, and corn.

| | |
|---|---|
| High-oleic safflower oil | 40% |
| Canola oil | 40% |
| Corn oil | 20% |

The level of fat in ENSURE WITH FIBER meets American Heart Association (AHA) guidelines. The 6 grams of fat in ENSURE WITH FIBER represent 22% of the total calories, with 2.01% of the fat being from saturated fatty acids and 6.7% from polyunsaturated fatty acids. These values are within the AHA guidelines of ≤30% of total calories from fat, <10% of the calories from saturated fatty acids, and ≤10% of total calories from polyunsaturated fatty acids.

Carbohydrate

ENSURE WITH FIBER contains a combination of maltodextrin and sucrose. The mild sweetness and flavor variety (vanilla, chocolate, and butter pecan), plus VARI-FLAVORS® Flavor Pacs in pecan, cherry, strawberry, lemon, and orange, help to prevent flavor fatigue and aid in patient compliance.

Vanilla and Other Nonchocolate Flavors

| | |
|---|---|
| Maltodextrin | 66% |
| Sucrose | 25% |
| Oat Fiber | 7% |
| Soy Fiber | 2% |

Chocolate

| | |
|---|---|
| Maltodextrin | 55% |
| Sucrose | 36% |
| Oat Fiber | 7% |
| Soy Fiber | 2% |

Fiber

The fiber blend used in ENSURE WITH FIBER consists of oat fiber and soy polysaccharide. This blend results in approximately 4 grams of total dietary fiber per 8-fl-oz can. The ratio of insoluble to soluble fiber is 95:5.

The various nutritional supplements described above and known to others of skill in the art can be substituted and/or supplemented with the PUFAs of this invention.

J. Oxepa™ Nutritional Product

Oxepa is low-carbohydrate, calorically dense enteral nutritional product designed for the dietary management of patients with or at risk for ARDS. It has a unique combination of ingredients, including a patented oil blend containing eicosapentaenoic acid (EPA from fish oil), γ-linolenic acid (GLA from borage oil), and elevated antioxidant levels.

Caloric Distribution:

Caloric density is high at 1.5 Cal/mL (355 Cal/8 fl oz), to minimize the volume required to meet energy needs.

The distribution of Calories in Oxepa is shown in Table 7.

TABLE 7

Caloric Distribution of Oxepa

| | per 8 fl oz. | per liter | % of Cal |
|---|---|---|---|
| Calories | 355 | 1,500 | — |
| Fat (g) | 22.2 | 93.7 | 55.2 |
| Carbohydrate (g) | 25 | 105.5 | 28.1 |
| Protein (g) | 14.8 | 62.5 | 16.7 |
| Water (g) | 186 | 785 | — |

Fat:

Oxepa contains 22.2 g of fat per 8-fl oz serving (93.7 g/L).

The fat source is a oil blend of 31.8% canola oil, 25% medium-chain triglycerides (MCTs), 20% borage oil, 20% fish oil, and 3.2% soy lecithin. The typical fatty acid profile of Oxepa is shown in Table 8.

Oxepa provides a balanced amount of polyunsaturated, monounsaturated, and saturated fatty acids, as shown in Table 10.

Medium-chain triglycerides (MCTs)—25% of the fat blend—aid gastric emptying because they are absorbed by the intestinal tract without emulsification by bile acids.

The various fatty acid components of Oxepa™ nutritional product can be substituted and/or supplemented with the PUFAs of this invention.

TABLE 8

Typical Fatty Acid Profile

| | % Total Fatty Acids | g/8 fl oz* | g/L* |
|---|---|---|---|
| Caproic (6:0) | 0.2 | 0.04 | 0.18 |
| Caprylic (8:0) | 14.69 | 3.1 | 13.07 |
| Capric (10:0) | 11.06 | 2.33 | 9.87 |
| Palmitic (16:0) | 5.59 | 1.18 | 4.98 |
| Palmitoleic (16:1n-7) | 1.82 | 0.38 | 1.62 |
| Stearic (18:0) | 1.84 | 0.39 | 1.64 |
| Oleic (18:1n-9) | 24.44 | 5.16 | 21.75 |
| Linoleic (18:2n-6) | 16.28 | 3.44 | 14.49 |
| α-Linolenic (18:3n-3) | 3.47 | 0.73 | 3.09 |
| γ-Linolenic (18:3n-6) | 4.82 | 1.02 | 4.29 |
| Eicosapentaenoic (20:5n-3) | 5.11 | 1.08 | 4.55 |
| n-3-Docosapentaenoic (22:5n-3) | 0.55 | 0.12 | 0.49 |
| Docosahexaenoic (22:6n-3) | 2.27 | 0.48 | 2.02 |
| Others | 7.55 | 1.52 | 6.72 |

*Fatty acids equal approximately 95% of total fat.

TABLE 9

Fat Profile of Oxepa.

| | |
|---|---|
| % of total calories from fat | 55.2 |
| Polyunsaturated fatty acids | 31.44 g/L |
| Monounsaturated fatty acids | 25.53 g/L |
| Saturated fatty acids | 32.38 g/L |
| n-6 to n-3 ratio | 1.75:1 |
| Cholesterol | 9.49 mg/8 fl oz<br>40.1 mg/L |

Carbohydrate:

The carbohydrate content is 25.0 g per 8-fl-oz serving (105.5 g/L).

The carbohydrate sources are 45% maltodextrin (a complex carbohydrate) and 55% sucrose (a simple sugar), both of which are readily digested and absorbed.

The high-fat and low-carbohydrate content of Oxepa is designed to minimize carbon dioxide ($CO_2$) production. High $CO_2$ levels can complicate weaning in ventilator-dependent patients. The low level of carbohydrate also may be useful for those patients who have developed stress-induced hyperglycemia.

Oxepa is lactose-free.

Dietary carbohydrate, the amino acids from protein, and the glycerol moiety of fats can be converted to glucose within the body. Throughout this process, the carbohydrate requirements of glucose-dependent tissues (such as the central nervous system and red blood cells) are met. However, a diet free of carbohydrates can lead to ketosis, excessive catabolism of tissue protein, and loss of fluid and electrolytes. These effects can be prevented by daily ingestion of 50 to 100 g of digestible carbohydrate, if caloric intake is adequate. The carbohydrate level in Oxepa is also sufficient to minimize gluconeogenesis, if energy needs are being met.

Protein:

Oxepa contains 14.8 g of protein per 8-fl-oz serving (62.5 g/L).

The total calorie/nitrogen ratio (150:1) meets the need of stressed patients.

Oxepa provides enough protein to promote anabolism and the maintenance of lean body mass without precipitating respiratory problems. High protein intakes are a concern in patients with respiratory insufficiency. Although protein has little effect on $CO_2$ production, a high protein diet will increase ventilatory drive.

The protein sources of Oxepa are 86.8% sodium caseinate and 13.2% calcium caseinate.

As demonstrated in Table 11, the amino acid profile of the protein system in Oxepa meets or surpasses the standard for high quality protein set by the National Academy of Sciences.

Oxepa is gluten-free.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A nutritional formula comprising a microbial oil produced by:

growing one or more transgenic microbial cells under suitable conditions whereby said cells express a transgenic polypeptide wherein the sequence of said polypeptide comprises a sequence selected from the group consisting of residues 39-43, 172-176, 204-213, and 390-402 of SEQ ID NO:2.

2. The nutritional formula of claim 1, wherein said nutritional formula is selected from the group consisting of an infant formula, a dietary supplement, and a dietary substitute.

3. The nutritional formula of claim 2, wherein said infant formula, dietary supplement or dietary substitute is in the form of a liquid or a solid.

4. The nutritional formula of claim 2, wherein said nutritional formula is an infant formula, and wherein said infant formula further comprises at least one macronutrient selected from the group consisting of coconut oil, soy oil, canola oil, mono- and diglycerides, glucose, edible lactose, electrodialysed whey, electrodialysed skim milk, milk whey, soy protein, and other protein hydrolysates.

5. The nutritional formula of claim 4 further comprising at least one vitamin selected from the group consisting of Vitamins A, C, D, E, and B complex; and at least one mineral selected from the group consisting of calcium, magnesium, zinc, manganese, sodium, potassium, phosphorus, copper, chloride, iodine, selenium, and iron.

6. The nutritional formula of claim 2, wherein said nutritional formula is a dietary supplement, and wherein said dietary supplement further comprises at least one macronutrient selected from the group consisting of coconut oil, soy oil, canola oil, mono- and diglycerides, glucose, edible lactose, electrodialysed whey, electrodialysed skim milk, milk whey, soy protein, and other protein hydrolysates.

7. The nutritional formula of claim 6 further comprising at least one vitamin selected from the group consisting of Vitamins A, C, D, E, and B complex; and at least one mineral selected from the group consisting of calcium, magnesium, zinc, manganese, sodium, potassium, phosphorus, copper, chloride, iodine, selenium, and iron.

8. The nutritional formula of claim 6 wherein said dietary supplement is administered to a human or an animal.

9. The nutritional formula of claim 2, wherein said nutritional formula is a dietary substitute, and wherein said dietary substitute further comprises at least one macronutrient selected from the group consisting of coconut oil, soy oil, canola oil, mono- and diglycerides, glucose, edible lactose, electrodialysed whey, electrodialysed skim milk, milk whey, soy protein, and other protein hydrolysates.

10. The nutritional formula of claim 9 further comprising at least one vitamin selected from the group consisting of Vitamins A, C, D, E, and B complex; and at least one mineral selected from the group consisting of calcium, magnesium, zinc, manganese, sodium, potassium, phosphorus, copper, chloride, iodine, selenium, and iron.

11. The nutritional formula of claim 9, wherein said dietary substitute is administered to a human or animal.

12. A nutritional formula comprising a microbial oil produced by:

growing microbial cells which contain one or more transgenes which encode a transgene expression product under conditions whereby said one or more transgenes are expressed, whereby long chain polyunsaturated fatty acid biosynthesis in said cells is altered whereby said transgene comprises a nucleotide sequence which encodes a polypeptide wherein the sequence of the polypeptide comprises a sequence selected from the group consisting of SEQ ID NO:4, SEQ ID NO:20, SEQ ID NO:22, SEQ ID NO:24, and SEQ ID NO:26.

13. The nutritional formula of claim 12, wherein said nutritional formula is selected from the group consisting of an infant formula, a dietary supplement, and a dietary substitute.

14. The nutritional formula of claim 13, wherein said infant formula, dietary supplement or dietary substitute is in the form of a liquid or a solid.

15. The nutritional formula of claim 13, wherein said nutritional formula is an infant formula, and wherein said infant formula further comprises at least one macronutrient selected from the group consisting of coconut oil, soy oil, canola oil, mono- and diglycerides, glucose, edible lactose, electrodialysed whey, electrodialysed skim milk, milk whey, soy protein, and other protein hydrolysates.

16. The nutritional formula of claim 15 further comprising at least one vitamin selected from the group consisting of Vitamins A, C, D, E, and B complex; and at least one mineral selected from the group consisting of calcium, magnesium, zinc, manganese, sodium, potassium, phosphorus, copper, chloride, iodine, selenium, and iron.

17. The nutritional formula of claim 13, wherein said nutritional formula is a dietary supplement, and wherein said dietary supplement further comprises at least one macronutrient selected from the group consisting of coconut oil, soy oil, canola oil, mono- and diglycerides, glucose, edible lactose, electrodialysed whey, electrodialysed skim milk, milk whey, soy protein, and other protein hydrolysates.

18. The nutritional formula of claim 17 further comprising at least one vitamin selected from the group consisting of Vitamins A, C, D, E, and B complex; and at least one mineral selected from the group consisting of calcium, magnesium, zinc, manganese, sodium, potassium, phosphorus, copper, chloride, iodine, selenium, and iron.

19. The nutritional formula of claim 17 wherein said dietary supplement is administered to a human or an animal.

20. The nutritional formula of claim 13, wherein said nutritional formula is a dietary substitute, and wherein said dietary substitute further comprises at least one macronutrient selected from the group consisting of coconut oil, soy oil, canola oil, mono- and diglycerides, glucose, edible lactose, electrodialysed whey, electrodialysed skim milk, milk whey, soy protein, and other protein hydrolysates.

21. The nutritional formula of claim 20 further comprising at least one vitamin selected from the group consisting of Vitamins A, C, D, E, and B complex; and at least one mineral selected from the group consisting of calcium, magnesium, zinc, manganese, sodium, potassium, phosphorus, copper, chloride, iodine, selenium, and iron.

22. The nutritional formula of claim 20, wherein said dietary substitute is administered to a human or animal.

23. A nutritional formula comprising a microbial oil produced by:

growing one or more transgenic microbial cells under suitable conditions whereby said cells express one or more transgenic polypeptides wherein the sequence of said one or more polypeptides comprises a sequence selected from the group consisting of SEQ ID NO:4, SEQ ID N0:20, SEQ ID NO:22, SEQ ID NO:24, and SEQ ID NO:26.

24. The nutritional formula of claim 23, wherein said nutritional formula is selected from the group consisting of an infant formula, a dietary supplement, and a dietary substitute.

25. The nutritional formula of claim 24, wherein said infant formula, dietary supplement or dietary substitute is in the form of a liquid or a solid.

26. The nutritional formula of claim 24, wherein said nutritional formula is an infant formula, and wherein said infant formula further comprises at least one macronutrient selected from the group consisting of coconut oil, soy oil, canola oil, mono- and diglycerides, glucose, edible lactose, electrodialysed whey, electrodialysed skim milk, milk whey, soy protein, and other protein hydrolysates.

27. The nutritional formula of claim 26 further comprising at least one vitamin selected from the group consisting of Vitamins A, C, D, E, and B complex; and at least one mineral selected from the group consisting of calcium, magnesium, zinc, manganese, sodium, potassium, phosphorus, copper, chloride, iodine, selenium, and iron.

28. The nutritional formula of claim 24, wherein said nutritional formula is a dietary supplement, and wherein said dietary supplement further comprises at least one macronutrient selected from the group consisting of coconut oil, soy oil, canola oil, mono- and diglycerides, glucose, edible lactose, electrodialysed whey, electrodialysed skim milk, milk whey, soy protein, and other protein hydrolysates.

29. The nutritional formula of claim 28 further comprising at least one vitamin selected from the group consisting of Vitamins A, C, D, E, and B complex; and at least one mineral selected from the group consisting of calcium, magnesium, zinc, manganese, sodium, potassium, phosphorus, copper, chloride, iodine, selenium, and iron.

30. The nutritional formula of claim 28 wherein said dietary supplement is administered to a human or an animal.

31. The nutritional formula of claim 24, wherein said nutritional formula is a dietary substitute, and wherein said dietary substitute further comprises at least one macronutrient selected from the group consisting of coconut oil, soy oil, canola oil, mono- and diglycerides, glucose, edible lactose, electrodialysed whey, electrodialysed skim milk, milk whey, soy protein, and other protein hydrolysates.

32. The nutritional formula of claim 31 further comprising at least one vitamin selected from the group consisting of Vitamins A, C, D, E, and B complex; and at least one mineral selected from the group consisting of calcium, magnesium, zinc, manganese, sodium, potassium, phosphorus, copper, chloride, iodine, selenium, and iron.

33. The nutritional formula of claim 31, wherein said dietary substitute is administered to a human or animal.

* * * * *